US012589128B2

(12) United States Patent
O'Shea et al.

(10) Patent No.: US 12,589,128 B2
(45) Date of Patent: Mar. 31, 2026

(54) ONCOLYTIC ADENOVIRUS COMPOSITIONS

(71) Applicant: Salk Institute for Biological Studies, La Jolla, CA (US)

(72) Inventors: Clodagh O'Shea, San Diego, CA (US); Shigeki Miyake-Stoner, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 1132 days.

(21) Appl. No.: 17/371,546

(22) Filed: Jul. 9, 2021

(65) Prior Publication Data

US 2022/0096577 A1 Mar. 31, 2022

Related U.S. Application Data

(60) Division of application No. 14/852,981, filed on Sep. 14, 2015, now Pat. No. 11,077,156, which is a continuation of application No. PCT/US2014/029587, filed on Mar. 14, 2014.

(60) Provisional application No. 61/782,932, filed on Mar. 14, 2013.

(51) Int. Cl.
| | |
|---|---|
| *A61P 35/00* | (2006.01) |
| *A61K 35/761* | (2015.01) |
| *A61K 35/768* | (2015.01) |
| *A61K 48/00* | (2006.01) |
| *C12N 7/00* | (2006.01) |
| *C12N 15/86* | (2006.01) |
| *C12N 15/861* | (2006.01) |

(52) U.S. Cl.
CPC .......... *A61K 35/761* (2013.01); *A61K 35/768* (2013.01); *C12N 7/00* (2013.01); *C12N 15/86* (2013.01); *C12N 2710/10021* (2013.01); *C12N 2710/10032* (2013.01); *C12N 2710/10043* (2013.01)

(58) Field of Classification Search
None
See application file for complete search history.

(56) References Cited

U.S. PATENT DOCUMENTS

| | | | |
|---|---|---|---|
| 5,543,328 | A | 8/1996 | McClelland et al. |
| 5,559,099 | A | 9/1996 | Wickham et al. |
| 5,670,488 | A | 9/1997 | Gregory et al. |
| 5,677,178 | A | 10/1997 | McCormick |
| 5,731,190 | A | 3/1998 | Wickham et al. |
| 5,801,029 | A | 9/1998 | McCormick |
| 5,846,782 | A | 12/1998 | Wickham et al. |
| 5,846,945 | A | 12/1998 | McCormick |
| 5,856,181 | A | 1/1999 | McCormick |
| 5,922,315 | A | 7/1999 | Roy |
| 5,945,335 | A | 8/1999 | Colosi |
| 5,962,311 | A | 10/1999 | Wickham et al. |
| 5,965,541 | A | 10/1999 | Wickham et al. |
| 5,972,706 | A | 10/1999 | McCormick |
| 6,020,172 | A | 2/2000 | Both |
| 6,069,134 | A | 5/2000 | Roth et al. |
| 6,127,525 | A | 10/2000 | Crystal et al. |
| 6,133,243 | A | 10/2000 | Kirn |
| 6,153,435 | A | 11/2000 | Crystal et al. |
| 6,296,845 | B1 | 10/2001 | Sampson et al. |
| 6,329,190 | B1 | 12/2001 | Wickham et al. |
| 6,410,010 | B1 | 6/2002 | Zhang et al. |
| 6,455,314 | B1 | 9/2002 | Wickham et al. |
| 6,465,253 | B1 | 10/2002 | Wickham et al. |
| 6,475,480 | B1 | 11/2002 | Mehtali et al. |
| 6,506,379 | B1 | 1/2003 | Clackson et al. |
| 6,506,602 | B1 | 1/2003 | Stemmer |
| 6,569,677 | B1 | 5/2003 | Legrand et al. |
| 6,596,268 | B1 | 7/2003 | Coffey et al. |
| 6,635,466 | B2 | 10/2003 | Davidson et al. |
| 6,635,476 | B1 | 10/2003 | Murphy |
| 6,649,157 | B2 | 11/2003 | Coffey et al. |
| 6,737,234 | B1 | 5/2004 | Freimuth |
| 6,740,525 | B2 | 5/2004 | Roelvink et al. |
| 6,797,702 | B1 | 9/2004 | Roth et al. |
| 6,811,774 | B2 | 11/2004 | Haddada et al. |
| 6,824,771 | B1 | 11/2004 | Curiel et al. |
| 6,838,285 | B2 | 1/2005 | Farmer et al. |
| 6,841,540 | B1 | 1/2005 | Curiel et al. |

(Continued)

FOREIGN PATENT DOCUMENTS

| | | |
|---|---|---|
| CN | 1330715 A | 1/2002 |
| CN | 1380420 A | 11/2002 |

(Continued)

OTHER PUBLICATIONS

Goodrich et al, The retinoblastoma tumor suppressor gene, the exception that proves the rule, Oncogene, 2006, pp. 5233-5243.*
Wang et al, Adenovirus vector-attributed hepatotoxicity blocks clinical application in gene therapy, Cytotherapy, 2021, pp. 1045-1052.*
Chen et al, Oncolytic virotherapy in cancer treatment: challenges and optimization prospects. Front. Immunol, 2023, pp. 1-14.*
Zheng et al, Oncolytic Viruses for Cancer Therapy: Barriers and Recent Advances, Molecular Therapy: Oncolytics, 2019, pp. 234-247.*

(Continued)

*Primary Examiner* — Maria Marvich
(74) *Attorney, Agent, or Firm* — Klarquist Sparkman, LLP

(57) ABSTRACT

An adenovirus comprising an E1A polypeptide comprising one or more modifications and comprising an E4orf6/7 polypeptide comprising one or more modifications is described. Compositions and kits comprising the modified adenoviruses are also described. Further described is a method of treating a proliferative disorder in a subject comprising administering to the subject an adenovirus comprising the E1A polypeptide comprising one or more modifications and comprising the E4orf6/7 polypeptide comprising one or more modifications.

10 Claims, 24 Drawing Sheets

Specification includes a Sequence Listing.

(56)                    References Cited

U.S. PATENT DOCUMENTS

| | | | |
|---|---|---|---|
| 6,849,446 B2 | 2/2005 | Tikoo et al. |
| 6,867,022 B1 | 3/2005 | Imperiale |
| 6,869,936 B1 | 3/2005 | Vogels et al. |
| 6,878,549 B1 | 4/2005 | Vogels et al. |
| 6,905,678 B2 | 6/2005 | Havenga et al. |
| 6,911,199 B2 | 6/2005 | Vigne et al. |
| 6,911,200 B2 | 6/2005 | Yu et al. |
| 6,913,922 B1 | 7/2005 | Bout et al. |
| 6,929,946 B1 | 8/2005 | Vogels et al. |
| 6,951,755 B2 | 10/2005 | Wickham et al. |
| 6,984,635 B1 | 1/2006 | Schreiber et al. |
| 7,001,596 B1 | 2/2006 | Johnson et al. |
| 7,045,347 B2 | 5/2006 | Graham et al. |
| 7,094,398 B1 | 8/2006 | Lieber et al. |
| 7,094,399 B2 | 8/2006 | Otto |
| 7,109,179 B2 | 9/2006 | Roth et al. |
| 7,157,266 B2 | 1/2007 | Freimuth et al. |
| 7,232,899 B2 | 6/2007 | Von Seggern et al. |
| 7,235,233 B2 | 6/2007 | Havenga et al. |
| 7,247,472 B2 | 7/2007 | Wilson et al. |
| 7,252,817 B2 | 8/2007 | Coffey et al. |
| 7,252,989 B1 | 8/2007 | Zhang et al. |
| 7,256,036 B2 | 8/2007 | Legrand et al. |
| 7,291,498 B2 | 11/2007 | Roy et al. |
| 7,297,542 B2 | 11/2007 | Curiel et al. |
| 7,306,793 B2 | 12/2007 | Haddada et al. |
| 7,332,337 B2 | 2/2008 | van Es et al. |
| 7,344,711 B2 | 3/2008 | Bonastre et al. |
| 7,344,872 B2 | 3/2008 | Gao et al. |
| 7,364,727 B2 | 4/2008 | Li et al. |
| 7,410,954 B2 | 8/2008 | Davidson et al. |
| 7,456,008 B2 | 11/2008 | Lindholm et al. |
| 7,473,418 B2 | 1/2009 | Yu et al. |
| 7,482,156 B2 | 1/2009 | Arroyo et al. |
| 7,491,508 B2 | 2/2009 | Roy et al. |
| 7,510,868 B2 | 3/2009 | Harden et al. |
| 7,589,069 B1 | 9/2009 | Wold et al. |
| 7,611,868 B2 | 11/2009 | Monaci et al. |
| 7,741,099 B2 | 6/2010 | Havenga et al. |
| 7,749,493 B2 | 7/2010 | Havenga et al. |
| 7,754,201 B2 | 7/2010 | Wang et al. |
| 7,906,113 B2 | 3/2011 | Bout et al. |
| 7,943,373 B2 | 5/2011 | Fujiwara et al. |
| 7,951,585 B2 | 5/2011 | Ke |
| 7,968,333 B2 | 6/2011 | Yu et al. |
| 8,105,574 B2 | 1/2012 | Wilson et al. |
| 8,168,168 B2 | 5/2012 | Fueyo et al. |
| 8,231,880 B2 | 7/2012 | Roy et al. |
| 8,470,310 B2 | 6/2013 | Roy et al. |
| 8,524,219 B2 | 9/2013 | Roy et al. |
| 8,603,459 B2 | 12/2013 | Wilson et al. |
| 8,685,387 B2 | 4/2014 | Roy et al. |
| 8,715,642 B2 | 5/2014 | Kochanek et al. |
| 8,765,146 B2 | 7/2014 | Bruder et al. |
| 8,765,463 B2 | 7/2014 | Harden et al. |
| 8,808,986 B2 | 8/2014 | Jacobson et al. |
| 8,815,563 B2 | 8/2014 | Davis et al. |
| 8,834,863 B2 | 9/2014 | Roy et al. |
| 8,846,031 B2 | 9/2014 | Roy et al. |
| 8,865,182 B2 | 10/2014 | Mayall et al. |
| 8,920,813 B2 | 12/2014 | Bruder et al. |
| 8,940,290 B2 | 1/2015 | Roy et al. |
| 8,974,777 B2 | 3/2015 | Cascallo et al. |
| 9,017,672 B2 | 4/2015 | Yu et al. |
| 9,018,182 B2 | 4/2015 | Koh et al. |
| 9,056,090 B2 | 6/2015 | Colloca et al. |
| 9,061,055 B2 | 6/2015 | Fueyo et al. |
| 9,133,483 B2 | 9/2015 | Wilson et al. |
| 9,163,261 B2 | 10/2015 | Kollipara et al. |
| 9,187,733 B2 | 11/2015 | O'Shea et al. |
| 9,200,041 B2 | 12/2015 | Lieber et al. |
| 9,206,238 B2 | 12/2015 | Roy et al. |
| 9,217,159 B2 | 12/2015 | Roy et al. |
| 9,217,160 B2 | 12/2015 | O'Shea et al. |
| 9,267,153 B2 | 2/2016 | Curiel |
| 9,315,827 B2 | 4/2016 | Wang et al. |
| 9,359,618 B2 | 6/2016 | Roy et al. |
| 9,382,551 B2 | 7/2016 | Roy et al. |
| 9,410,129 B2 | 8/2016 | Ranki et al. |
| 9,476,061 B2 | 10/2016 | Baker et al. |
| 9,493,745 B2 | 11/2016 | Lee et al. |
| 9,555,089 B2 | 1/2017 | Shiratsuchi et al. |
| 9,593,346 B2 | 3/2017 | Roy et al. |
| 9,597,363 B2 | 3/2017 | Roy et al. |
| 9,682,133 B2 | 6/2017 | Crystal et al. |
| 9,688,727 B2 | 6/2017 | Lieber et al. |
| 9,714,435 B2 | 7/2017 | Dicks et al. |
| 9,718,863 B2 | 8/2017 | Colloca et al. |
| 9,790,519 B2 | 10/2017 | Wei et al. |
| 9,885,090 B2 | 2/2018 | O'Shea et al. |
| 9,913,866 B2 | 3/2018 | O'Shea et al. |
| 10,016,470 B2 | 7/2018 | Bonastre et al. |
| 10,034,905 B2 | 7/2018 | Seymour et al. |
| 10,046,067 B2 | 8/2018 | Yun et al. |
| 10,066,215 B2 | 9/2018 | Lee et al. |
| 10,071,126 B2 | 9/2018 | Kumon et al. |
| 10,077,430 B2 | 9/2018 | Lee et al. |
| 10,080,774 B2 | 9/2018 | Fueyo et al. |
| 10,113,182 B2 | 10/2018 | Roy et al. |
| 10,149,873 B2 | 12/2018 | Roy et al. |
| 10,150,798 B2 | 12/2018 | Lieber et al. |
| 10,155,930 B2 | 12/2018 | Holm |
| 10,232,053 B2 | 3/2019 | Hicklin et al. |
| 10,272,162 B2 | 4/2019 | McVey et al. |
| 10,294,493 B2 | 5/2019 | Wang et al. |
| 10,316,065 B2 | 6/2019 | Carrió et al. |
| 10,376,549 B2 | 8/2019 | Shayakhmetov et al. |
| 10,391,183 B2 | 8/2019 | Fueyo-Margareto et al. |
| 10,501,757 B2 | 12/2019 | Roy et al. |
| 10,538,744 B2 | 1/2020 | Holm |
| 10,544,192 B2 | 1/2020 | Colloca et al. |
| 10,577,589 B2 | 3/2020 | O'Shea et al. |
| 10,604,549 B2 | 3/2020 | Alemany Bonastre et al. |
| 10,611,803 B2 | 4/2020 | Lieber et al. |
| 10,617,729 B2 | 4/2020 | Dobbins |
| 10,738,325 B2 | 8/2020 | O'Shea et al. |
| 11,077,156 B2 | 8/2021 | O'Shea et al. |
| 11,130,968 B2 | 9/2021 | O'Shea et al. |
| 11,401,529 B2 | 8/2022 | O'Shea et al. |
| 12,281,324 B2 | 4/2025 | O'Shea et al. |
| 2001/0039046 A1 | 11/2001 | Yeh et al. |
| 2002/0037274 A1 | 3/2002 | Williams et al. |
| 2002/0086411 A1 | 7/2002 | Holm et al. |
| 2002/0106382 A1 | 8/2002 | Young et al. |
| 2002/0142989 A1 | 10/2002 | Alemany et al. |
| 2002/0151069 A1 | 10/2002 | Korokhov |
| 2002/0168343 A1 | 11/2002 | Curiel et al. |
| 2002/0187128 A1 | 12/2002 | Imperiale |
| 2002/0193327 A1 | 12/2002 | Nemerow |
| 2002/0193328 A1 | 12/2002 | Ketner |
| 2003/0017138 A1 | 1/2003 | Havenga et al. |
| 2003/0021768 A1 | 1/2003 | Shen |
| 2003/0027338 A1 | 2/2003 | Freimuth |
| 2003/0073072 A1 | 4/2003 | Havenga et al. |
| 2003/0082146 A1 | 5/2003 | van Es |
| 2003/0082150 A1 | 5/2003 | Boon Falleur et al. |
| 2003/0082811 A1 | 5/2003 | Orlando et al. |
| 2003/0092162 A1 | 5/2003 | Shankara et al. |
| 2003/0095989 A1 | 5/2003 | Irving et al. |
| 2003/0099615 A1 | 5/2003 | Tikoo |
| 2003/0099619 A1 | 5/2003 | Wickham et al. |
| 2003/0104625 A1 | 6/2003 | Cheng et al. |
| 2003/0138405 A1 | 7/2003 | Fueyo et al. |
| 2003/0143730 A1 | 7/2003 | Blanche et al. |
| 2003/0166286 A1 | 9/2003 | Wickham et al. |
| 2003/0170899 A1 | 9/2003 | McVey et al. |
| 2003/0175244 A1 | 9/2003 | Curiel et al. |
| 2003/0175245 A1 | 9/2003 | Brough et al. |
| 2003/0215948 A1 | 11/2003 | Kaleko et al. |
| 2003/0219899 A1 | 11/2003 | Korokhov |
| 2003/0220284 A1 | 11/2003 | Yotnda et al. |
| 2004/0002060 A1 | 1/2004 | Kaleko et al. |
| 2004/0038205 A1 | 2/2004 | Van Raaij et al. |
| 2004/0091456 A1 | 5/2004 | Nakai et al. |

(56)  References Cited

U.S. PATENT DOCUMENTS

| | | |
|---|---|---|
| 2004/0102382 A1 | 5/2004 | Schughart et al. |
| 2004/0146489 A1 | 7/2004 | Yu et al. |
| 2004/0175362 A1 | 9/2004 | Curiel et al. |
| 2004/0185555 A1 | 9/2004 | Emini et al. |
| 2004/0191222 A1 | 9/2004 | Emini et al. |
| 2004/0191761 A1 | 9/2004 | Routes |
| 2004/0213764 A1 | 10/2004 | Wold et al. |
| 2004/0219516 A1 | 11/2004 | Bennett et al. |
| 2004/0219543 A1 | 11/2004 | Wirtz |
| 2004/0265277 A1 | 12/2004 | Holm |
| 2005/0032045 A1 | 2/2005 | Tikoo et al. |
| 2005/0036989 A1 | 2/2005 | Shen et al. |
| 2005/0079158 A1 | 4/2005 | Zhou et al. |
| 2005/0095231 A1 | 5/2005 | Curiel et al. |
| 2005/0095705 A1 | 5/2005 | Kadan et al. |
| 2005/0169891 A1 | 8/2005 | Vogels et al. |
| 2005/0181507 A1 | 8/2005 | Havenga et al. |
| 2005/0186178 A1 | 8/2005 | Ennist |
| 2005/0201936 A1 | 9/2005 | Wold et al. |
| 2005/0201978 A1 | 9/2005 | Lipton |
| 2005/0232900 A1 | 10/2005 | Vogels et al. |
| 2005/0238622 A1 | 10/2005 | Axelrod et al. |
| 2005/0260162 A1 | 11/2005 | Fueyo et al. |
| 2005/0271622 A1 | 12/2005 | Zhou et al. |
| 2005/0277193 A1 | 12/2005 | Wickham et al. |
| 2005/0287120 A1 | 12/2005 | Fisher et al. |
| 2006/0002893 A1 | 1/2006 | Vigne et al. |
| 2006/0034804 A1 | 2/2006 | Gregory et al. |
| 2006/0099178 A1 | 5/2006 | Holm |
| 2006/0104953 A1 | 5/2006 | Havenga et al. |
| 2006/0140910 A1 | 6/2006 | Gregory et al. |
| 2006/0147420 A1 | 7/2006 | Fueyo et al. |
| 2006/0182718 A1 | 8/2006 | Roth et al. |
| 2006/0211115 A1 | 9/2006 | Roy et al. |
| 2006/0228334 A1 | 10/2006 | Rosa Calatrava et al. |
| 2006/0257370 A1 | 11/2006 | Hermiston et al. |
| 2006/0281090 A1 | 12/2006 | Lieber et al. |
| 2006/0286121 A1 | 12/2006 | Gall et al. |
| 2006/0292122 A1 | 12/2006 | Hermiston et al. |
| 2006/0292682 A1 | 12/2006 | Hawkins et al. |
| 2007/0003923 A1 | 1/2007 | Nemerow |
| 2007/0110719 A1 | 5/2007 | Holm |
| 2007/0122817 A1 | 5/2007 | Church et al. |
| 2007/0202080 A1 | 8/2007 | Yun et al. |
| 2007/0202524 A1 | 8/2007 | Murphy |
| 2007/0253932 A1 | 11/2007 | Gregory et al. |
| 2007/0254357 A1 | 11/2007 | Gregory et al. |
| 2007/0292396 A1 | 12/2007 | Fueyo et al. |
| 2007/0292954 A1 | 12/2007 | Elledge |
| 2008/0069836 A1 | 3/2008 | Nabel et al. |
| 2008/0089864 A1 | 4/2008 | Bonastre et al. |
| 2008/0108129 A1 | 5/2008 | Pitcovski et al. |
| 2008/0112929 A1 | 5/2008 | Kovesdi et al. |
| 2008/0118470 A1 | 5/2008 | Ennist et al. |
| 2008/0124360 A1 | 5/2008 | Seggern |
| 2008/0213220 A1 | 9/2008 | Fisher et al. |
| 2008/0242608 A1 | 10/2008 | Bonni et al. |
| 2008/0247996 A1 | 10/2008 | Yu et al. |
| 2008/0254059 A1 | 10/2008 | Bett et al. |
| 2009/0074810 A1 | 3/2009 | Roy et al. |
| 2009/0111144 A1 | 4/2009 | Bebbington |
| 2009/0202565 A1 | 8/2009 | Labow et al. |
| 2009/0232800 A1 | 9/2009 | Holm |
| 2009/0280089 A1 | 11/2009 | Benihoud et al. |
| 2009/0311219 A1 | 12/2009 | Bonastre et al. |
| 2010/0008977 A1 | 1/2010 | Boulikas et al. |
| 2010/0034774 A1 | 2/2010 | Vogels et al. |
| 2010/0047208 A1 | 2/2010 | Ke |
| 2010/0075951 A1 | 3/2010 | Cardin et al. |
| 2010/0075998 A1 | 3/2010 | Vanotti et al. |
| 2010/0098668 A1 | 4/2010 | Seth |
| 2010/0151576 A1 | 6/2010 | Li et al. |
| 2010/0233125 A1 | 9/2010 | Tagawa |
| 2010/0272753 A1 | 10/2010 | Ketner et al. |
| 2010/0292166 A1 | 11/2010 | Lee et al. |
| 2010/0310554 A1 | 12/2010 | Holm |
| 2010/0311145 A1 | 12/2010 | Holm |
| 2011/0053249 A1 | 3/2011 | Bonastre et al. |
| 2011/0059135 A1 | 3/2011 | Kovesdi et al. |
| 2011/0086063 A1 | 4/2011 | Crystal et al. |
| 2011/0104788 A1 | 5/2011 | Baker et al. |
| 2011/0189234 A1 | 8/2011 | Van Beusechem et al. |
| 2011/0256524 A1 | 10/2011 | Lee et al. |
| 2011/0275093 A1 | 11/2011 | Holm |
| 2011/0286999 A1 | 11/2011 | Holm |
| 2012/0020924 A1 | 1/2012 | Nakai et al. |
| 2012/0039877 A1 | 2/2012 | Holm |
| 2012/0207711 A1 | 8/2012 | Fueyo et al. |
| 2013/0058897 A1 | 3/2013 | Lee et al. |
| 2013/0101557 A1 | 4/2013 | Yun et al. |
| 2013/0231267 A1 | 9/2013 | O'Shea et al. |
| 2013/0243729 A1 | 9/2013 | O'Shea et al. |
| 2013/0243731 A1 | 9/2013 | Dias et al. |
| 2013/0323205 A1 | 12/2013 | Diaconu et al. |
| 2013/0345295 A1 | 12/2013 | Wang et al. |
| 2014/0023619 A1 | 1/2014 | Kosai et al. |
| 2014/0199688 A1 | 7/2014 | Mizuguchi et al. |
| 2014/0294890 A1 | 10/2014 | Ketner et al. |
| 2014/0341857 A1 | 11/2014 | Bressy et al. |
| 2014/0348791 A1 | 11/2014 | Barouch et al. |
| 2014/0377294 A1 | 12/2014 | Fueyo-Margareto et al. |
| 2014/0377295 A1 | 12/2014 | Ertl et al. |
| 2015/0005397 A1 | 1/2015 | O'Shea et al. |
| 2015/0017127 A1 | 1/2015 | O'Shea et al. |
| 2015/0071881 A1 | 3/2015 | Bonastre et al. |
| 2015/0086579 A1 | 3/2015 | Mayall et al. |
| 2015/0202324 A1 | 7/2015 | Hemminki et al. |
| 2015/0232880 A1 | 8/2015 | Hemminki et al. |
| 2015/0246949 A1 | 9/2015 | Lieber et al. |
| 2015/0306160 A1 | 10/2015 | Fueyo et al. |
| 2015/0352203 A1 | 12/2015 | Wilson et al. |
| 2015/0374766 A1 | 12/2015 | O'Shea et al. |
| 2016/0017294 A1 | 1/2016 | Reid et al. |
| 2016/0051603 A1 | 2/2016 | Roy et al. |
| 2016/0053235 A1 | 2/2016 | O'Shea et al. |
| 2016/0082100 A1 | 3/2016 | Ranki et al. |
| 2016/0090574 A1 | 3/2016 | Fisher et al. |
| 2016/0102295 A1 | 4/2016 | Roy et al. |
| 2016/0143967 A1 | 5/2016 | Fueyo-Margareto et al. |
| 2016/0208287 A1 | 7/2016 | Hemminki et al. |
| 2016/0244783 A1 | 8/2016 | Roy et al. |
| 2016/0289645 A1 | 10/2016 | Tufaro et al. |
| 2017/0035818 A1 | 2/2017 | Seymour et al. |
| 2017/0073647 A1 | 3/2017 | Fisher et al. |
| 2017/0080069 A1 | 3/2017 | Cerullo et al. |
| 2017/0096646 A1 | 4/2017 | Roy et al. |
| 2017/0137786 A1 | 5/2017 | Hemminki et al. |
| 2017/0183636 A1 | 6/2017 | Roy et al. |
| 2017/0190752 A1 | 7/2017 | Holm |
| 2017/0202893 A1 | 7/2017 | O'Shea et al. |
| 2017/0252443 A1 | 9/2017 | Holm |
| 2017/0314044 A1 | 11/2017 | Davydova et al. |
| 2017/0348405 A1 | 12/2017 | Shiratsuchi et al. |
| 2018/0000966 A1 | 1/2018 | Dicks et al. |
| 2018/0051301 A1 | 2/2018 | Rentschler et al. |
| 2018/0072809 A1 | 3/2018 | Hemminki et al. |
| 2018/0100164 A1 | 4/2018 | Wei et al. |
| 2018/0100204 A1 | 4/2018 | O'Shea et al. |
| 2018/0104288 A1 | 4/2018 | Galili et al. |
| 2018/0147245 A1 | 5/2018 | O'Shea et al. |
| 2018/0163190 A1 | 6/2018 | Gerardy-Schahn et al. |
| 2018/0216081 A1 | 8/2018 | Colloca et al. |
| 2018/0221423 A1 | 8/2018 | O'Shea et al. |
| 2018/0318365 A1 | 11/2018 | Yeung et al. |
| 2018/0346929 A1 | 12/2018 | Kosai et al. |
| 2018/0355374 A1 | 12/2018 | O'Shea et al. |
| 2018/0355379 A1 | 12/2018 | O'Shea et al. |
| 2018/0369417 A1 | 12/2018 | Yun et al. |
| 2019/0055522 A1 | 2/2019 | Holm |
| 2019/0062395 A1 | 2/2019 | Merchant et al. |
| 2019/0070233 A1 | 3/2019 | Yeung et al. |
| 2019/0093085 A1 | 3/2019 | Tufaro et al. |
| 2019/0136204 A1 | 5/2019 | Reid et al. |
| 2019/0142967 A1 | 5/2019 | Hicklin et al. |

(56) References Cited

U.S. PATENT DOCUMENTS

| | | |
|---|---|---|
| 2019/0175716 A1 | 6/2019 | Gilbert et al. |
| 2019/0183946 A1 | 6/2019 | Bonastre et al. |
| 2019/0201462 A1 | 7/2019 | Tufaro et al. |
| 2019/0201551 A1 | 7/2019 | Curiel |
| 2019/0233845 A1 | 8/2019 | Maloveste et al. |
| 2019/0247452 A1 | 8/2019 | Lan et al. |
| 2019/0269794 A1 | 9/2019 | McVey et al. |
| 2019/0275092 A1 | 9/2019 | Tufaro et al. |
| 2019/0275093 A1 | 9/2019 | Aboody et al. |
| 2019/0300905 A1 | 10/2019 | Ammendola et al. |
| 2019/0314523 A1 | 10/2019 | O'Shea et al. |
| 2019/0314525 A1 | 10/2019 | O'Shea et al. |
| 2019/0345204 A1 | 11/2019 | Carrió et al. |
| 2019/0350992 A1 | 11/2019 | Cascallo Piqueras et al. |
| 2019/0352616 A1 | 11/2019 | Reid et al. |
| 2019/0352669 A1 | 11/2019 | Reid et al. |
| 2019/0374589 A1 | 12/2019 | Suzuki et al. |
| 2019/0388487 A1 | 12/2019 | Shayakhmetov et al. |
| 2020/0014798 A1 | 1/2020 | Hicklin et al. |
| 2020/0032223 A1 | 1/2020 | Reid et al. |
| 2020/0078415 A1 | 3/2020 | Reid et al. |
| 2020/0095560 A1 | 3/2020 | Holm |
| 2020/0102352 A1 | 4/2020 | Colloca et al. |
| 2020/0149014 A1 | 5/2020 | O'Shea et al. |
| 2020/0325492 A1 | 10/2020 | O'Shea et al. |
| 2021/0024587 A1 | 1/2021 | O'Shea et al. |
| 2022/0090123 A1 | 3/2022 | O'Shea et al. |
| 2022/0096577 A1 | 3/2022 | O'Shea et al. |

FOREIGN PATENT DOCUMENTS

| | | |
|---|---|---|
| CN | 102191245 A | 9/2011 |
| EP | 689447 | 4/1999 |
| EP | 931830 | 3/2001 |
| EP | 760675 | 8/2001 |
| EP | 1167533 | 1/2002 |
| EP | 1284294 | 2/2003 |
| EP | 1413586 | 4/2004 |
| EP | 851769 | 2/2005 |
| EP | 861329 | 3/2005 |
| EP | 1181382 | 3/2005 |
| EP | 1121137 | 7/2005 |
| EP | 991763 | 9/2005 |
| EP | 1294918 | 10/2005 |
| EP | 889969 | 11/2005 |
| EP | 1498129 | 11/2005 |
| EP | 1593742 | 11/2005 |
| EP | 920524 | 12/2005 |
| EP | 1307573 | 1/2006 |
| EP | 978566 | 5/2006 |
| EP | 778889 | 7/2006 |
| EP | 1070118 | 10/2006 |
| EP | 1214098 | 11/2006 |
| EP | 1230378 | 6/2007 |
| EP | 1550722 | 6/2007 |
| EP | 863987 | 1/2008 |
| EP | 920514 | 1/2008 |
| EP | 1159438 | 7/2008 |
| EP | 1266022 | 10/2008 |
| EP | 1678193 | 12/2008 |
| EP | 1054064 | 12/2009 |
| EP | 2012822 | 1/2010 |
| EP | 1816204 | 10/2010 |
| EP | 1749098 | 12/2010 |
| EP | 1799836 | 12/2010 |
| EP | 1816205 | 8/2011 |
| EP | 1818408 | 8/2011 |
| EP | 1409748 | 10/2011 |
| EP | 1180932 | 1/2012 |
| EP | 1466001 | 4/2012 |
| EP | 1743041 | 6/2012 |
| EP | 1446479 | 8/2012 |
| EP | 1649028 | 8/2012 |
| EP | 1990418 | 8/2012 |
| EP | 2311499 | 8/2012 |
| EP | 1636370 | 4/2014 |
| EP | 1767642 | 4/2014 |
| EP | 2350269 | 9/2015 |
| EP | 2403951 | 9/2015 |
| EP | 2643465 | 5/2016 |
| EP | 2428229 | 8/2016 |
| EP | 2459716 | 8/2016 |
| EP | 2220241 | 9/2016 |
| EP | 2325298 | 10/2016 |
| EP | 2379586 | 11/2016 |
| EP | 2220242 | 12/2016 |
| EP | 2774985 | 12/2016 |
| EP | 2163260 | 3/2017 |
| EP | 2580234 | 3/2017 |
| EP | 2798069 | 3/2017 |
| EP | 2855685 | 3/2017 |
| EP | 2900818 | 6/2017 |
| EP | 2301582 | 7/2017 |
| EP | 3049520 | 7/2017 |
| EP | 1453543 | 8/2017 |
| EP | 2463362 | 11/2017 |
| EP | 2558481 | 12/2017 |
| EP | 2682459 | 12/2017 |
| EP | 2714916 | 1/2018 |
| EP | 2391638 | 6/2018 |
| EP | 2563919 | 6/2018 |
| EP | 2971008 | 7/2018 |
| EP | 2606137 | 8/2018 |
| EP | 2855669 | 10/2018 |
| EP | 2986311 | 11/2018 |
| EP | 3145537 | 12/2018 |
| EP | 2654786 | 2/2019 |
| EP | 3280798 | 6/2019 |
| EP | 3029144 | 7/2019 |
| EP | 3150706 | 7/2019 |
| EP | 2809788 | 9/2019 |
| EP | 3071697 | 10/2019 |
| EP | 3274363 | 10/2019 |
| EP | 3460052 | 10/2019 |
| JP | 2005-525779 | 9/2005 |
| JP | 2008-517627 | 5/2008 |
| JP | 2010-527324 | 8/2010 |
| JP | 2011-524904 | 9/2011 |
| WO | WO 96/18418 | 6/1996 |
| WO | WO 98/55641 | 12/1998 |
| WO | WO 1998/054346 | 12/1998 |
| WO | WO 1999/044423 | 9/1999 |
| WO | WO 00/03029 | 1/2000 |
| WO | WO 00/22137 | 4/2000 |
| WO | WO 2000/042208 | 7/2000 |
| WO | WO 01/004282 | 1/2001 |
| WO | WO 2001/002431 | 1/2001 |
| WO | WO 2001/021217 | 3/2001 |
| WO | WO 2001/023004 | 4/2001 |
| WO | WO 01/90392 | 11/2001 |
| WO | WO 2001/098513 | 12/2001 |
| WO | WO 02/46372 | 6/2002 |
| WO | WO 03/064666 | 8/2003 |
| WO | WO 03/076605 | 9/2003 |
| WO | WO 2003/092579 | 11/2003 |
| WO | WO 03/104467 | 12/2003 |
| WO | WO 2004/018627 | 3/2004 |
| WO | WO 2004/031357 | 4/2004 |
| WO | WO 2005/001103 | 1/2005 |
| WO | WO 2005/010149 | 2/2005 |
| WO | WO 2005/023848 | 3/2005 |
| WO | WO 2005/030261 | 4/2005 |
| WO | WO 2005/065348 | 7/2005 |
| WO | WO 2005/075506 | 8/2005 |
| WO | WO 2005/107474 | 11/2005 |
| WO | WO 2005/113781 | 12/2005 |
| WO | WO 2005/117993 | 12/2005 |
| WO | WO 2006/086357 | 8/2006 |
| WO | WO 2006/119449 | 11/2006 |
| WO | WO 2007/124065 | 11/2007 |
| WO | WO 2008/095168 | 8/2008 |
| WO | WO 2008/150496 | 12/2008 |
| WO | WO 2009/065800 | 5/2009 |
| WO | WO 2010/024483 | 3/2010 |

(56) References Cited

FOREIGN PATENT DOCUMENTS

| WO | WO 2010/037027 | 4/2010 |
| WO | WO 2011/133040 | 10/2011 |
| WO | WO 2012/003287 | 1/2012 |
| WO | WO 2012/022496 | 2/2012 |
| WO | WO 2012-024350 | 2/2012 |
| WO | WO 2012/024351 | 2/2012 |
| WO | WO 2012/038606 | 3/2012 |
| WO | WO 2012/083297 | 6/2012 |
| WO | WO 2013/036791 | 3/2013 |
| WO | WO 2013/135615 | 9/2013 |
| WO | WO 2013/138505 | 9/2013 |
| WO | WO 2014/000026 | 1/2014 |
| WO | WO 2014/153204 | 9/2014 |
| WO | WO 2014/170389 | 10/2014 |
| WO | WO 2015/155370 | 10/2015 |
| WO | WO 2016/049201 | 3/2016 |
| WO | WO 2017/062511 | 4/2017 |
| WO | WO 2017/147265 | 8/2017 |
| WO | WO 2017/147269 | 8/2017 |
| WO | WO 2018/078220 | 5/2018 |
| WO | WO 2018/083257 | 5/2018 |
| WO | WO 2018/083258 | 5/2018 |
| WO | WO 2018/083259 | 5/2018 |
| WO | WO 2018/104919 | 6/2018 |
| WO | WO 2018/201017 | 11/2018 |
| WO | WO 2018/204677 | 11/2018 |
| WO | WO 2018/218083 | 11/2018 |
| WO | WO 2019/016756 | 1/2019 |
| WO | WO 2019/057745 | 3/2019 |
| WO | WO 2019/073059 | 4/2019 |
| WO | WO 2019/086450 | 5/2019 |
| WO | WO 2019/086456 | 5/2019 |
| WO | WO 2019/086461 | 5/2019 |
| WO | WO 2019/086466 | 5/2019 |
| WO | WO 2019/158914 | 8/2019 |
| WO | WO 2019/179977 | 9/2019 |
| WO | WO 2019/179979 | 9/2019 |
| WO | WO 2019/191494 | 10/2019 |
| WO | WO 2019/199859 | 10/2019 |
| WO | WO 2019/202118 | 10/2019 |
| WO | WO 2019/239311 | 12/2019 |
| WO | WO 2020/014539 | 1/2020 |
| WO | WO 2020/046130 | 3/2020 |
| WO | WO 2020/076820 | 4/2020 |

OTHER PUBLICATIONS

Zhang et al, In vitro and in vivo experimental models for cancer immunotherapy study, Current Research in Biotechnology, 2024, pp. 1-11.*
Ji et al., "Oncolytic Adenoviruses Delivering Herpes Simplex Virus Thymidine Kinase Suicide Gene Reduces the Growth of Human Retinoblastoma in an in vivo Mouse Model," *Experimental Eye Res.*, 89:193-199, 2009.
Kubo et al., "Complete Regression of Human Malignant Mesothelioma Xenografts Following Local Injection of Midkine Promoter-Driven Oncolytic Adenovirus," *J. Gene Med.*, 12:681-692, 2010.
Loskog, "Immunostimulatory Gene Therapy Using Oncolytic Viruses as Vehicles," *Viruses*, 7:5780-5791, 2015.
Fukazawa et al., "Adenovirus-mediated cancer gene therapy and virotherapy (review)," *Int J Mol Med*, vol. 25:3-10, 2010.
Hibma et al., "Increased apoptosis and reduced replication efficiency of the E3 region-modified dl309 adenovirus in cancer cells," *Virus Res* 145:112-120, 2009.
Cho et al., "Efficacy of CD46-targeting chimeric Ad5/35 adenoviral gene therapy for colorectal cancers," *Oncotarget* 7(25):38210-38223, 2016.
Hoffman and Wildner, "Comparison on herpes simplex virus- and conditionally replicative adenovirus-based vectors for glioblastoma treatment," *Cancer Gene Ther* 14:627-639, 2007.
Ishii and Ochiai, "The origin of fibroblast recruited into cancer-induced stromal tissue," Kenbikyo 43(2):104-108, 2008 (in Japanese with English abstract).

Raki et al., "Utility of TK/GCV in the context of highly effective oncolysis mediated by a serotype 3 receptor targeted oncolytic adenovirus," *Gene Ther* 14:1380-1388, 2007.
Alba et al., "Gutless adenovirus: last-generation adenovirus for gene therapy," Gene Ther 12:S18-S27, 2005.
Alba et al., "Identification of coagulation factor (F)X binding sites on the adenovirus serotype 5 hexon: effect of mutagenesis on FX interactions and gene transfer," Blood 114(5): 965-971, 2009.
Alonso et al., "Combination of the oncolytic adenovirus ICOVIR-5 with chemotherapy provides enhanced anti-glioma effect in vivo," *Cancer Gene Ther* 14:756-761, 2007.
Barton, et al., "Second-Generation Replication-Competent Oncolytic Adenovirus Armed with Improved Suicide Genes and ADP Gene Demonstrates Greater Efficacy without Increased Toxicity", Molecular Therapy, 2006, 13(2):347-356.
Batzer et al., "Enhanced evolutionary PCR using oligonucleotides with inosine at the 3'-terminus", Nucleic Acid Research, 1991, 19(18):5081.
Bauerschmitz et al., "Tissue-Specific Promoters Active in CD44$^+$ CD24$^{-/low}$ Breast Cancer Cells," *Cancer Res* 68(14):5533-5539, 2008.
Bayle et al., "Rapamycin Analogs with Differential Binding Specificity Permit Orthogonal Control of Protein Activity," Chem Biol 13:99-107, 2006.
Behar et al., "Llama Single-Domain Antibodies Directed against Nonconventional Epitopes of Tumor-Associated Carcinoembryonic Antigen Absent from Nonspecific Cross-Reacting Antigen," FEBS J., vol. 276:3881-3893, 2009.
Belousova et al., "Modulation of Adenovirus Vector Tropism via Incorporation of Polypeptide Ligands into the Fiber Protein," J Virol 76(17):8621-8631, 2002.
Berge et al., "Pharmaceutical Salts", Journal of Pharmaceutical Science, 1977, 66: 1-19.
Bett et al., "DNA sequence of the deletion/insertion in early region 3 of Ad5 dl309," *Virus Res* 39: 75-82, 1995.
Bradshaw et al., "Biodistribution and inflammatory profiles of novel penton and hexon double-mutant serotype 5 adenoviruses," *J Control Release* 164(3): 394-402, 2012.
Bremnes et al., "The Role of Tumor Stroma in Cancer Progression and Prognosis," J. Thorac. Oneal., vol. 6:209-217, 2011.
Card et al., "MicroRNA silencing improves the tumor specificity of adenoviral transgene expression," *Cancer Gene Ther* 19: 451-459, 2012.
Chen et al., "Identification of an 11-kDa FKBP12-rapamycin-binding domain within the 289-kDa FKBP12-rapamycin-associated protein and characterization of a critical serine residue," Proc Natl Acad Sci USA 92:4947-4951, 1995.
Cheo et al., "Concerted Assembly and Cloning of Multiple DNA Segments Using In Vitro Site-Specific Recombination: Functional Analysis of Multi-Segment Expression Clones," Genome Res 14:2111-2120, 2004.
Chong et al., "A System for Small-Molecule Control of Conditionally Replication-Competent Adenoviral Vectors," Mal Ther 5(2):195-203, 2002.
Chopra, "Recombinant Adenovirus with Enhanced Green Fluorescent Protein," Molecular Imaging and Contrast Agent Database (MICAD), Bethesda, MD: National Center for Biotechnology Information (US) (2004-2013): (Dec. 9, 2007, updated Jan. 2, 2008), 5 pp.
Doronin et al., "Tumor-Specific, Replication-Competent Adenovirus Vectors Overexpressing the Adenovirus Death Protein," *J. Virol.*, vol. 74:6147-6155, 2000.
Doronin et al., "Overexpression of ADP (E3-11.6K) Protein Increases Cell Lysis and Spread of Adenovirus," *Virol.*, 305: 378-387, 2003.
Evans, J.D. & Hearing, P., "Relocalization of the Mre11-Rad50-Nbs1 Complex by the Adenovirus E4 ORF3 Protein is Required for Viral Replication", *J. Virol.*, 2005, 79(10):6207-6215.
Fang et al., "An Antibody Delivery System for Regulated Expression of Therapeutic Levels of Monoclonal Antibodies In Vivo," Mal. Ther., vol. 15:1153-1159, 2007.

(56)          References Cited

OTHER PUBLICATIONS

Finke et al., "Tracking Fluorescence-Labeled Rabies Virus: Enhanced Green Fluorescent Protein-Tagged Phosphoprotein P Supports Virus Gene Expression and Formation of Infectious Particles," J. Viral., vol. 78(22): 12333-12343, 2004.

Frese et al., "Selective PDZ protein-dependent stimulation of phosphatidylinositol 3-kinase by the adenovirus E4-ORF1 oncoprotein," Oncogene 22: 710-721, 2003.

Fuerer and Iggo, "Adenoviruses with Tcf binding sites in multiple early promoters show enhanced selectivity for tumour cells with constitutive activation of the wnt signalling pathway," Gene Ther 9:270-281, 2002.

Funston et al., "Expression of heterologous genes in oncolytic adenoviruses using picornaviral 2A sequences that trigger ribosome skipping," J Gen Viral 89:389-396, 2008.

Gall et al., "Construction and Characterization of Hexon-Chimeric Adenoviruses: Specification of Adenovirus Serotype," J Virol 72(12): 10260-10264, 1998.

Gibson et al., "Enzymatic Assembly of DNA Molecules up to Several Hundred Kilobases," Nature Meth., vol. 6:343-360, 2009.

Glasgow et al., "A Strategy for Adenovirus Vector Targeting with a Secreted Single Chain Antibody," PLoS One, vol. 4:e8355, 2009.

Havenga et al., "Novel Replication-Incompetent Adenoviral B-group Vectors: High Vector Stability and Yield in PER.C6 Cells," J. Gen. Virol., vol. 87:2135-2143, 2006.

Hawkins et al., "Gene delivery from the E3 region of replicating human adenovirus: evaluation of the E3B region," Gene Therapy 8, 1142-1148, 2001.

Heise et al., "An Adenovirus E1A Mutant that Demonstrates Potent and Selective Systemic Anti-Tumoral Efficacy," Nat Med. 6: 1134-1139, 2000.

Helin et al., "Heterodimerization of the Transcription Factors E2F-1 and DP-1 is required for Binding to the Adenovirus E4 (ORF6/7) Protein," J Virol 68: 5027-5035, 1994.

Henikoff, S. & Henikoff, J.G., "Amino acid substitution matrices from protein blocks", Proc. Natl. Acad. Sci. USA, 1992, 89:10915-10919.

Hernandez-Aya, L. F. et al. "Targeting the Phosphatidylinositol 3-Kinase Signaling Pathway in Breast Cancer", The Oncologist, 16, pp. 404-414, 2011.

Holm et al., "Multidrug-resistance Cancer Cells Facilitate E1-independent Adenovirus Replication: Impact for Cancer Gene Therapy," Cancer Res 64:322-328, 2004.

Javier, "Cell polarity proteins: common targets for tumorigenic human viruses," Oncogene 27:7031-7046, 2008.

Johnson et al., "Selectively replicating adenoviruses targeting deregulated E2F activity are potent, systemic antitumor agents," Cancer Cell 1:325-337, 2002.

Ketzer et al., "Synthetic riboswitches for external regulation of genes transferred by replication-deficient and oncolytic adenoviruses," Nucleic Acids Res 40(21):el67 (10 pages), 2012.

Kim et al., "High Cleavage Efficiency of a 2A Peptide Derived from Porcine Teschovirus-1 in Human Cell Lines, Zebrafish and Mice," PLoS One, vol. 64:e18556, 2011.

Kirn, D., "Clinical research results with dl1520 (Onyx-015, a replication-selective adenovirus for the treatment of cancer: what have we learned?", Gene Therapy, 2001, 8(2):89-98.

Kovesdi et al., "Role of an Adenovirus E2 Promoter Binding Factor in E1A Mediated Coordinate Gene Control," Proc Nat Acad Sci USA 84: 2180-2184, 1987.

Leicher et al., "Coexpression of the KCNA3B Gene Product with Kv1 .5 Leads to a Novel A-type Potassium Channel", The Journal of Biological Chemistry, 1998, 273(52):35095-35101.

Leppard et al., "Adenovirus type 5 E4 Orf3 protein targets promyelocytic leukaemia (PML) protein nuclear domains for disruption via a sequence in PML isoform II that is predicted as protein as a protein interaction site of bioinformatics anaylsis", J. Gen. Virol., 2009, 90(1):95-104.

Li and Elledge "Harnessing homologous recombination in vitro to generate recombinant DNA via SLIC," Nat Methods 4(3):251-256, 2007.

Liu et al., "Oncolytic Adenoviral Vector Carrying the Cytosine Deaminase Gene for Melanoma Gene Therapy," Cancer Gene Ther., vol. 13:845-855, 2006.

Lopez et al., "A Tumor-stroma Targeted Oncolytic Adenovirus Replicated in Human Ovary Cancer Samples and Inhibited Growth of Disseminated Solid Tumors in Mice," Mol Ther 20(12):2222-2233, 2012.

McCormick, "Cancer Gene Therapy: Fringe or Cutting Edge?," Nature Rev. Cancer, vol. 1:130-141, 2001.

Minskaia and Ryan, "Protein Coexpression Using FMDV 2A: Effect of "Linker" Residues," BioMed Research International, vol. 2013, 12 pp.

Mohr, "To replicate or not to replicate: achieving selective oncolytic virus replication in cancer cells through translational control," Oncogene, vol. 24:7697-7709, 2005.

Murakami et al., "Chimeric Adenoviral Vectors Incorporating a Fiber of Human Adenovirus 3 Efficiently Mediate Gene Transfer into Prostrate Cancer Cells," The Prostate, vol. 70:362-376, 2009.

NCBI Accession No. CVI 10986, Jan. 11, 2011, 3 pages.

Nevels et al., "The adenovirus E4orf6 protein can promote E1A/E1B-induced focus formation by interfering with p53 tumor suppressor function," Proc Natl Acad Sci USA 94:1206-1211, 1997.

Ono et al., "Noninvasive Visualization of Adenovirus Replication with a Fluorescent Reporter in the E3 Region," Cancer Res., vol. 65: 10154-10158, 2005.

O'Shea et al., "Adenovirus Overrides Cellular Checkpoints for Protein Translation," Cell Cycle 4(7):883-888, 2005.

O'Shea et al., "Adenoviral proteins mimic nutrient/growth signals to activate the mTOR pathway for viral replication," EMBO J 24:1211-1221, 2005.

O'Shea et al., "DNA Tumor Viruses—the Spies who Lyse US," Curr Opin Genet Dev 15:18-26, 2005.

O'Shea et al., "Viruses—seeking and destroying the tumor program," Oncogene 24: 7640-7655, 2005.

Pearson, W. R. & Lipman, D.J., "Improved tools for biological sequence comparison", Proc. Nat'/. Acad. Sci. USA, 1988, 85:2444-2448.

Pelka et al., "Adenovirus E1A Directly Targets the E2F/DP-1 Complex," J Virol 85(17):8841-8851, 2011.

Rossolini et al., "Use of deoxyinosine-containing primers vs degenerate primers for polymerase chain reaction based on ambiguous sequence information", Mo/. Cell. Probes, 1994, 8:91-98.

Roy et al., "Rescue of chimeric adenoviral vectors to expand the serotype repertoire," J Viral Methods 14:41-21, 2007.

Shapiro et al., "Recombinant Adenoviral Vectors can Induce Expression of p73 via the E4-orf6/7 Protein," J Virol 80(11):5349-5360, 2006.

Shepard and Omelles, "E4orf13 is Necessary for Enhanced S-Phase Replication of Cell Cycle-Restricted Subgroup C Adenoviruses," J Virol 77(15):8593-8595, 2003.

Smith T.F., & Waterman, M.S., "Comparison of Biosequences", Advances in Applied Mathematics, 1981, 2:482-489.

Soria et al., "Heterochromatin silencing of p53 target genes by a small viral protein", Nature, 2010, 466(7310):1076-1083.

Stanton et al. "Re-engineering adenovirus vector systems to enable high-throughput analyses of gene function" Bio Techniques 45: 659-668 (Dec. 2008) doi 10.2144/000112993 (Year: 2008).

Szymczak et al., "Correction of Multi-Gene Deficiency in vivo using a Single 'self-cleaving' 2A Peptide-Based Retroviral Vector," Nature Biotech., vol. 22:589-594, 2004.

Tan et al., "Coexpression of double or triple copies of the rabies virus glycoprotein gene using a 'self-cleaving' 2A peptide-based replication-defective human adenovirus serotype 5 vector," Biologicals, vol. 38:586-593, 2010.

Ullman et al., "Adenovirus E4 ORF3 Protein Inhibits the Interferon-Mediated Antiviral Response", Journal of Virology, 2007, 81(9):4744-4752.

Verheije et al., "Retargeting of Viruses to Generate Oncolytic Agents," Adv. Viral., vol. 2012:1-15, 2012.

(56)                    References Cited

OTHER PUBLICATIONS

Volk et al., "Enhanced Adenovirus Infection of Melanoma Cells by Fiber Modification," Cancer Biol Ther 2(5): 511-515, 2003.

Wachler et al., "Engineering targeted viral vectors for gene therapy," Nat Rev Genet 8(8):573-587, 2007.

Wang et al., "Identification of Specific Adenovirus E1A N-Terminal Residues Critical to the Binding of Cellular Proteins and to the Control of Cell Growth," J. Virol., vol. 67:476-488, 1993.

Warram et al., "A Genetic Strategy for Combined Screening and Localized Imaging of Breast Cancer," Mal Imaging Biol 13:452-461, 2011.

Whyte et al., "Association between an Oncogene and an Anti-Oncogene: the Adenovirus E1A Proteins Bind to the Retinoblastoma Gene Product," *Nature* 334: 124-129, 1988.

Yaghoubi et al., "Positron Emission Tomography Reporter Genes and Reporter Probes: Gene and Cell Therapy Applications," Theranostics, vol. 2:374-391, 2012.

Yount et al., "Strategy for Systematic Assembly of Large RNA and DNA Genomes: Transmissible Gastroenteritis Virus Model," J. Viral., vol. 74: 10600-10611, 2000.

Dias et al., "Targeted cancer immunotherapy with oncolytic adenovirus coding for a fully human monoclonal antibody specific for CTLA-4," *Gene Therapy*, vol. 19:988-998, 2012.

Kurihara et al., "Selectivity of a replication-competent adenovirus for human breast carcinoma cells expressing the MUC1 antigen," *J. Clin. Invest.*, vol. 106:763-771, 2000.

Fueyo et al., "A mutant oncolytic adenovirus targeting the Rb pathway produces anti-glioma effect in vivo," *Oncogene* 19:2-12, 2000.

Li, "Self-Cleaving Fusion Tags for Recombinant Protein Production," *Biotechnol. Lett.*, vol. 33:869-881, 2011.

Wu et al., "The application of intein in the research of membrane protein," *Chemistry of Life* 35(2):200-205, 2015, abstract only.

Shimizu et al., "Development of a Novel Adenovirus Vector Exhibiting MicroRNA-mediated Suppression of the Leaky Expression of Adenovirus Genes," Yakugaku Zasshi, vol. 132:1407-1412, 2012 (in Japanese) (English abstract).

Suzuki et al., "miR-122A-Regulated Expression of a Suicide Gene Prevents Hepatotoxicity Without Altering Antitumor Effects in Suicide Gene Therapy," *Mol. Ther.*, vol. 16:1719-1726, 2008.

Le et al., "Dynamic Monitoring of Oncolytic Adenovirus In Vivo by Genetic Capsid Labeling," *J Natl Cancer Inst* 98(3):203-214, 2006.

Danthinne et al., "Production of first generation adenovirus vectors: a review," *Gene Ther.*, vol. 7:1707-1714, 2000.

Gao et al., "High throughput creation of recombinant adenovirus vectors by direct cloning, green-white selection and I-Sce I-mediated rescue of circular adenovirus plasmids in 293 cells," Gene Ther., vol. 10:1926-1930, 2003.

* cited by examiner

FIG. 3

Cell viability of infected quiescent SAEC, 7 d.p.i.

- Ad-102
- Ad-181
- Ad-189
- Ad-210
- ONYX-838 (E1A ΔCR2)
- Mock (ΔE1)

Cell viability of infected confluent A549, 7 d.p.i.

MOI 0.1          MOI 1          MOI 10

AdSyn-CO182
18 hpi

AdSyn-CO183
18 hpi

ONCOLYTIC ADENOVIRUS COMPOSITIONS

CROSS-REFERENCE TO RELATED APPLICATIONS

This application is a divisional of U.S. application Ser. No. 14/852,981, filed Sep. 14, 2015, issued as U.S. Pat. No. 11,077,156 on Aug. 3, 2021, which is a continuation of International Application No. PCT/US2014/029587, filed Mar. 14, 2014, published in English under PCT Article 21(2), which claims the benefit of U.S. Provisional Application No. 61/782,932, filed Mar. 14, 2013. The above-listed applications are herein incorporated by reference in their entirety.

STATEMENT OF GOVERNMENT SUPPORT

This invention was made with government funding under Grant No. 5T32GM007240-35 awarded by the National Institutes of Health. The government has certain rights in the invention.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jun. 28, 2021, 101 KB, which is incorporated by reference herein.

BACKGROUND

Cancer is a complex, debilitating disease that accounts for more than half a million deaths each year. There is a profound need for more effective, selective and safe treatments for cancer. Existing treatments for this pervasive, life threatening disease, such as chemotherapy and surgery, rarely eliminate all malignant cells, and often exhibit deleterious side-effects that can outweigh therapeutic benefit.

One approach that has the potential to address many of the shortcomings of current cancer treatments is oncolytic adenoviral therapy (Pesonen, S. et al., *Molecular Pharmaceutics*, 8(1): p. 12-28 (2010)). Adenovirus (Ad) is a self-replicating biological machine. It consists of a linear double-stranded 36 kb DNA genome sheathed in a protein coat. Adenoviruses invade and hijack the cellular replicative machinery to reproduce and upon assembly induce lytic cell death to escape the cell and spread and invade surrounding cells. These very same cellular controls are targeted by mutations in cancer. This knowledge can be exploited to create synthetic viruses that act like guided missiles, specifically infecting and replicating in tumor cells and bursting them apart to release thousands of virus progeny that can seek out and destroy distant metastases while overcoming possible resistance. Thus, the goal of oncolytic virus design is to generate a virus that specifically replicates in cancer cells, but leave normal cells unharmed. However, there have been challenges in designing viruses that selectively replicate in cancer cells. Thus, there is a need for additional viruses that selectively replicate in cancer cells.

SUMMARY

Provided herein is an adenovirus comprising an E1A polypeptide comprising one or more modifications, an E4orf6/7 polypeptide comprising one or more modifications, or an E4orf1 polypeptide comprising one or more modifications or a combination thereof. Compositions and kits comprising the modified adenoviruses are also provided. Further, provided is a method of treating a proliferative disorder in a subject comprising administering to the subject an adenovirus comprising an E1A polypeptide comprising one or more modifications, an E4orf6/7 polypeptide comprising one or more modifications, or an E4orf1 polypeptide comprising one or more modifications or a combination thereof.

The details of one or more embodiments are set forth in the accompanying drawings and the description below. Other features, objects, and advantages will be apparent from the description and drawings, and from the claims.

DESCRIPTION OF DRAWINGS

Figure 3:
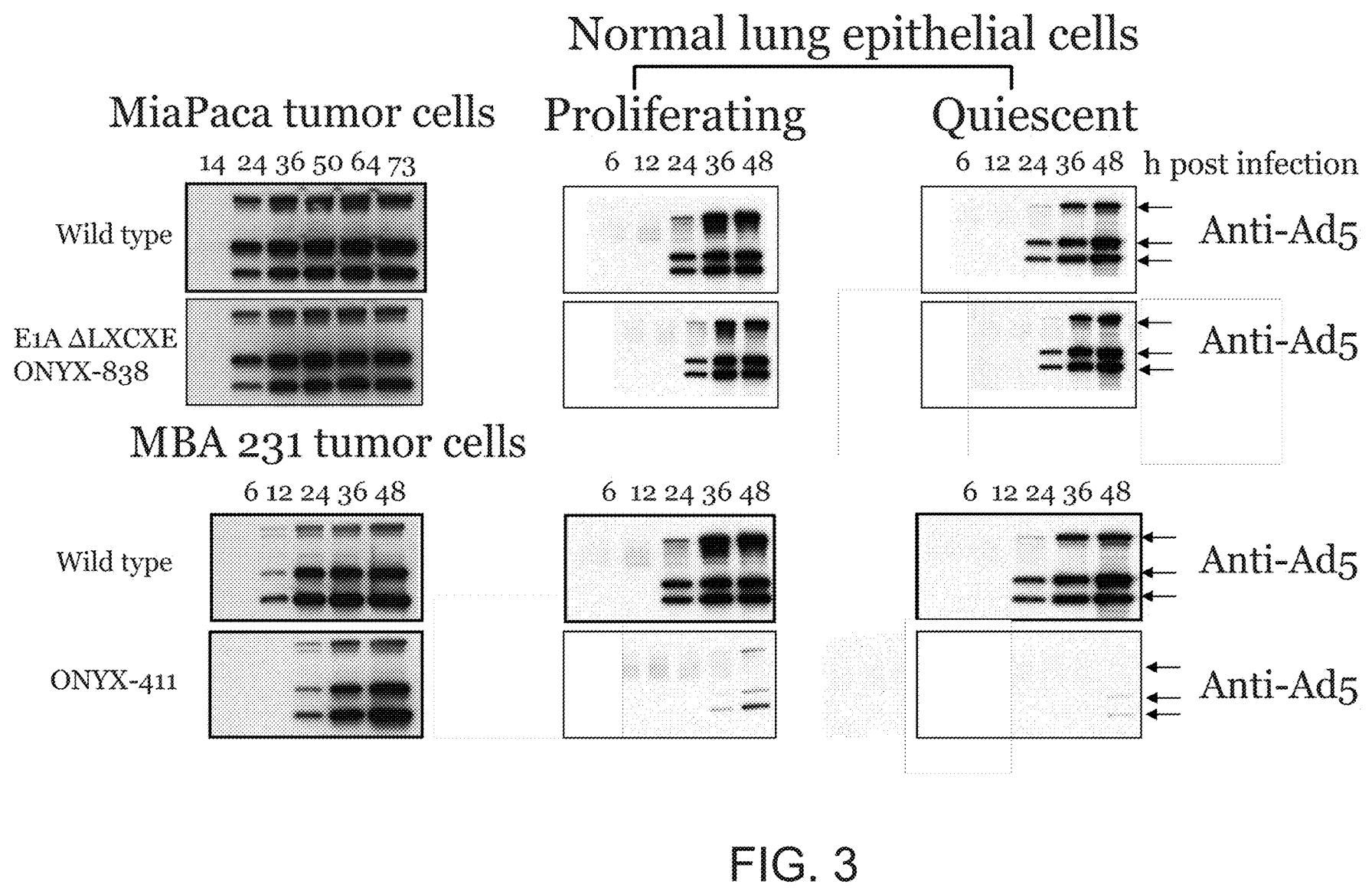

FIG. 3 shows images of immunoblots of cell lysates from infected primary small airway epithelial cells and tumor cells infected with wild type Ad5 and the "RB/p16/E2F pathway" selective viruses. Tumor and primary human cells were infected with either wild type virus, ONYX-838 (E1A ΔLXCXE) or ONYX-411 and harvested at various time points post infection. Lysates were analyzed for the expression of viral capsid proteins (anti-ad5, three bands comprise hexon, penton and fiber) which is a measure of viral replication. ONYX-838 indiscriminately replicates in tumor and primary lung epithelial cells. ONYX-411, which combines the E1A ΔLXCXE with cellular E2F control of adenovirus E1A, E1B and E4 regions (shown in FIG. 2) demonstrates selective-replication in tumor cells vs. normal cells (Johnson et al., *Cancer Cell* 1(4):325-337 (2002)). However, the E2F promoters result in recombination and also limit replication to wild type virus levels in tumor cells.

FIG. 4A shows common mutations that cause loss of Rb/p16 pathway tumor suppressor functions. FIG. 4B shows adenovirus proteins that directly deregulate Rb and E2F to drive the cell into S-phase.

FIG. 7A shows wild type E4 region. FIG. 7B shows resulting E4 ΔE4orf6/7 region.

As shown in FIG. 12A, compared to Ad-102 (AdSyn-CO102), Ad-181 (AdSyn-CO181) presents decreased cell-killing capability in SAEC. As shown in FIG. 12B, of the viruses that we have the data for, there is no defect in cell killing by mutant viruses relative to wild type.

FIG. 19 is a graph showing the cell viability of infected proliferating SAEC-hTERT cells after 9 days of infection. Cells were infected with a serial dilution of wt and mutant viruses (see Table 1 below). The metabolic activity was quantified by WST-1 assay (Roche, Basel, Switzerland). The viability of cells at three and ten infectious particles per cell show a separation of cell killing by viruses into two groups, less and more killing. The group of viruses that exhibit less killing bear both an E1A with an Rb-binding mutation and deletion of E4orf6/7. The group of viruses the exhibit more killing either have a wild type E1 or wild type E4.

FIG. 23 is a table showing the quantitation of cell viability assays for infected primary NHA, SAEC-hTERT (quiescent), SAEC-hTERT (proliferating), A549, MDA MB 231, and U87 cells shown in FIGS. 17-22.

DETAILED DESCRIPTION

Figure 1:
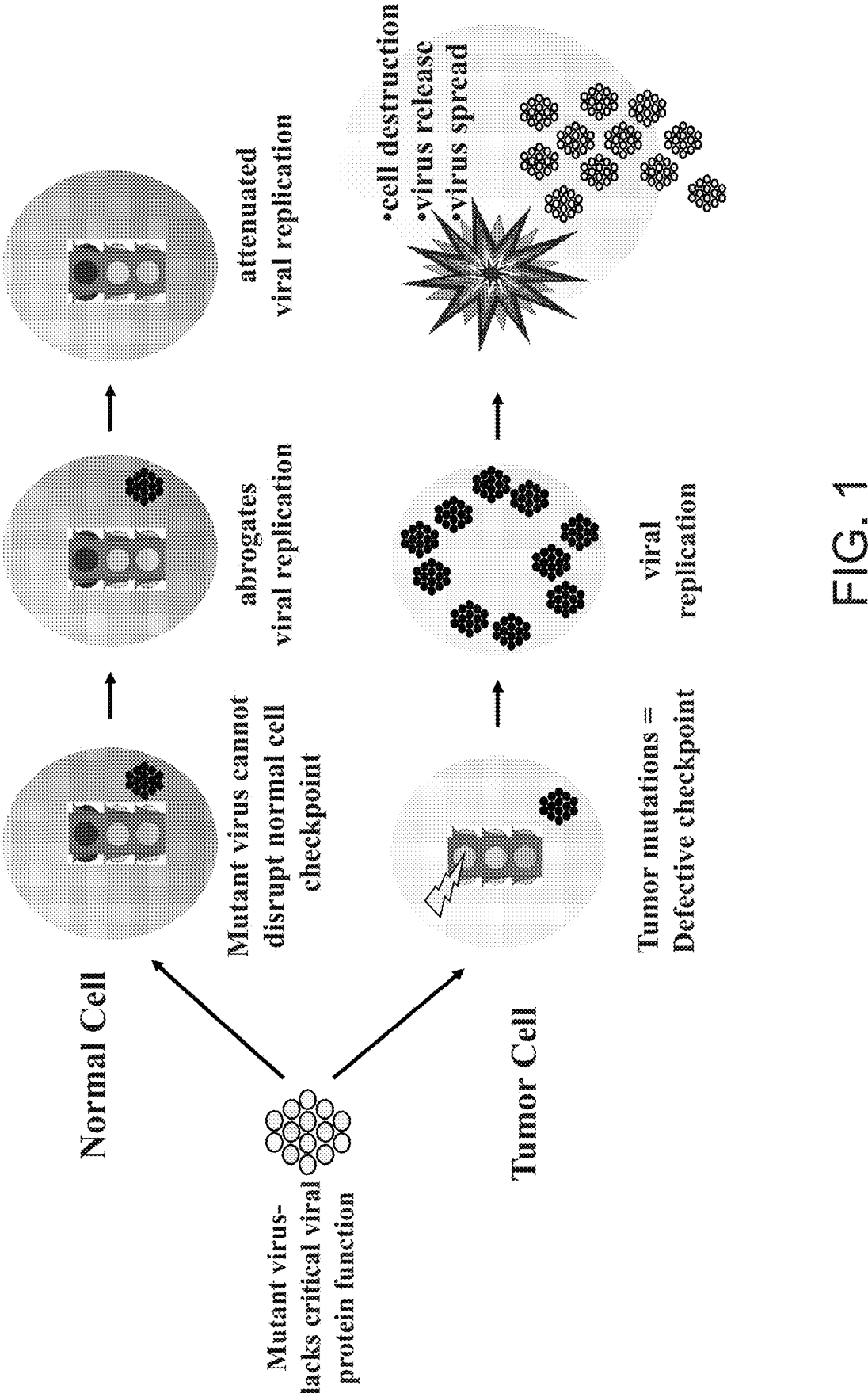
FIG. 1 is a schematic showing the general rationale of oncolytic viral cancer therapy.

The Rb/p16/E2F pathway is inactivated by mutations or through other mechanisms, e.g., viral mechanisms, in almost every form of human cancer. By way of example, the pathway can be inactivated through mutations in Rb, p107 mutations, p130 mutations, p16 mutations/epigenetic silencing, cyclin mutations and amplifications, CDK mutations and amplifications, mutations that downregulate cyclin dependent kinase inhibitors, mutations that upregulate E2F transcription factors and growth factor receptor pathway mutations (EGFR, RTKs, RAS, PI-3K, PTEN, RAF, MYC). However, most current chemotherapies are proliferative poisons that inhibit E2F transcriptional targets, but are also toxic to normal cells and have often devastating iatrogenic complications. Tumor mutations and small DNA virus' proteins converge in inactivating Rb. Studies with adenovirus E1A provided seminal insights into Rb and E2F. The original concept for an oncolytic adenovirus was an E1AΔLXCXE mutant but the agent is not selective, at least in primary cell cultures. E1A binds and inactivates Rb via a conserved (CR2) LXCXE motif (Whyte, et al., *Nature* 334(6178):124-9 (1988)), which activates E2F dependent transcription (Kovesdi et al., *PNAS* 84(8):2180-4 (1987)). This is thought to be the mechanism through which E1A activates E2F, diving expression of cellular and viral genes required for cellular and viral genome replication. Therefore, it was proposed that an adenovirus E1AΔCR2 mutant would selectively replicate in tumor cells that had mutations in the Rb/p16 tumor suppressor pathway (Heise et al., *Nat. Med.* 6(10):1134-9 (2000)). However, surprisingly, an E1AΔCR2 viral mutant still activates E2F and replicates in primary human epithelial cells (Johnson et al., *Cancer Cell* 1(4):325-337 (2002)). As described herein, it has been discovered that adenoviruses encode an additional viral protein, E4orf6/7, that activates E2F independently of E1A. Previous studies had shown that E4orf6/7 binds to E2F and DP1 to activate the transcription of viral E2 promoters (Helin and Harlow, *J. Virol.* 68(8):5027-5035 (1994)). Given that an E1A CR2 mutant still activates E2F and replicates in primary cells, it was hypothesized that E4orf6/7 activates E2F dependent cellular targets to drive S phase entry and viral replication, independently of E1A. Therefore, to design a virus that selectively replicates in tumor versus normal cells, adenoviruses were designed with mutations in both E1A and E4orf6/7. Therefore, as described in the example below, it was explored if a novel virus with E1AΔCR2 and/or ΔE4orf6/7 compound mutations would undergo selective lytic replication in tumor versus normal cells. In contrast to wild type and E1AΔCR2 viruses, E1AΔCR2/ΔE4orf6/7 and also ΔE4orf6/7 viruses replicate poorly in primary cells as evidenced by lack of capsid protein expression, failure to induce the E2F target genes-Cyclin A and B, failure to elicit S phase entry and viral replication. In contrast, these viruses replicate to wild type (WT) virus levels in A549 cells and a panel of tumor cell-lines. Therefore, the provided adenoviruses are selective cancer therapeutic agents.

Provided herein is a new Rb/p16/E1F tumor selective oncolytic viral therapy. These viruses have the potential to be self-perpetuating, kill tumor cells through regulated cell death, and produce progeny that can spread not only within the tumor but also to metastatic sites.

Definitions

The term "adenovirus" as referred to herein indicates over 52 adenoviral subtypes isolated from humans, and as many from other mammals and birds. See, e.g., Strauss, "Adenovirus infections in humans," in The Adenoviruses, Ginsberg, ed., Plenum Press, New York, N.Y., pp. 451 596 (1984). The term "adenovirus" can be referred to herein with the abbreviation "Ad" followed by a number indicating serotype, e.g., Ad5. The term optionally applies to two human serotypes, Ad2 and Ad5. Exemplary nucleic acid sequences of these adenoviruses include, but are not limited to, Human Adenovirus 5 (SEQ ID NO: 7) and Human Adenovirus 2 (SEQ ID NO: 8).

The term "E1A" refers to the adenovirus early region 1A (E1A) gene and polypeptides expressed from the gene. The term "E1A polypeptide" refers to the polypeptides expressed from the E1A gene and the term includes E1A polypeptides produced by any of the adenovirus serotypes. By way of example, amino acid sequences of the E1A polypeptide can be found at least at GenBank Accession Nos. CAE01147.1, AP_000161.1 (SEQ ID NO: 1), and AP_000197.1 (SEQ ID NO: 2). The nucleic acids encoding these polypeptides can be found at least at GenBank Accession Nos. AC_000008.1 (SEQ ID NO: 7) and AC_000007.1 (SEQ ID NO: 8). Also provided are E1A polypeptides comprising 65%, 70%, 75%, 80%, 85%, 90%, 91%, 92%, 93%, 94%, 95%, 96%, 97%, 98%, 99%, or more sequence identity to SEQ ID NO: 1 or SEQ ID NO: 2. E1A polypeptides have a role in viral genome replication by driving cells into the cell cycle. A comparison of E1A sequences of various human and simian adenovirus serotypes has identified three regions of conserved amino acid homology. In Ad5, conserved region 1 (CR1) maps between amino acid residues 40-80 as compared to SEQ ID NO: 2, CR2 between amino acid residues 121-139 as compared to SEQ ID NO: 2, and CR3 between residues 140-188 as compared to SEQ ID NO: 2.

The term "E4orf1" refers to the adenovirus E4orf1 polypeptide produced from the E4 gene, which contains several open reading frames, of an adenovirus. The term "E4orf1 polypeptide" includes E4orf1 polypeptides produced by the E4 gene from any of the adenovirus serotypes. By way of example, amino acid sequences of the E4orf1 polypeptide can be found at least at GenBank Accession Nos. AP_000196.1 (SEQ ID NO: 5) and AP_000232.1 (SEQ ID NO: 6). The nucleic acids encoding these polypeptides can be found at least at GenBank Accession Nos. AC_000008.1 (SEQ ID NO: 7) and AC_000007.1 (SEQ ID NO: 8). Also provided are E4orf1 polypeptides comprising 65%, 70%, 75%, 80%, 85%, 90%, 91%, 92%, 93%, 94%, 95%, 96%, 97%, 98%, 99%, or more sequence identity to SEQ ID NO: 5 or SEQ ID NO: 6.

The term "E4orf6/7" refers to the adenovirus E4orf6/7 polypeptide produced from the E4 gene, which contains several open reading frames, of an adenovirus. The term "E4orf6/7 polypeptide" includes E4orf6/7 polypeptides produced by the E4 gene from any of the adenovirus serotypes. By way of example, amino acid sequences of the E4orf6/7 polypeptide can be found at least at GenBank Accession Nos. AP_000191.1 (SEQ ID NO: 3) and AP_000227.1 (SEQ ID NO: 4). The nucleic acids encoding these polypeptides can be found at least at GenBank Accession Nos. AC_000008.1 (SEQ ID NO: 7) and AC_000007.1 (SEQ ID NO: 8). Also provided are E4orf6/7 polypeptides comprising 65%, 70%, 75%, 80%, 85%, 90%, 91%, 92%, 93%, 94%, 95%, 96%, 97%, 98%, 99%, or more sequence identity to SEQ ID NO: 3 or SEQ ID NO: 4.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The term "recombinant" when used with reference, e.g., to a cell, virus, nucleic acid, protein, or vector, indicates that the cell, virus, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

The term "recombinant" when used with reference, e.g., to a cell, or nucleic acid, protein, or vector, indicates that the cell, nucleic acid, protein or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

As used herein, the term "modification" refers to a change in the sequence of a nucleic acid or polypeptide sequence. For example, amino acid sequence modifications typically fall into one or more of three classes: substitutional, insertional or deletional variants. Insertions include amino and/or carboxyl terminal fusions as well as intrasequence insertions of single or multiple amino acid residues. Deletions are characterized by the removal of one or more amino acid residues from the protein sequence. As used herein, the symbol Δ or delta refers to a deletion. For example, E1AΔLXCXE refers to an E1A polypeptide having a deletion of the LXCXE domain. Substitutional modifications are those in which at least one residue has been removed and a different residue inserted in its place. Amino acid substitutions are typically of single residues, but can occur at a number of different locations at once. Substitutions, deletions, insertions or any combination thereof may be combined to arrive at a final construct. These modifications can be prepared by modification of nucleotides in the DNA encoding the protein, thereby producing DNA encoding the modification. Techniques for making insertion, deletion and substitution mutations at predetermined sites in DNA having a known sequence are well known. Modification techniques can involve the use of recombinant DNA technology to manipulate the DNA sequence encoding one or more polypeptide regions. Optionally, modification techniques include, for example, recombination, M13 primer mutagenesis and PCR mutagenesis.

The terms "transfection," "transduction," "transfecting," or "transducing," can be used interchangeably and are defined as a process of introducing a nucleic acid molecule or a protein to a cell. Nucleic acids are introduced to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In some aspects, the nucleic acid molecules are introduced into a cell using an adenoviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

A "control" or "standard control" refers to a sample, measurement, or value that serves as a reference, usually a known reference, for comparison to a test sample, measurement, or value. For example, a test sample can be taken from a patient suspected of having a given disease (e.g. an autoimmune disease, inflammatory autoimmune disease, cancer, infectious disease, immune disease, or other disease) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. One of skill will recognize that standard controls can be designed for assessment of any number of parameters (e.g. RNA levels, protein levels, specific cell types, specific bodily fluids, specific tissues, synoviocytes, synovial fluid, synovial tissue, fibroblast-like synoviocytes, macrophage-like synoviocytes, etc).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

As used herein, the term "proliferative disorder" refers to any cellular disorder in which the cells proliferate more rapidly than normal tissue growth. A proliferative disorder includes, but is not limited to, cancer.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The $P_{388}$ leukemia model is widely accepted as being predictive of in vivo anti-leukemic activity. It is believed that a compound that tests positive in the $P_{388}$ assay will generally exhibit some level of anti-leukemic activity in vivo regardless of the type of leukemia being treated. Accordingly, the present application includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The terms "dose" and "dosage" are used interchangeably herein. A dose refers to the amount of active ingredient given to an individual at each administration. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

By "therapeutically effective dose or amount" as used herein is meant a dose that produces effects for which it is administered (e.g. treating or preventing a disease). The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present application contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present application contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Other pharmaceutically acceptable carriers known to those of skill in the art are suitable for compositions of the present application.

A "subject," "individual," or "patient," is used interchangeably herein, which refers to a vertebrate, preferably a mammal, more preferably a human. Mammals include, but are not limited to, murines, simians, humans, farm animals, sport animals, and pets. Tissues, cells and their progeny of a biological entity obtained in vitro or cultured in vitro are also encompassed.

As used herein, an "Rb-deficient" tumor or cell or "a tumor or cell having the phenotype of Rb-deficiency" is a tumor or cell in which the level of the tumor suppressor Rb is lower than that in a normal or control cell or in which the Rb pathway is disrupted or inactive. The terms "Rb pathway," or "Rb signaling pathway" refer to, at least in part, molecules that affect pRb activity including pRb/p107, E2F-

1/-2/-3, and G1 cyclin/cdk complexes. It will be appreciated that molecules not presently known may also come within this definition.

As used herein, an "oncolytic virus" is a virus that selectively kills cells of a proliferative disorder, e.g., cancer cells. Killing of the cancer cells can be detected by any method established in the art, such as determining viable cell count, cytopathic effect, apoptosis of die neoplastic cells, synthesis of viral proteins in the cancer cells (e.g., by metabolic labeling, Western analysis of viral proteins, or reverse transcription polymerase chain reaction of viral genes necessary for replication), or reduction in size of a tumor.

As used herein, the term "replication deficient virus" refers to a virus that preferentially inhibits cell proliferation, causes cell lysis, or induces apoptosis (collectively considered killing) in a predetermined cell population with a given phenotype (e.g., tumor cells responsive to molecules in the pRb signaling pathway) which supports virus replication. Such viruses are unable to or are limited in the ability to inhibit cell proliferation, cause cell lysis, induce apoptosis, or otherwise replicate in cells that do not have the predetermined cell phenotype.

Modified Adenoviruses

Provided herein are adenoviruses (Ads) comprising an E1A polypeptide comprising one or more modifications and/or comprising an E4orf6/7 polypeptide comprising one or more modifications. The adenoviruses optionally include an E4orf1 polypeptide comprising one or more modifications. Also provided herein are adenoviruses comprising an E1A polypeptide comprising one or more modifications and comprising an E4orf1 polypeptide comprising one or more modifications. Thus, provided are modified adenoviruses with modifications in E1A, E4orf1 and E4orf6/7. The provided modified adenoviruses are oncolytic. The provided modified adenoviruses also selectively replicate in cancer cells with deregulated E2F and normal cell cycle checkpoints. The provided modified adenoviruses selectively replicate in cells with an inactive Rb/p16 tumor suppressor pathway. The provided modified adenoviruses can include one or more further modifications including those described in International Publication Nos. WO 2012/024350 and WO 2013/138505, which are incorporated by reference herein in their entireties.

The term "modified adenovirus," refers to an adenovirus having a gene sequence that is not found in nature (e.g. non-wild-type adenovirus). Optionally, the modified adenovirus is a recombinant adenovirus. As used herein, the term "modified E1A," refers to an E1A polypeptide and/or the E1A gene or nucleic acid encoding the E1A polypeptide with one or more modifications in the polypeptide or nucleic acid sequence, respectively. As used herein, the term "modified E4orf1," refers to an E4orf1 polypeptide and/or the E1orf1 gene or nucleic acid encoding the E4orf1 polypeptide with one or more modifications in the polypeptide or nucleic acid sequence, respectively. As used herein, the term "modified E4orf6/7," refers to the E4orf6/7 polypeptide and/or the E4orf6/7 gene or nucleic acid encoding the E4orf6/7 polypeptide with one or more modifications in the polypeptide or nucleic acid sequence, respectively.

The term "Rb/p16/E2F replication impaired or deficient," as used herein, means that, upon infection of a cell, adenovirus replication is partially or fully attenuated in the presence of normal levels of functional cellular "pocket protein family" members including Rb/p107/p130/p16/E2F/CDK-cyclin checkpoints. For example, if the infected cell is Rb/p16 pathway impaired or deficient (i.e. the infected cell does not express normal levels of fully functional Rb or other proteins in the Rb/p16 pathway), replication of the Rb/p16/E2F pathway replication impaired adenovirus will proceed normally. Conversely, if a cell expresses normal levels of functional Rb (e.g. Rb with normal activity, also referred to herein as an "Rb expressing cell"), replication of the Rb replication impaired or deficient adenovirus is attenuated or prevented. A cell may be Rb impaired or deficient by failing to express normal levels of Rb (e.g. a mutation to the regulatory (e.g. promoter) region of the Rb gene) or expressing mutated Rb having below normal Rb activity. Normal levels of Rb and normal Rb activity levels are found in healthy, non-diseased cells of the same type. Thus, the Rb impaired cell includes a mutated Rb gene. Optionally, the Rb impaired cell includes a genome wherein the Rb gene is wholly or partially deleted. The Rb impaired cell may be a cancer (e.g. neoplastic) cell. Other genomic lesions that can result in the loss of normal Rb function include, but are not limited to, CDK mutations, cyclin mutations and amplifications, p16 mutations and/or epigenetic silencing, p107 mutations, p130 mutations, and growth factor receptor pathway mutations.

The term "Rb/p16 tumor suppressor pathway" or "Rb/p16 pathway" refers to the entire signaling pathway of molecular signaling that includes retinoblastoma protein (RB), and other protein/protein families in the pathway, including but not limited to Cdk, E2f, atypical protein kinase C, and Skp2. The term "Rb/p16 tumor suppressor pathway impaired or deficient" means that one or more molecules in the signaling pathway are impaired or deficient, e.g., by failing to express normal levels or a protein or expressing mutated proteins having below normal activity, such that the pathway functions abnormally. Such defects result in high expression levels of free E2F and high activity of the E2F promoter. Thus, a cell may be Rb/p16 pathway impaired or deficient by failing to express normal levels of a protein or expressing mutated proteins having below normal activity in the Rb/p16 tumor suppressor pathway.

The terms "E1A impaired," "E1A deficient," "E4orf1 deficient," "E4orf1 impaired," "E4orf6/7 impaired," and "E4orf6/7 deficient" as used herein, means the adenovirus is not capable of producing normal levels and/or fully functional E1A, E4orf1 or E4orf6/7 gene product. For example, a virus may be E1A, E4orf1, or E4 orf6/7 deficient or impaired by failing to express normal levels of E1A, E4orf1 or E4orf6/7 gene product (e.g. a mutation to the regulatory (e.g. promoter) region of the E1A, E4orf1 or E4orf6/7 gene) or expressing a mutated E1A, E4orf1 or E4orf6/7 gene product having below normal E1A, E4orf1 or E4orf6/7 gene product activity. Thus, the E1A, E4orf1 and/or E4orf6/7 deficient adenovirus includes a mutated E1A, E4orf1 and/or E4orf6/7 gene. Optionally, the E1A, E4orf1 and/or E4orf6/7 deficient adenovirus includes a genome wherein the E1A, E4orf1 and/or E4orf6/7 gene is wholly or partially deleted. The E1A and E4 regions of adenoviruses are known and can be modified using the methods described throughout and in the example and others known in the art. See, for example, International Publication No. WO 1998/046779, U.S. Pat. No. 8,465,732, and International Publication No. 2012/024350, which are incorporated by reference herein in their entireties. By way of example, amino acid sequences of the E1A polypeptide can be found at least at GenBank Accession Nos. CAE01147.1, AP_000161.1 (SEQ ID NO: 1), and AP_000197.1 (SEQ ID NO: 2) and amino acid sequences of the E4orf6/7 polypeptide can be found at least at GenBank Accession Nos. AP_000191.1 (SEQ ID NO: 3) and AP_000227.1 (SEQ ID NO: 4). Amino acid sequence of the E4orf1 polypeptide can be found at least at GenBank Accession Nos. AP_000196.1 (SEQ ID NO: 5) and AP_000232.1 (SEQ ID NO: 6). The nucleic acids encoding these polypeptides can be found at least at GenBank Accession Nos. AC_000008.1 (SEQ ID NO: 7) and AC_000007.1 (SEQ ID NO: 8). Also provided are E1A polypeptides comprising 65%, 70%, 75%, 80%, 85%, 90%, 91%, 92%, 93%, 94%, 95%, 96%, 97%, 98%, 99%, or more sequence identity to SEQ ID NO: 1 or SEQ ID NO: 2, E4orf1 polypeptides comprising 65%, 70%, 75%, 80%, 85%, 90%, 91%, 92%, 93%, 94%, 95%, 96%, 97%, 98%, 99%, or more sequence identity to SEQ ID NO: 5 or SEQ ID NO: 6 and E4orf6/7 polypeptide comprising 65%, 70%, 75%, 80%, 85%, 90%, 91%, 92%, 93%, 94%, 95%, 96%, 97%, 98%, 99%, or more sequence identity to SEQ ID NO: 3 or SEQ ID NO: 4.

Various assays for determining levels and activities of protein (such as Rb, E1A gene product, E4orf1 gene product, E4orf6/7 gene product) are available, such as amplification/expression methods, immunohistochemistry methods, FISH and shed antigen assays, southern blotting, or PCR techniques. Moreover, the protein expression or amplification may be evaluated using in vivo diagnostic assays, e.g. by administering a molecule (such as an antibody) which binds the protein to be detected and is tagged with a detectable label (e.g. a radioactive isotope) and externally scanning the patient for localization of the label. Thus, methods of measuring levels of protein levels in cells are generally known in the art and may be used to assess protein levels and/or activities in connection with the methods and compositions provided herein as applicable. These assays can be used to determine the effect of modifications in the E1A, E4orf1, and E4orf6/7 polypeptides and combinations thereof, e.g., to determine if the modifications result in adenoviruses not capable of producing normal levels or fully functional gene products of the polypeptide(s) and to confirm adenoviruses comprising a deletion of all or part of one or more of the E1A, E4orf1 and E4orf6/7 polypeptides or combinations thereof.

Provided are adenoviruses (Ads) that selectively replicate in Rb-deficient cells. Specifically, provided are adenoviruses comprising an E1A polypeptide comprising one or more modifications, comprising an E4orf6/7 polypeptide comprising one or more modifications, comprising an E4orf1 polypeptide comprising one or more modifications and various combinations thereof. Also provided are adenoviruses comprising a genome comprising a deletion of all or part of the E1A gene, the E4orf1 gene, and/or the E4orf6/7 gene. Thus, provided are adenoviruses comprising a genome lacking a nucleic acid sequence encoding the E4orf1 polypeptide and/or lacking a nucleic acid sequence encoding a E4orf6/7 polypeptide and comprising a nucleic acid encoding E1A with one or more modifications. As discussed above, the term "modification" refers to a modification in a nucleic acid sequence of a gene or an amino acid sequence. Modifications include, but are not limited to, insertions, substitutions and deletions. Amino acid sequence modifications typically fall into one or more of three classes: substitutional, insertional, or deletional modifications. Insertions include amino and/or terminal fusions as well as intrasequence insertions of single or multiple amino acid residues. Deletions are characterized by the removal of one or more amino acid residues from the protein sequence. Amino acid substitutions are typically of single residues, but can occur at a number of different locations at once. Substitutional modifications are those in which at least one residue has been removed and a different residue inserted in its place. Substitutions, deletions, insertions or any combination thereof may be combined to arrive at a final construct.

Optionally, the modification of E1A comprises a modification in the Rb binding site of E1A. Optionally, the modification of E1A comprises a modification in one or more of amino acid residues 122-126 of the E1A polypeptide, e.g., amino acid residues 122-126 as compared to SEQ ID NO: 1 or SEQ ID NO: 2. Optionally, the modification is a deletion. Thus, optionally, the modification of E1A and/or E4orf6/7 comprises a deletion. Optionally, the modification of E1A is a deletion of amino acid residues 122-126 of E1A, e.g., as compared to SEQ ID NO: 1 or SEQ ID NO: 2. Optionally, the modification is a deletion in the conserved LXCXE motif of E1A, referred to throughout as ΔLXCXE. By way of example, the conserved motif can be found at amino acid residues 122-126 of SEQ ID NO: 1 or SEQ ID NO: 2. The E4orf6/7 is encoded by two exons, shown in FIGS. 2 and 6. Optionally, the modification of E4orf6/7 comprises a modification in one or both of the E4orf6/7 exons. Optionally, the modification of E4orf6/7 is a deletion of one or both of the E4orf6/7 exons. Optionally, the modification of E4orf6/7 is ΔE4orf6/7. Optionally, the adenovirus comprises E1A ΔLXCXE and ΔE4orf6/7, referred to throughout as Ad E1A ΔLXCXE/ΔE4orf6/7 or AdSyn-CO181.

Thus, provided is an adenovirus comprising an E1A polypeptide comprising one or more modifications and/or comprising an E4orf6/7 polypeptide comprising one or more modifications. The E1A polypeptide can comprise a modification in an Rb binding site of E1A. The E1A polypeptide can comprise two Rb binding sites and wherein the E1A polypeptide comprises a modification in both Rb binding sites. Optionally, the E1A polypeptide comprises a modification in one or more of amino acid residues 120-130 of the E1A polypeptide, a modification in one or more of amino acid residues 122-126 of the E1A polypeptide, a modification in one or more of amino acid residues 35-55 of the E1A polypeptide, a modification in one or more of amino acid residues 37-49 of the E1A polypeptide, or combinations thereof. For example, the modifications can be occur in one or more of amino acid residues 120-130, 122-126, 35-55, 37-49, or combinations thereof as compared to SEQ ID NO: 1 or SEQ ID NO: 2. By way of example, the E1A polypeptide can comprise a modification in one or more of amino acid residues 122-126 and in one or more of amino acid residues 37-49 of the E1A polypeptide, wherein the E1A optionally comprises SEQ ID NO: 1 or SEQ ID NO: 2. Thus, the provided E1A polypeptides can comprise one or more substitutions. Optionally, the E1A polypeptide comprises a substitution at residue Y47, residue C124 or at both residues Y47 and C124, wherein the E1A optionally comprises SEQ ID NO: 1 or SEQ ID NO: 2. Alternatively or additionally, the E1A polypeptide comprises a deletion. Optionally, the deletion is a deletion of amino acid residues 122-126 of the E1A polypeptide and/or a deletion of amino acid residues 2-11 of the E1A polypeptide. Optionally, the E1A polypeptide comprises the deletion ΔLXCXE. As discussed above, the E1A polypeptide to be modified can comprise SEQ ID NO: 1 or SEQ ID NO: 2.

In the provided adenoviruses, the E4orf6/7 polypeptide can comprise a modification in one or both of the E4orf6/7 exons. Thus, the E4orf6/7 polypeptide can comprise one or more modifications including insertions, substitutions and deletions and combinations thereof. Optionally, the E4orf6/7 polypeptide comprises a deletion of one or both of the E4orf6/7 exons. Optionally, the E4orf6/7 comprises an N-terminal deletion selected from the group consisting of 4 to 38, 4 to 58 or 38 to 58 N-terminal amino acids, e.g., as compared to SEQ ID NOs:3 or 4. See, e.g., Schaley et al., *J. Virol.* 79(4):2301-8 (2005), which is incorporated by reference herein in its entirety. Optionally, the E4orf6/7 polypeptide comprises a modification selected from the group consisting of d1355, d1356, and d1366 (Huang and Hearing, *Genes & Development* 3:1699-1710 (1989), which is incorporated by reference herein in its entirety). As discussed above, the E4orf6/7 polypeptide for modification can comprise SEQ ID NO: 3 or SEQ ID NO: 4.

In the provided adenoviruses, the adenoviruses may comprise an E4orf1 polypeptide comprising one or more modifications. Optionally, the E4orf1 polypeptide comprises one or more deletions. Optionally, the E4orf1 polypeptide comprises a deletion in the C-terminal region of E4orf1. Optionally, the E4orf1 polypeptide comprises a deletion of the last four amino acids in the C-terminal region of the E4orf1 polypeptide. Optionally, the E4orf1 polypeptide comprises a deletion of residues 125-128 of the E4orf1 polypeptide, optionally, wherein the E4orf1 polypeptide comprises SEQ ID NO: 5 or SEQ ID NO: 6. Optionally, the E4orf1 polypeptide comprises a modification selected from the group consisting of D68A, P17A, Y26A, L109A, P117A, E3A, L5A, G13T, P31A, G58T, E85A, and L86A (Chung et al., *J. Virol.* 81(9):4787-97 (2007), which is incorporated by reference herein in its entirety). As discussed above, the E4orf1 polypeptide for modification can comprise SEQ ID NO: 5 or SEQ ID NO: 6. Thus, also provided is an adenovirus comprising an E1A polypeptide comprising one or more modifications and comprising an E4orf1 polypeptide comprising one or more modifications. As noted above, the adenovirus can further include an E4orf6/7 polypeptide comprising one or more modifications.

Also provided herein are nucleic acids encoding the modified adenoviruses described above. Optionally, one nucleic acid is provided encoding the modified adenovirus (e.g. a plasmid). Optionally, a plurality of nucleic acids is provided encoding the modified adenovirus (e.g. a plurality of plasmids).

Modifications are generated in the nucleic acid of a virus using any number of methods known in the art. For example, site directed mutagenesis can be used to modify a nucleic acid sequence. One of the most common methods of site-directed mutagenesis is oligonucleotide-directed mutagenesis. In oligonucleotide-directed mutagenesis, an oligonucleotide encoding the desired change(s) in sequence is annealed to one strand of the DNA of interest and serves as a primer for initiation of DNA synthesis. In this manner, the oligonucleotide containing the sequence change is incorporated into the newly synthesized strand. See, for example, Kunkel, 1985, Proc. Natl. Acad. Sci. USA, 82:488; Kunkel et al., 1987, Meth. Enzymol., 154:367; Lewis & Thompson, 1990, Nucl. Acids Res., 18:3439; Bohnsack, 1996, Meth. Mol. Biol., 57:1; Deng & Nickoloff, 1992, Anal. Biochem., 200:81; and Shimada, 1996, Meth. Mol. Biol., 57:157. Other methods are routinely used in the art to introduce a modification into a sequence. For example, modified nucleic acids are generated using PCR or chemical synthesis, or polypeptides having the desired change in amino acid sequence can be chemically synthesized. See, for example, Bang & Kent, 2005, Proc. Natl. Acad. Sci. USA, 102:5014-9 and references therein. Selection on a cell type on which virus is not usually grown (e.g., human cells) and/or chemical mutagenesis (see, for example, Rudd & Lemay, 2005, J. Gen. Virology, 86:1489-97) also can be used to generate modifications in the nucleic acid of a virus.

Also provided is a cell that has been infected with the modified adenovirus described throughout. The cell can be transformed by the modified adenovirus described above. Optionally, the cell has been genetically altered as a result of the uptake, incorporation and expression of the genetic material of the modified adenovirus described above. Optionally, the cell is a mammalian cell, such as a human cell. The adenovirus can be a mammalian adenovirus such as a human adenovirus. Optionally, the cell is an amphibian cell (e.g. a frog cell) or a reptilian cell (e.g. a snake cell).

Compositions

Provided herein are compositions comprising the modified viruses (or one or more nucleic acids encoding the modified adenovirus). The compositions are, optionally, suitable for formulation and administration in vitro or in vivo. Optionally, the compositions comprise one or more of the provided agents and a pharmaceutically acceptable carrier. Suitable carriers and their formulations are described in *Remington: The Science and Practice of Pharmacy*, 22$^{nd}$ *Edition*, Loyd V. Allen et al., editors, Pharmaceutical Press (2012). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

The modified viruses (or one or more nucleic acids encoding the modified adenovirus) are administered in accord with known methods, such as intravenous administration, e.g., as a bolus or by continuous infusion over a period of time, by intramuscular, intraperitoneal, intracerebrospinal, subcutaneous, intra-articular, intrasynovial, intrathecal, oral, topical, intratumoral or inhalation routes. The administration may be local or systemic. The compositions can be administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. Thus, the compositions are administered in a number of ways depending on whether local or systemic treatment is desired, and on the area to be treated.

The compositions for administration will commonly comprise an agent as described herein (e.g. a modified adenovirus or one or more nucleic acids encoding the modified adenovirus) dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Pharmaceutical formulations, particularly, of the modified viruses can be prepared by mixing the modified adenovirus (or one or more nucleic acids encoding the modified adenovirus) having the desired degree of purity with optional pharmaceutically acceptable carriers, excipients or stabilizers. Such formulations can be lyophilized formulations or aqueous solutions.

Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e. g. Zn-protein complexes); and/or non-ionic surfactants. The modified adenovirus (or one or more nucleic acids encoding the modified adenovirus) can be formulated at any appropriate concentration of infectious units.

Formulations suitable for oral administration can consist of (a) liquid solutions, such as an effective amount of the modified adenovirus suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The modified adenovirus (or one or more nucleic acids encoding the modified adenovirus), alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the provided methods, compositions can be administered, for example, by intravenous infusion, orally, topically, intraperitoneally, intravesically intratumorally, or intrathecally. Parenteral administration, intratumoral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced or infected by adenovirus or transfected with nucleic acids for ex vivo therapy can also be administered intravenously or parenterally as described above.

The pharmaceutical preparation is preferably in unit dosage form. In such form the preparation is subdivided into unit doses containing appropriate quantities of the active component.

Thus, the pharmaceutical compositions can be administered in a variety of unit dosage forms depending upon the method of administration. For example, unit dosage forms suitable for oral administration include, but are not limited to, powder, tablets, pills, capsules and lozenges.

Methods of Treatment

The provided modified adenoviruses and/or compositions comprising the modified adenoviruses can be administered for therapeutic or prophylactic treatments.

Thus, provided is a method of treating a proliferative disorder in a subject. The method includes administering the provided adenoviruses or compositions to the subject. As described throughout, the adenovirus or pharmaceutical composition is administered in any number of ways including, but not limited to, intravenously, intravascularly, intrathecally, intramuscularly, subcutaneously, intraperitoneally, or orally. Optionally, the method further comprising administering to the subject one or more additional therapeutic agents. Optionally, the therapeutic agent is a chemotherapeutic agent.

As described throughout, the proliferative disorder can be cancer. Optionally, the proliferative disorder is selected from the group consisting of lung cancer, prostate cancer, colorectal cancer, breast cancer, thyroid cancer, renal cancer, liver cancer and leukemia. Optionally, the proliferative disorder is metastatic. As discussed above, cancers include an abnormal state or condition in a warm-blooded animal characterized by rapidly proliferating cell growth or neoplasm. Neoplastic diseases include malignant or benign neoplasms, including diffuse neoplasms such as leukemia, as well as malignant or benign cancers and tumors (including any carcinoma, sarcoma, or adenoma). A neoplasm is generally recognized as an abnormal tissue that grows by cellular proliferation more rapidly than normal, and can continue to grow after the stimuli that initiated the new growth has ceased. Neoplastic diseases include, for example, tumors such as tumors of the mammary, pituitary, thyroid, or prostate gland; tumors of the brain, liver, meninges, bone, ovary, uterus, cervix, and the like; as well as both monocytic and myelogenous leukemia, adenocarcinoma, adenoma, astrocytoma, bladder tumor, brain tumor, Burkitt lymphoma, breast carcinoma, cervical carcinoma, colon carcinoma, kidney carcinoma, liver carcinoma, lung carcinoma, ovarian carcinoma, pancreatic carcinoma, prostate carcinoma, rectal carcinoma, skin carcinoma, stomach carcinoma, testis carcinoma, thyroid carcinoma, chondrosarcoma, choriocarcinoma, fibroma, fibrosarcoma, glioblastoma, glioma, hepatoma, histiocytoma, leiomyoblastoma, leiomyosarcoma, lymphoma, liposarcoma cell, mammary tumor, medulloblastoma, myeloma, plasmacytoma, neuroblastoma, neuroglioma, osteogenic sarcoma, pancreatic tumor, pituitary tumor, retinoblastoma, rhabdomyosarcoma, sarcoma, testicular tumor, thymoma, Wilms tumor. Tumors include both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). In some aspects, solid tumors may be treated that arise from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, treatments may be useful in the prevention of metastases from the tumors described herein.

In therapeutic applications, compositions are administered to a subject suffering from a proliferative disease or disorder (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" includes both humans and other animals, particularly mammals. Thus the methods are applicable to both human therapy and veterinary applications.

An effective amount of a virus having a modified sequence is determined on an individual basis and is based, at least in part, on the particular virus used; the individual's size, age, gender; and the size and other characteristics of the proliferating cells. For example, for treatment of a human, approximately $10^3$ to $10^{12}$ plaque forming units (PFU) of a virus is used, depending on the type, size and number of proliferating cells or neoplasms present. The effective amount can be from about 1.0 pfu/kg body weight to about $10^{15}$ pfu/kg body weight (e.g., from about $10^2$ pfu/kg body weight to about $10^{13}$ pfu/kg body weight). A virus is administered in a single dose or in multiple doses (e.g., two, three, four, six, or more doses). Multiple doses are administered concurrently or consecutively (e.g., over a period of days or weeks). Treatment with a virus having a modified sequence lasts from several days to several months or until diminution of the disease is achieved.

Optionally, the provided methods include administering to the subject one or more additional therapeutic agents. Thus, the provided methods can be combined with other cancer therapies, radiation therapy, hormone therapy, or chemotherapy. Suitable additional therapeutic agents include, but are not limited to, therapeutic agent is selected from the group consisting of chemotherapeutic agents, CDK inhibitors, anti-inflammatory agents, antibiotics, antiviral agents immunological agents, vitamins, growth factors, and hormones. Thus, the provided methods include, optionally, administering to the subject known anticancer compounds or chemotherapeutic agents. Chemotherapeutic agents, include, but are not limited to 5-fluorouracil; mitomycin C; methotrexate; hydroxyurea; cyclophosphamide; dacarbazine; mitoxantrone; anthracyclins (epirubicin and doxurubicin); antibodies to receptors, such as herceptin; etoposide; pregnasome; hormone therapies such as tamoxifen and anti-estrogens; interferons; aromatase inhibitors; progestational agents; and LHRH analogs. CDK (Cyclin-dependent kinase) inhibitors are agents that inhibit the function of CDKs. Suitable CDK inhibitors for use in the provided methods include, but are not limited to, AG-024322, AT7519, AZD5438, flavopiridol, indisulam, P1446A-05, PD-0332991, and P276-00 (See, e.g., Lapenna et al., *Nature Reviews*, 8:547-566 (2009), which is incorporated by reference herein in its entirety). The choice of agent and dosage can be determined readily by one of skill in the art based on the given disease being treated. The combined administrations contemplates coadministration, using separate formulations or a single pharmaceutical formulation, and consecutive administration in either order, wherein preferably there is a time period while both (or all) active agents simultaneously exert their biological activities. Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions. According to the methods taught herein, the subject is administered an effective amount of one or more of the agents provided herein. The terms effective amount and effective dosage are used interchangeably. The term effective amount is defined as any amount necessary to produce a desired physiologic response (e.g., killing of a cancer cell). Therapeutic agents are typically administered at the initial dosage of about 0.001 mg/kg to about 1000 mg/kg daily. A dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the subject, the severity of the condition being treated, and the compound being employed. For example, dosages can be empirically determined considering the type and stage of cancer diagnosed in a particular subject. The dose administered to a subject, in the context of the provided methods should be sufficient to affect a beneficial therapeutic response in the patient over time. Determination of the proper dosage for a particular situation is within the skill of the practitioner. Thus, effective amounts and schedules for administering the agent may be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products.

As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

Kits

Provided herein are kits comprising one or more of the provided modified adenoviruses and/or compositions comprising the modified adenoviruses. Thus, provided are kits comprising adenoviruses (Ads) comprising an E1A polypeptide comprising one or more modifications and/or comprising an E4orf6/7 polypeptide comprising one or more modifications and/or compositions comprising the adenoviruses. Optionally, the adenoviruses further include an E4orf1 polypeptide comprising one or more modifications. Provided are also kits comprising adenoviruses (Ads) comprising an E1A polypeptide comprising one or more modifications and comprising an E4orf1 polypeptide comprising one or more modifications and/or compositions comprising the adenoviruses. Optionally, the composition is a pharmaceutical composition. Optionally, the kit further includes one or more additional therapeutic agents. Optionally, the therapeutic agent is a chemotherapeutic agent. Provided herein are kits comprising one or more of the provided pharmaceutical compositions and instructions for use. Optionally, the kit comprises one or more doses of an effective amount of a composition comprising an adenovirus that selectively replicates in Rb/p16 tumor suppressor pathway deficient cells. Optionally, the adenovirus selectively replicates in cells with upregulated E2F activity. Optionally, the composition is present in a container (e.g., vial or packet). Optionally, the kit comprises a means of administering the composition, such as, for example, a syringe, needle, tubing, catheter, patch, and the like. The kit may also comprise formulations and/or materials requiring sterilization and/or dilution prior to use.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the claims.

EXAMPLES

Example 1. Oncolytic Adenoviruses that Selectively Replicate in Tumor Cells that have Deregulated E2F Activity Modified adenoviruses were made with the below referenced components. Gateway DONR vectors were employed. From human Ad5 DNA, the E1 module was obtained by PCR and inserted into the vector pDONR P1P4 using SLIC. The pDONR P1P4 vector backbone including attL1 and attL4 recombination sites was amplified using PCR and combined with the Ad5 E1 module by SLIC. The E3 module was obtained by PCR to generate a product flanked by attB5 and attB3r recombination sites. The product was inserted into the pDONR P5P3r vector by gateway BP reaction. The E4 module was obtained by PCR to generate a product flanked by attB3 and attB2 recombination sites. The product was inserted into the pDONR P3P2 vector by gateway BP reaction. The attR5-ccdB-Cm(r)-attR2 fragment from the pDONR P5P2 vector was amplified by PCR and inserted into the Adsembly DEST vector. See "MultiSite Gateway® Pro Plus", Cat #12537-100; and Sone, T. et al. J Biotechnol. 2008 Sep. 10; 136(3-4):113-21. The Adsembly method is described in International Publication No. WO 2012/024351, which is incorporated by reference herein in its entirety.

The vector backbone for the Adsembly DEST vector is composed of parts from three different sources. The Amp(r) cassette and lacZ gene was amplified from plasmid pUC19. This was combined with the p15A origin of replication, obtained from plasmid pSB3K5-I52002, part of the BioBricksiGEM 2007 parts distribution. The p15A ori, which maintains plasmids at a lower (10-12) copy number is necessary to reduce E1 toxicity. Lastly, in order to create a self-excising virus, the mammalian expression cassette for the enzyme ISceI was PCR amplified from plasmid pAdZ5-CV5-E3+. This cassette was cloned into the vector backbone to create the vector called p15A-SceI. This is the vector used to start genome assembly. The gene modules were all obtained from either DNA purified from wild type Ad5 virus or the plasmid pAd/CMV/V5/DEST (Invitrogen).

Regarding the DEST vector for human Ad5, the E2 and L3 modules were inserted into plasmid p15A-SceI by 3-fragment SLIC. The counterselection marker expressing ccdB and Chlor(r) flanked by attR5 and attR2 sites was obtained by PCR from plasmid pDONR P5P2. The second counterselection marker was obtained by PCR from the vector pDONR P1P4. The two counterselection markers were inserted on the right and left sides of p15A-SceI E2-L4 by SLIC after cutting with unique restriction enzymes engineered to the ends of the E2 and L4 modules to create the DEST vector.

Regarding Amp(r) cassette: plasmid pUC19, the p15A ori: plasmid pSB3K5-I52002 was part of the BioBricksiGEM 2007 parts distribution. Regarding the adenoviral gene modules, either the DNA purified from Ad5 particles, or plasmid pAd/CMV/V5/DEST (Invitrogen). The DONR vectors pDONR P1P4, P5P2, P5P3R, P3P2 were received from Jon Chesnut (Invitrogen).

Regarding PCRs, all PCRs were performed using the Phusion enzyme (NEB). PCRs to obtain the ADENOVIRAL GENE modules from Ad5 were performed with 1×HF buffer, 200 M each dNTP, 0.5 µM each primer, and 10 ng of template. For the E2-L2 module, 3% DMSO was also added. Template was either plasmid pAd/PL-DEST (Invitrogen; for E2-L2, L3-L4, and E4 modules) or Ad5 genomic DNA (for E1 and E3 modules). PCR conditions were as follows. E2-L2 and L3-L4: 98° C. 30 sec-10 cycles of 98° C. 10 sec, 65° C. 30 sec (decrease temp 1° C. every 2 cycles), 72° C. 7 min-29 cycles of 98° C. 10 sec, 60° C. 30 sec, 72° C. 8 min-72° C. 10 min-4° C. hold. E3: 98° C. 30 sec-10 cycles of 98° C. 10 sec, 70° C. 30 sec (decrease temp 0.5° C. every cycle), 72° C. 2 min 30 sec-25 cycles of 98° C. 10 sec, 68° C. 30 sec, 72° C. 2 min 30 sec-72° C. 10 min-4° C. hold. E4: 98° C. 30 sec-6 cycles of 98° C. 10 sec, 63° C. 30 sec (decrease temp 0.5° C. every cycle), 72° C. 2 min-29 cycles of 98° C. 10 sec, 60° C. 30 sec, 72° C. 2 min-72° C. 5 min-4° C. hold.

Regarding obtaining viral genomic DNA from purified virus, up to 100 µl of purified virus is added to 300 µl of lysis buffer containing 10 mM Tris pH8, 5 mM EDTA, 200 mM NaCl, and 0.2% SDS. Mix is incubated at 60° C. for 5 min, followed by addition of 5 µl of proteinase K stock (~20 mg/mL) and further incubated at 60° C. for 1 hour. Samples are then placed on ice for 5 min, followed by spinning at 15K×g for 15 min. Supernatant is removed and added to an equal volume of isopropanol, mixed well, and spun at 15K×g for 15 min at 4° C. Pellet is washed with 70% ethanol and respun for 15 min at 4° C. The pellet is dried and resuspended for use.

Regarding SLIC, linear fragments are exonuclease treated for 20 min at room temp in the following 201 reaction: 50 mM Tris pH8, 10 mM MgCl2, 50 µg/mL BSA, 200 mM Urea, 5 mM DTT, and 0.5 µl T4 DNA polymerase. The reaction is stopped by addition of 1 µl 0.5 M EDTA, followed by incubation at 75° C. for 20 min. An equal amount of T4-treated DNAs are then mixed to around 20 µl in volume in a new tube. For SLIC combining 2 fragments, 10 µl of each reaction is used. For SLIC combining 3 fragments, 7 µl of each reaction is used. Fragments are annealed by heating to 65° C. for 10 min, followed by a slow cool down decreasing the temperature 0.5° C. every 5 seconds down to 25° C. After annealing, 5 µl of the reaction is transformed and clones are screened.

Regarding AdSlicR, a 3-fragment SLIC reaction is performed using 100 ng of T4-treated p15A-SceI (linearized by PCR), and 300 ng of each of the E2 and L3 modules (obtained by PCR from their respective entry vectors). This creates vector p15A-SceI E2-L4. Five g of p15A-SceI E2-L4 is cut with SwaI and gel purified using Qiagen QiaexII. The E3 and E4 modules are obtained by PCR from their respective entry vectors. Each of the linearized vector (450 ng) and PCR products (200 ng) are treated with T4 DNA polymerase and SLIC performed as normal, using 150-200 ng of vector and ~100 ng of each module PCR. After isolation of positive clones, 5 µg of the new vector is cut with PacI and gel purified, then combined with an E1 PCR product (100 ng of T4-treated) in a new SLIC reaction. This completes the genome assembly, and the plasmid is ready for transfection to reconstitute virus.

Regarding the construction of E1 and E4 mutant regions, manipulation was carried out on the individual module entry vectors. The E1 module with vector backbone was PCR amplified with primers to generate a product lacking the LTCHE sequence (residues 122-126), then circularized using SLIC to generate pENTR-E1-E1A-ΔLXCXE. Alternatively, the E1 module with vector backbone was PCR amplified with primers to generate products with E1A codon changes to mutate Y47 to H, residue C124 to G, or to delete residues 2-11 to generate pENTR-E1-E1A-Y47H, pENTR-E1-E1A-C124G, or pENTR-E1-E1A-A2-11 respectively. These products were used as the template for further PCR mutation to generate combinations of these mutations: pENTR-E1-E1A-Y47H-C124G and pENTR-E1-E1A-Y47H-C124G-A2-11. The E4 module with vector backbone was PCR amplified with primers to generate a product lacking the E4orf6/7-specific exon sequence (297 bp) downstream of the E4orf6 stop codon to generate pENTR-E4-ΔE4orf6/7. This product was also used as the template for PCR with primers to generate products either lacking the PDZ-binding motif of E4orf1, or the entire E4orf1 sequence (pENTR-E4-ΔE4orf6/7-E4orf1ΔPDZb and pENTR-E4-ΔE4orf6/7-ΔE4orf1 respectively).

To generate complete virus genomes bearing the mutations, AdSlicR was performed using p15A-SceI E2-L4 in combination with the wt E3 module and the wt E4 or a mutant E4 module, then with either the wt E1 or mutant E1. The wild type AdSlicR adenoviruses are designated in Table 1 shown below.

TABLE 1

| Adenovirus Modifications in E1 and E4 | | |
|---|---|---|
| Ad | E1 | E4 |
| Ad-102 [AdSyn-CO102] | wt | wt |
| Ad-210 [AdSyn-CO210] | wt | ΔE4orf6/7 |
| AdSyn-CO283 | wt | E4orfl ΔPDZb, ΔE4orf6/7 |
| AdSyn-CO284 | wt | ΔE4orf1, ΔE4orf6/7 |
| Ad-189 [AdSyn-CO189] | E1A ΔLXCXE | wt |
| Ad-181 [AdSyn-CO181] | E1A ΔLXCXE | ΔE4orf6/7 |
| AdSyn-CO285 | E1A ΔLXCXE | E4orf1 ΔPDZb, ΔE4orf6/7 |
| AdSyn-CO286 | E1A ΔLXCXE | ΔE4orf1, ΔE4orf6/7 |
| AdSyn-CO235 | E1A C124G | wt |
| AdSyn-CO287 | E1A C124G | ΔE4orf6/7 |
| AdSyn-CO288 | E1A C124G | E4orf1 ΔPDZb, ΔE4orf6/7 |
| AdSyn-CO289 | E1A C124G | ΔE4orf1, ΔE4orf6/7 |
| AdSyn-CO236 | E1A Δ2-11 | wt |
| AdSyn-CO290 | E1A Δ2-11 | ΔE4orf6/7 |
| AdSyn-CO291 | E1A Δ2-11 | E4orf1 ΔPDZb, ΔE4orf6/7 |
| AdSyn-CO292 | E1A Δ2-11 | ΔE4orf1, ΔE4orf6/7 |
| AdSyn-CO238 | E1A Y47H, C124G | wt |
| AdSyn-CO293 | E1A Y47H, C124G | ΔE4orf6/7 |
| AdSyn-CO294 | E1A Y47H, C124G | E4orf1 ΔPDZb, ΔE4orf6/7 |
| AdSyn-CO295 | E1A Y47H, C124G | ΔE4orf1, ΔE4orf6/7 |
| AdSyn-CO244 | E1A Y47H, C124G, Δ2-11 | wt |
| AdSyn-CO296 | E1A Y47H, C124G, Δ2-11 | ΔE4orf6/7 |
| AdSyn-CO297 | E1A Y47H, C124G, Δ2-11 | E4orf1 ΔPDZb, ΔE4orf6/7 |
| AdSyn-CO298 | E1A Y47H, C124G, Δ2-11 | ΔE4orf1, ΔE4orf6/7 |

Regarding virus production, concentration and purification, 293 E4 cells are infected with infectious particles, and approximately 48 hours post-infection when CPE is apparent, the cells are collected and isolated by centrifugation at 500×g for 5 minutes. The cells are lysed in TMN buffer (10 mM TrisCl pH 7.5, 1 mM MgCl2, 150 mM NaCl) via 3× freeze/thaws, and the cell debris is removed by two rounds of centrifugation at 3K×g and 3.5K×g for 15 minutes. A cesium chloride gradient (0.5 g/mL) is used to band virus particles via ultracentrifugation at 37K×g for 18-24 hours. The band is collected and dialyzed in a 10 k MWCO Slide-A-Lyzer® dialysis cassette (Thermo Scientific) in TMN with 10% glycerol overnight (12-18 h) at 4° C., then stored at −80° C. The titer of the purified virus is determined versus a titered wild type standard by a cell-based serial dilution infection ELISA with anti-adenovirus type 5 primary antibody (ab6982, Abcam), and ImmunoPure anti-rabbit alkaline phosphatase secondary antibody (Thermo Scientific).

Regarding evaluation of adenovirus protein expression during infection of primary human small airway epithelial cells (SAEC), quiescent SAEC in 12-well plates were infected with MOI 30 adenovirus, and the media is replaced on the cells 4 hours after infection. At 24, 36, and 48 hours after infection, cells were washed with cold PBS, harvested in 500 uL cold PBS, pelleted at 5K rpm for 5 min at 4° C., snap frozen and stored at −80° C. Cell pellets were lysed in RIPA buffer (100 mM Tris pH7.4, 300 mM NaCl, 2 mM EDTA, 2% Triton X, 2% deoxycholate, 2 mM NaF, 0.2 mM NaVO$_4$, 2 mM DTT) for 1 hour at 4° C., including sonication in a cup sonicator (2×60 s pulses at 60 amplitude at 4° C.). Cell debris was pelleted by centrifuging at 13K rpm for 20 min at 4° C. Protein concentration was determined using Bio-rad's DC™ Protein Assay, and the protein concentration of the samples were normalized. Gel electrophoresis was performed using Life Technologies' Novex® NuPAGE® SDS-PAGE gels, as per the manufacturer's protocol. Proteins were detected by Western blot. The primary antibodies used to detect proteins follows: E1A (ab28305, Abcam), β-actin (A5441, Sigma), Ad5 late proteins (ab6982, Abcam), cyclin A (Ab-6 6E6, NeoMarkers), cyclin B (Ab-3 GNS1, NeoMarkers). Life Technologies' Alexa Fluor® antibodies were used as secondary antibodies, and the signal was detected using a LI-COR ODYSSEY® instrument. Regarding evaluation of adenovirus protein expression during infection of lung adenocarcinoma A549 cells and normal human astrocyte cells (NHA), confluent cells in 12-well plates were infected with MOI 10 adenovirus, and similarly processed as described for SAEC. Regarding evaluation of adenovirus protein expression during infection of glioblastoma U87 cells, glioblastoma U118 cells, human vascular endothelial cells (HuVEC), and human fibroblasts, confluent cells in 12-well plates were infected with MOI 20 adenovirus, and similarly processed as described for SAEC.

Regarding cell cycle analysis, cells were infected with the same MOI as for protein expression. Forty-eight hours post-infection, cells were trypsinized off the plate and washed with cold PBS. Cells were resuspended in 500 uL cold PBS, and fixed with 3 mL cold 70% EtOH/15 mM glycine, pH 2.8. Samples were kept at 4° C., and prior to FACS, the cells were pelleted, washed in cold PBS, and resuspended in propidium iodide (PI)/RNase A solution, then incubated at 37° C. for 1 h. At least 10K events were collected by FACS for each sample.

Regarding adenovirus bursts from infection, quiescent cells in 12-well plates were infected with MOI 1 or 10 adenovirus, and the media is replaced on the cells 4 hours after infection. Media from the wells is collected 48 and 72 hours post-infection, flash frozen and thawed once, and centrifuged at 7K rpm at 4° C. for 5 min to pellet cellular debris. The volume of the media is measured, and is flash frozen and stored at −80° C. The titer of the virus in the media is determined versus a titered wild type standard by a cell-based serial dilution infection ELISA with anti-adenovirus type 5 primary antibody (ab6982, Abcam), and ImmunoPure anti-rabbit alkaline phosphatase secondary antibody (Thermo Scientific).

Regarding cell viability assays, cells were seeded in 96-well plates, and in infected in triplicate at serial dilutions at MOI 30. Following infection at 7-10 days when there is complete CPE in the MOI 10 infected wells, metabolic activity is measured using cell proliferation reagent WST-1 (Roche) as per manufacturer's specifications.

Figure 2:
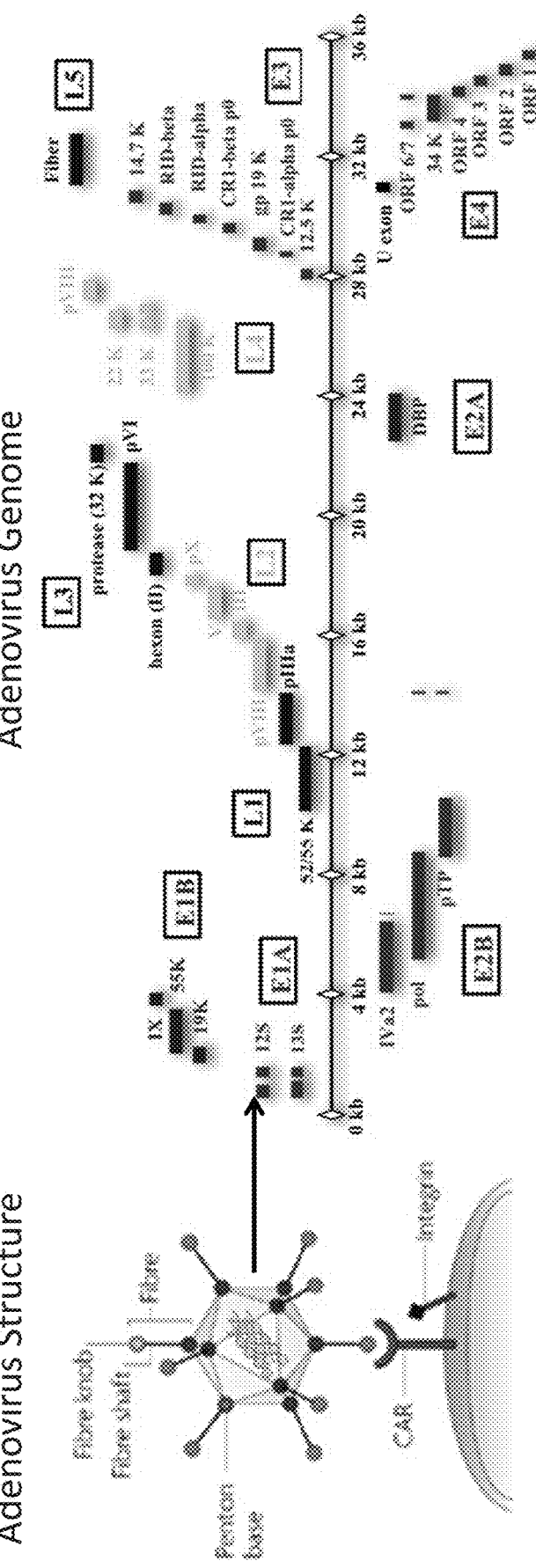
FIG. 2 is a schematic showing the structural features of adenovirus (Ad) and a map of the adenovirus genome with transcriptional units in boxes and labeled genes.
Figure 4B:
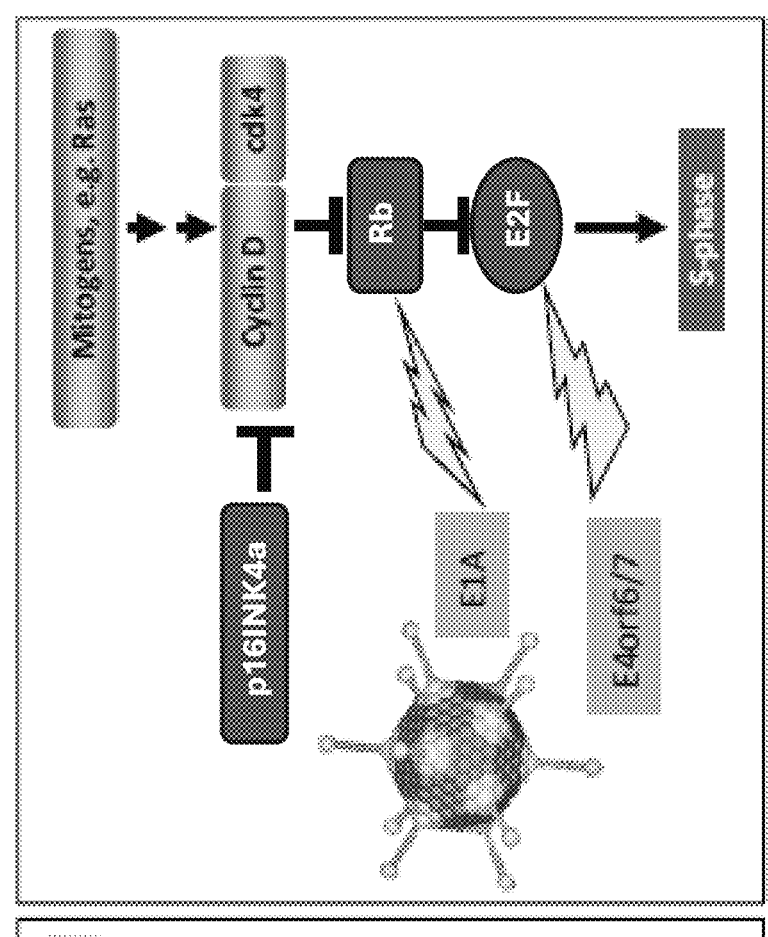
FIGS. 4A and 4B are schematics showing tumor mutations and Adenovirus early proteins that converge in activating the Rb/p16 tumor suppressor pathway to activate E2F and elicit uncontrolled replication.
Figure 4A:
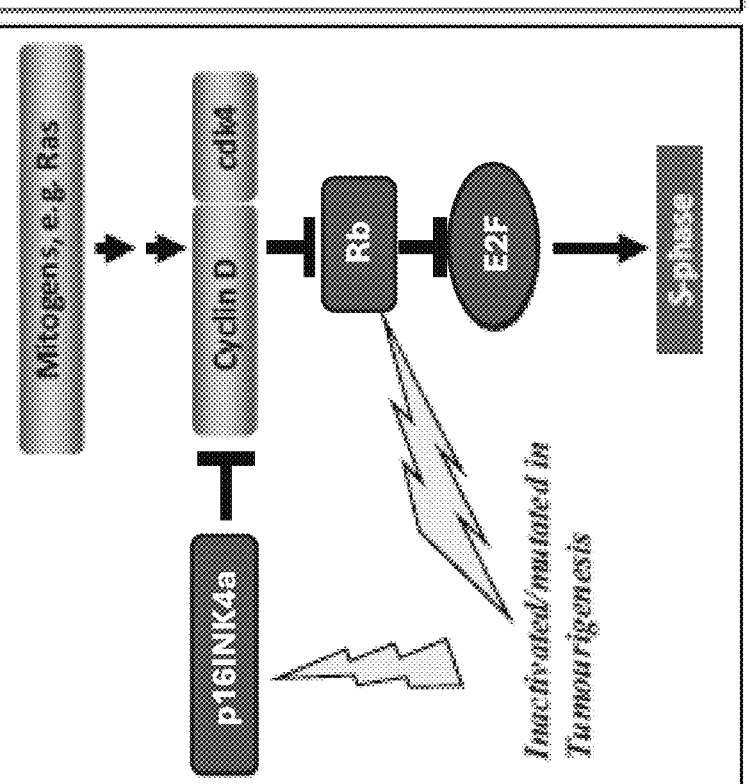
Figure 5:
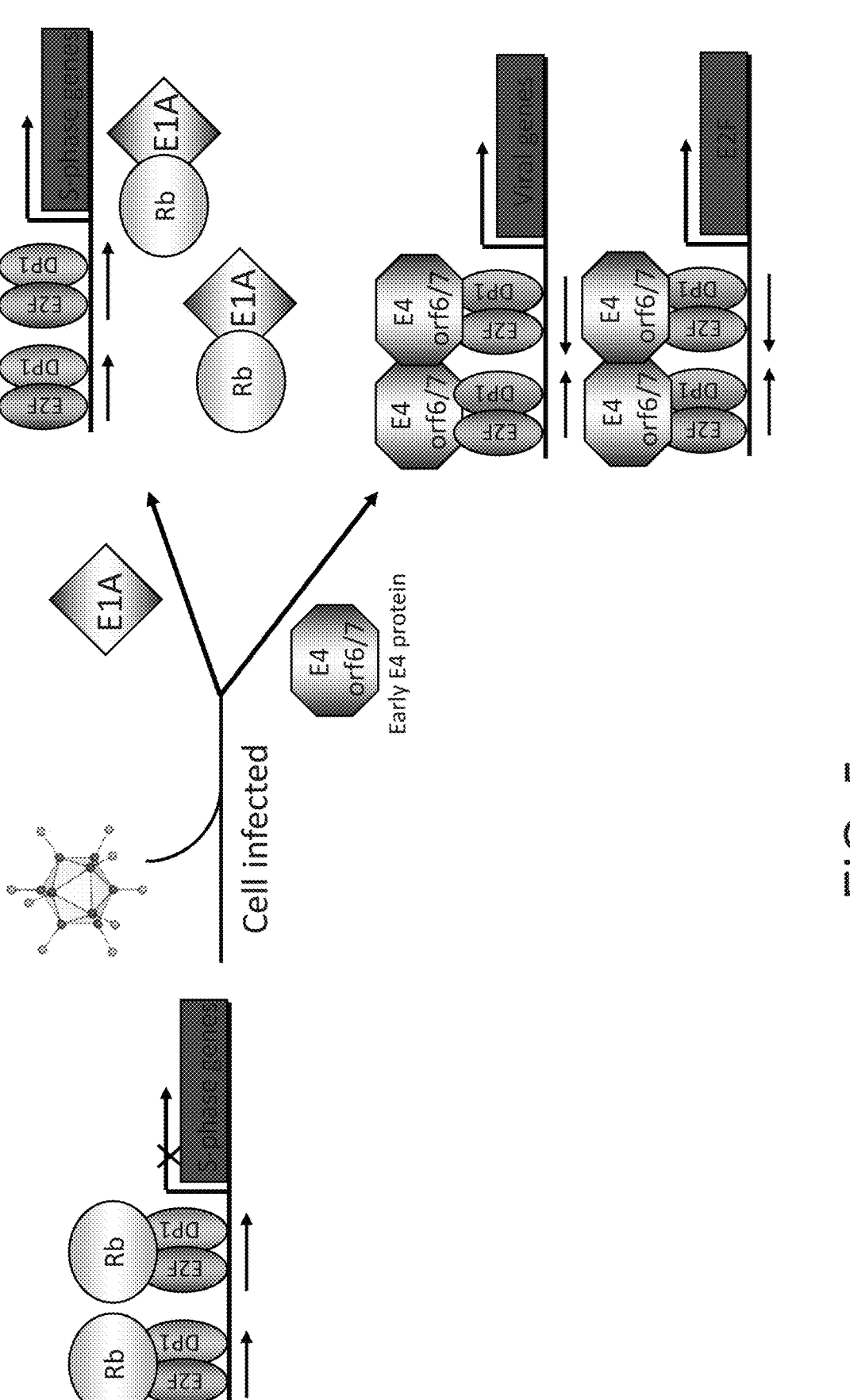
FIG. 5 is a schematic showing multiple adenovirus encodes proteins that deregulate the Rb-E2F cell cycle checkpoint. Adenovirus E1A binds to cellular Rb through a conserved LXCXE motif, releasing E2F to activate transcription of cellular genes required for viral and cellular DNA replication. E1A is thought to be the critical mechanism through which adenovirus inactivates the Rb checkpoint and activates E2F target genes. In addition, another adenovirus protein, E4orf6/7, stabilizes E2F-DP1 and dimerizes at cellular and viral E2 promoters to enhance transcriptional activation (Schaley, J., et al., Protein J. Virol., 74(5):2084-2093 (2000); Cress, et al., Genes & Development, 7(10):1850-61 (1993)).
Figure 6:
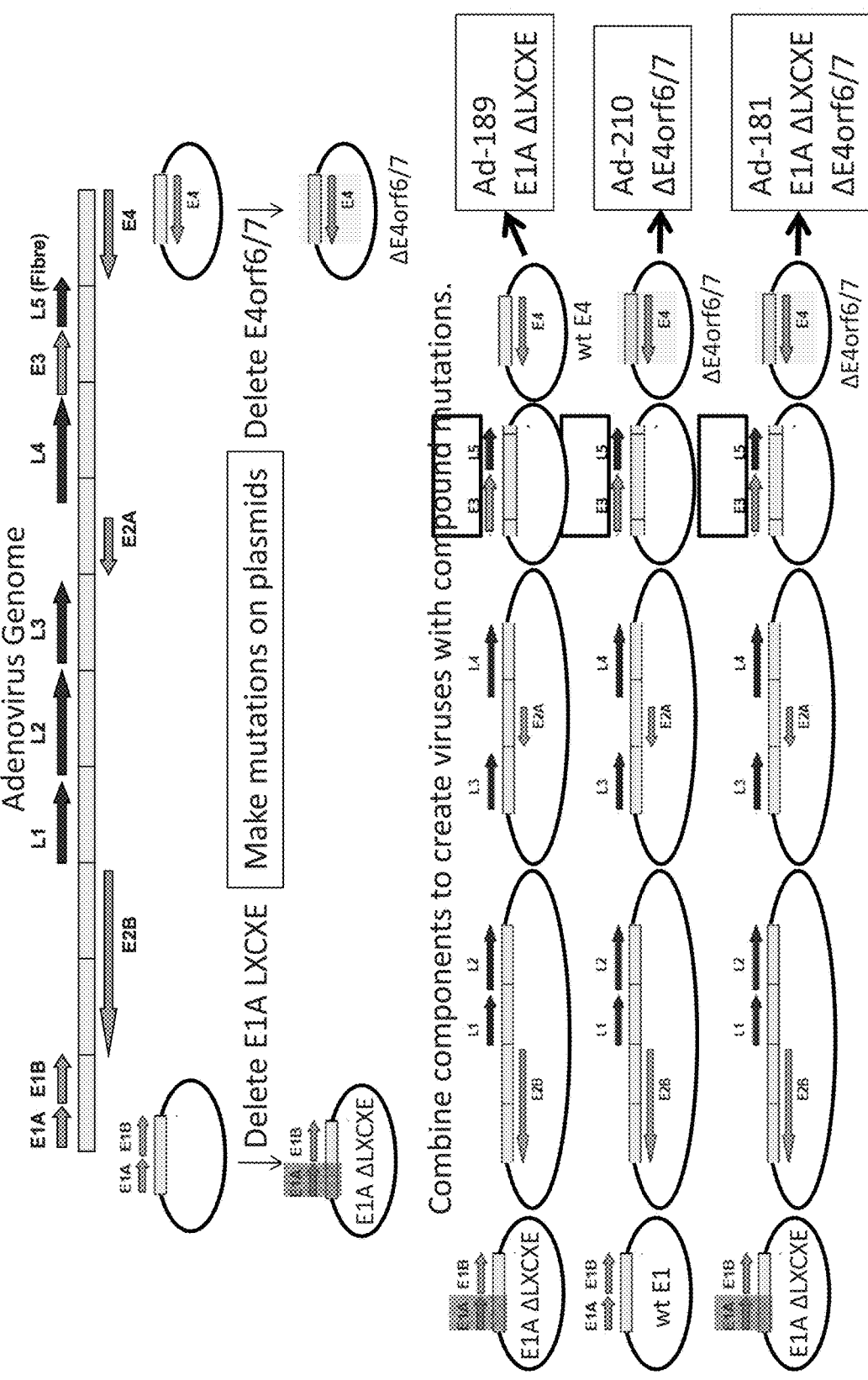
FIG. 6 is a schematic showing construction of initial series of mutant adenoviruses in this work. The wild-type Ad5 genome was split into modules according to transcriptional units, and each of the modules was placed in different plasmids. Mutations were made on the module plasmids, and using a PCR-based approach (AdSlicR), the modules were reassembled into complete genomes enabling generation of recombinant adenoviruses.
Figures 7A, 7B:
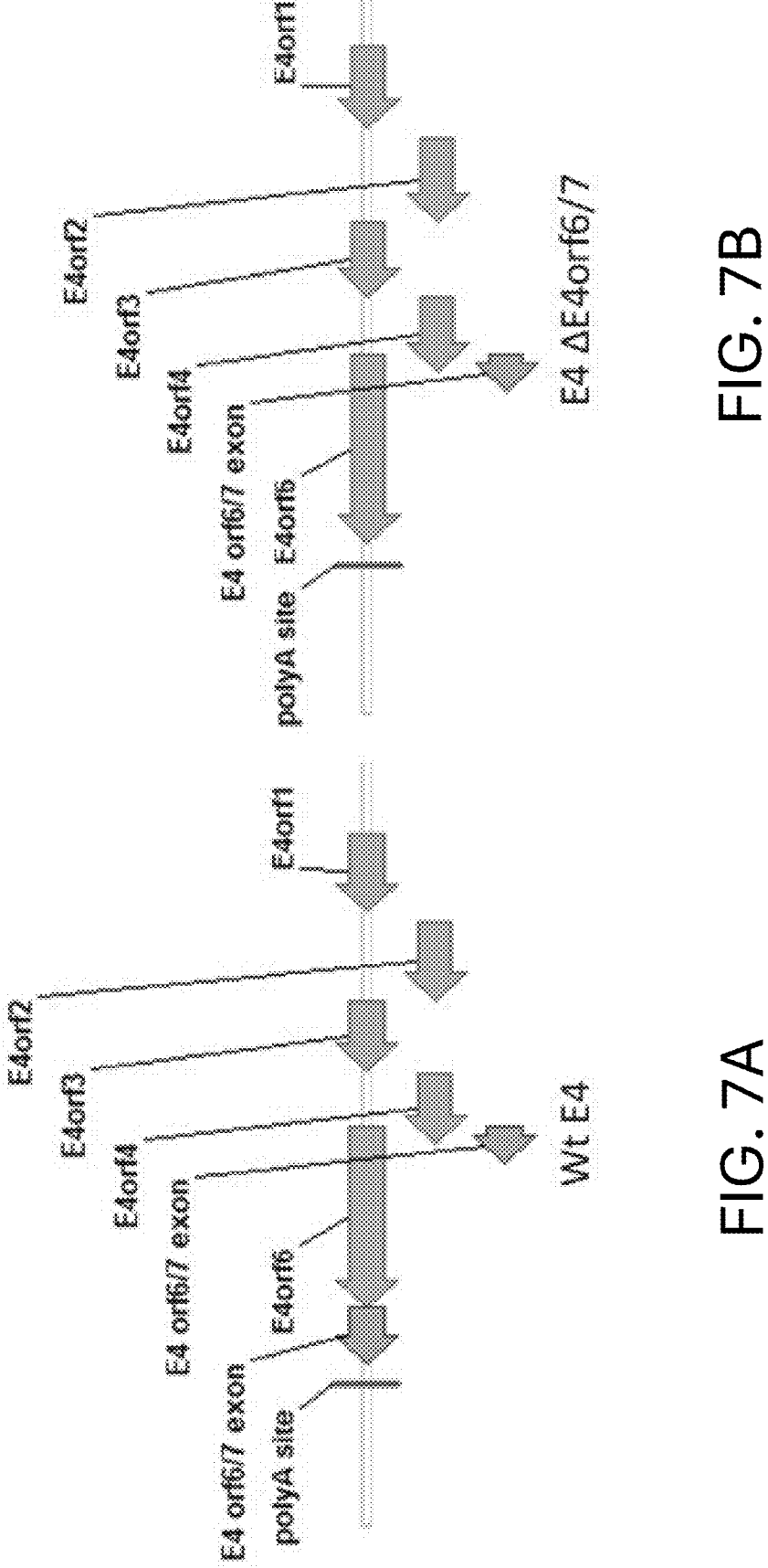
FIGS. 7A and 7B are schematics showing the E4orf6/7 deletion. Two exons encode E4orf6/7. E4orf6 and E4orf6/7 utilize same start codon and share 58 amino acid N-terminal residues. The E4orf6/7 transcript splices immediately following E4orf6 stop codon. The entire second exon of E4orf6/7, including the stop codon was deleted.

The data are shown in FIGS. 1-16. As discussed above, cancer continues to be a problematic disease in need of additional therapeutic treatments. One such treatment includes oncolytic viruses. See FIG. 1 for a schematic showing the general rationale of oncolytic viral cancer therapy. Adenoviruses are one of the viruses being explored for use as an oncolytic virus. FIG. 2 is a schematic showing the structural features of adenovirus (Ad) and a map of the adenovirus genome with transcriptional units in boxes and labeled genes. The retinoblastoma (Rb) tumor suppressor pathway function is lost in almost every human cancer either by direct mutation of Rb, by loss of CDK-inhibitor p16 function due to mutation/methylation, or by amplification of CDK/cyclins. In normal, non-dividing cells, Rb remains hypophosphorylated and binds to transcription factor E2F at its target promoters, suppressing transcription by masking the E2F transactivation domain as well as recruiting chromatin-remodeling complexes and histone-modifying activities. During the G1-S transition of the cell cycle, CDKs phosphorylate Rb which relieves E2F suppression. Adenoviruses express early viral oncoproteins that inactivate the Rb tumor suppressor pathway to force cells to replicate and concomitantly reproduce the viral genome. Adenovirus E1A binds Rb, in part, via an LXCXE motif, deregulating its tumor suppressor activities. It was thus proposed that deleting the LXCXE motif in E1A would eliminate Rb inactivation, and make a selectively replicating virus (ONYX-838). However, Johnson et al., *Cancer Cell*, 1(4):325-337 (2002) provided evidence that Ad E1A LXCXE mutation is not sufficient to prevent S-phase entry, viral DNA replication, and late protein expression, consistent with results from experiments described herein. Even though the Rb-selectivity of the E1A mutant is controversial, this mutation has been carried forward as the basis for an oncolytic virus (DNX-2401) that is moving into phase II clinical trials for malignant brain tumors. In an attempt to achieve higher Rb-selectivity, an adenovirus was generated that replaced the promoters for the Adenovirus E1 and E4 regions with E2F promoters and combined it with the E1A ΔLXCXE motif to generate ONYX-411 (Johnson et al., *Cancer Cell*, 1(4):325-337 (2002); and Dubensky et al., *Cancer Cell*, 1(4):307-309 (2002)). To test these viruses, tumor and primary human cells were infected with either wild type virus, ONYX-838 (E1A ΔLXCXE) or ONYX-411 and harvested at various time points post infection (FIG. 3). As shown in FIG. 3, ONYX-838 indiscriminately replicates in tumor and primary lung epithelial cells. ONYX-411, which combines the E1A ΔLXCXE with cellular E2F control of adenovirus E1A, E1B and E4 regions (shown in FIG. 2) demonstrates selective-replication in tumor cells vs. normal cells (Johnson et al., *Cancer Cell* 1(4):325-337 (2002)). However, the E2F promoters result in recombination and also limit replication to wild type virus levels in tumor cells. Thus, these viruses remain problematic As described herein, independently of E2F release from Rb suppression by E1A, there is another Ad protein, E4orf6/7, that further stabilizes E2F proteins at cellular and Ad promoters. Together, E1A and E4orf6/7 drive E2F-mediated transcription, causing S-phase initiation, concomitantly propagating the viral DNA genome. Therefore, provided herein is an Adenovirus bearing both E1A modifications and E4orf6/7 modifications that is a selective oncolytic viral therapy for tumor cells lacking functional Rb. Specifically, compound mutations in E1A/E4orf6/7 were engineered to determine if they selectively replicate in tumor cells, but not primary cells. It is proposed that the combination of these mutations result in an effective, self-amplifying therapy for cancer. FIGS. 4A and 4B are schematics showing tumor mutations and Adenovirus early proteins converge in activating the Rb pathway to elicit uncontrolled replication. A) Common mutations that cause loss of Rb-tumor suppressor functions. B) Adenovirus proteins directly deregulate Rb and E2F to drive the cell into S-phase. FIG. 5 is a schematic showing Adenovirus encodes multiple proteins to deregulate the Rb-E2F cell cycle checkpoint. Adenovirus E1A binds to cellular Rb, releasing E2F to activate transcription. Adenovirus E4orf6/7 stabilizes E2F at promoters to enhance expression of downstream genes. FIG. 6 is a schematic showing construction of mutant adenoviruses in this work. The wild type Ad5 genome was split into modules according to transcriptional units, and each of the modules was placed in different plasmids. Mutations were made on the module plasmids, and using AdSlicR, the modules were reassembled into complete genomes enabling generation of recombinant adenoviruses. FIG. 7 is a schematic showing the E4orf6/7 deletion. Two exons encode E4orf6/7. E4orf6 and E4orf6/7 utilize same start codon and share 58 amino acid N-terminal residues. The E4orf6/7 transcript splices immediately following E4orf6 stop codon. The entire second exon of E4orf6/7, including the stop codon was deleted. FIG. 7A shows the wild type E4 region. FIG. 7B shows the resulting E4 ΔE4orf6/7 region.

Figures 8A, 8B:
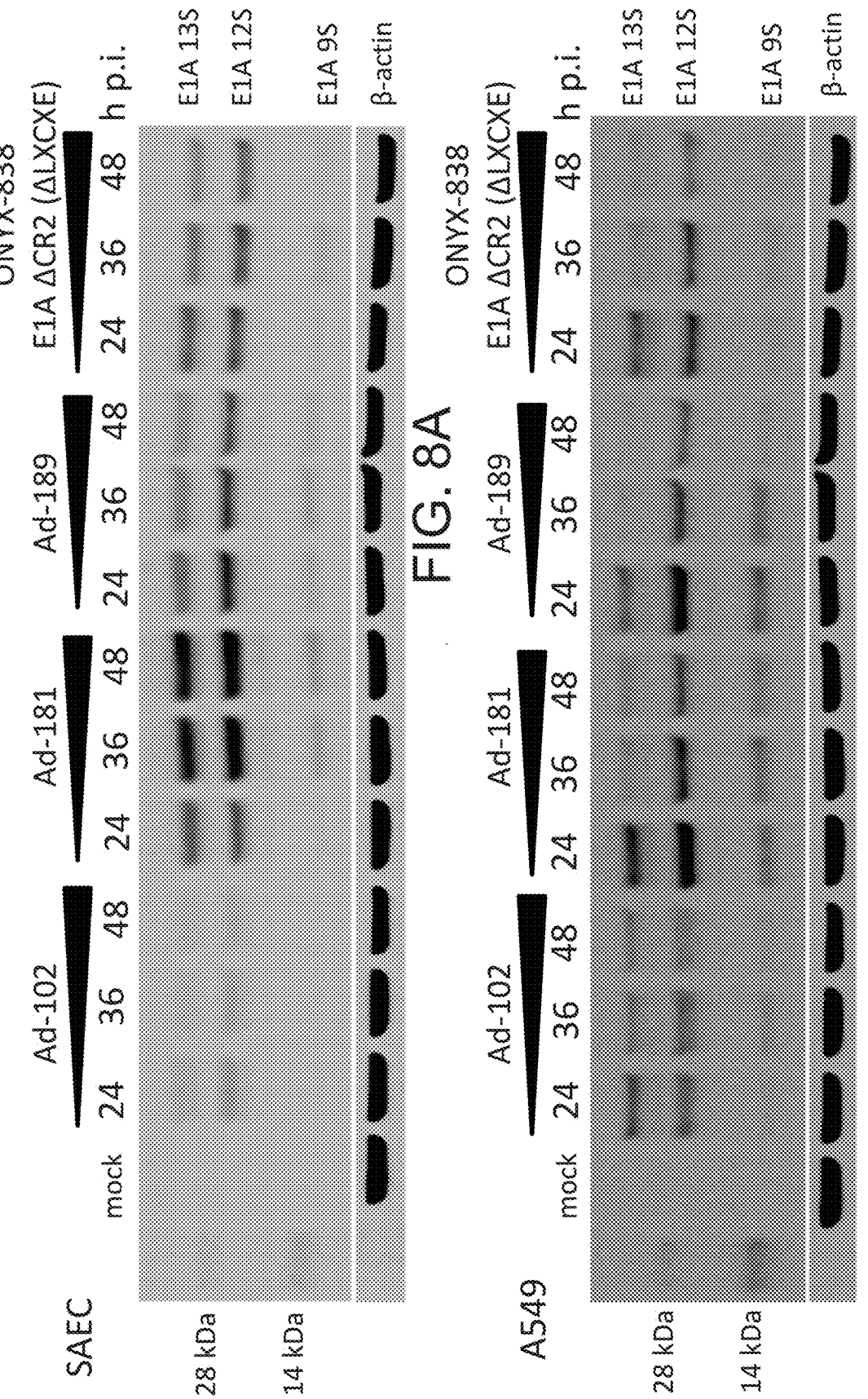
FIGS. 8A and 8B are pictures of immunoblots of cell lysates showing expression of adenovirus early E1A from mutant Ad infected cells. Cells infected with mock (ΔE1), Ad-102 (also referred to herein as AdSyn-CO102) (wild type), Ad-181 (also referred to herein as AdSyn-CO181) (E1A ΔLXCXE/ΔE4orf6/7), Ad-189 (also referred to herein as AdSyn-CO-189) (E1A ΔLXCXE), or ONYX-838 (E1A ΔCR2). ONYX-838 also lacks ΔLXCXE which is in the CR2 domain of E1A. For FIG. 8A, quiescent human primary small airway epithelial cells (SAEC) were infected at MOI 10. Lysates were analyzed for E1A expression. Ad-102 (AdSyn-CO102) shows expected decrease of E1A levels at later times during infection. Similarly Ad-189 (AdSyn-CO189) and ONYX-838 show a decrease of E1A levels at later times during infection, but have stronger expression at the earlier time point. Ad-181 (AdSyn-CO181) shows stronger and continued expression of E1A throughout the infection, which is indicative of failure to progress through the adenovirus lifecycle. For FIG. 8B, confluent lung adenocarcinoma cells (A549) were infected at MOI 30. Lysates were analyzed for E1A expression. All infections show expected decrease of E1A levels at later times during infection, indicative of typical adenovirus lifecycle progression.
Figures 9A, 9B:
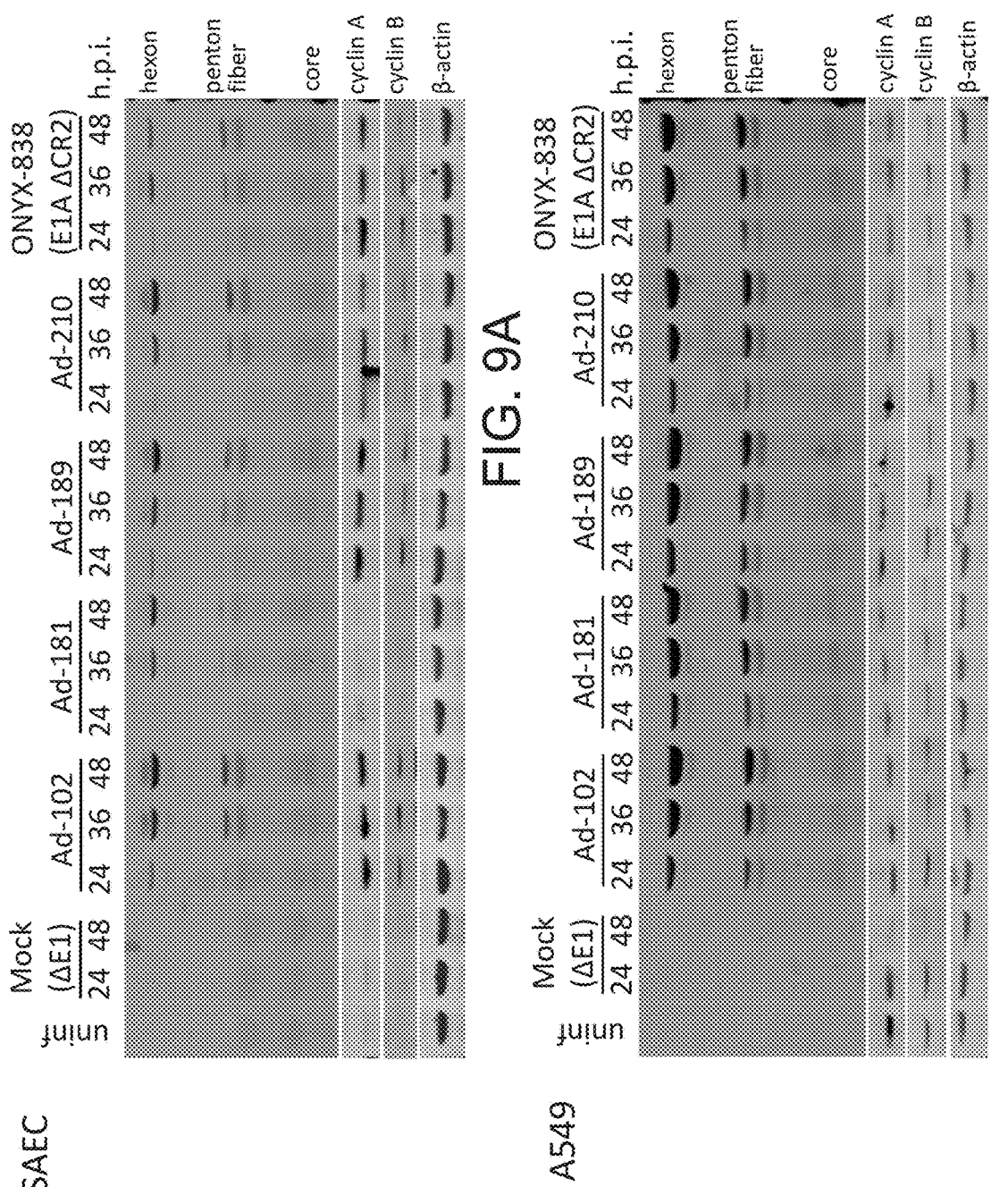
FIGS. 9A and 9B are pictures of immunoblots of cell lysates showing expression of cellular cyclins and adenovirus late protein expression in infected primary and tumor cells. Cells infected with mock (ΔE1), Ad-102 (AdSyn-CO102) (wild type), Ad-181 (AdSyn-CO181) (E1A ΔLXCXE/ΔE4orf6/7), Ad-189 (AdSyn-CO189) (E1A ΔLXCXE), or ONYX-838 (E1A ΔCR2). For FIG. 9A, quiescent human primary small airway epithelial cells (SAEC) were infected at MOI 10. In contrast to wild type and viruses with E1A mutations alone, Ad-181 (AdSyn-CO181) fails to activate E2F dependent cell cycle targets, the S phase, cyclin A and cyclin B. Furthermore, Ad-181 (AdSyn-CO181) and Ad-210 (AdSyn-C0210), which have E4orf6/7 mutations are defective for late protein expression and replication. Both of these defects are apparent to a lesser extent with Ad-210 (AdSyn-C0210). For FIG. 9B, human lung adenocarcinoma cells (A549) were infected at MOI 30. In contrast to infected primary cells, there are no apparent defects in expression of late structural proteins, and cyclin A and cyclin B remain present in all infected A549 samples.
Figures 10A, 10B:
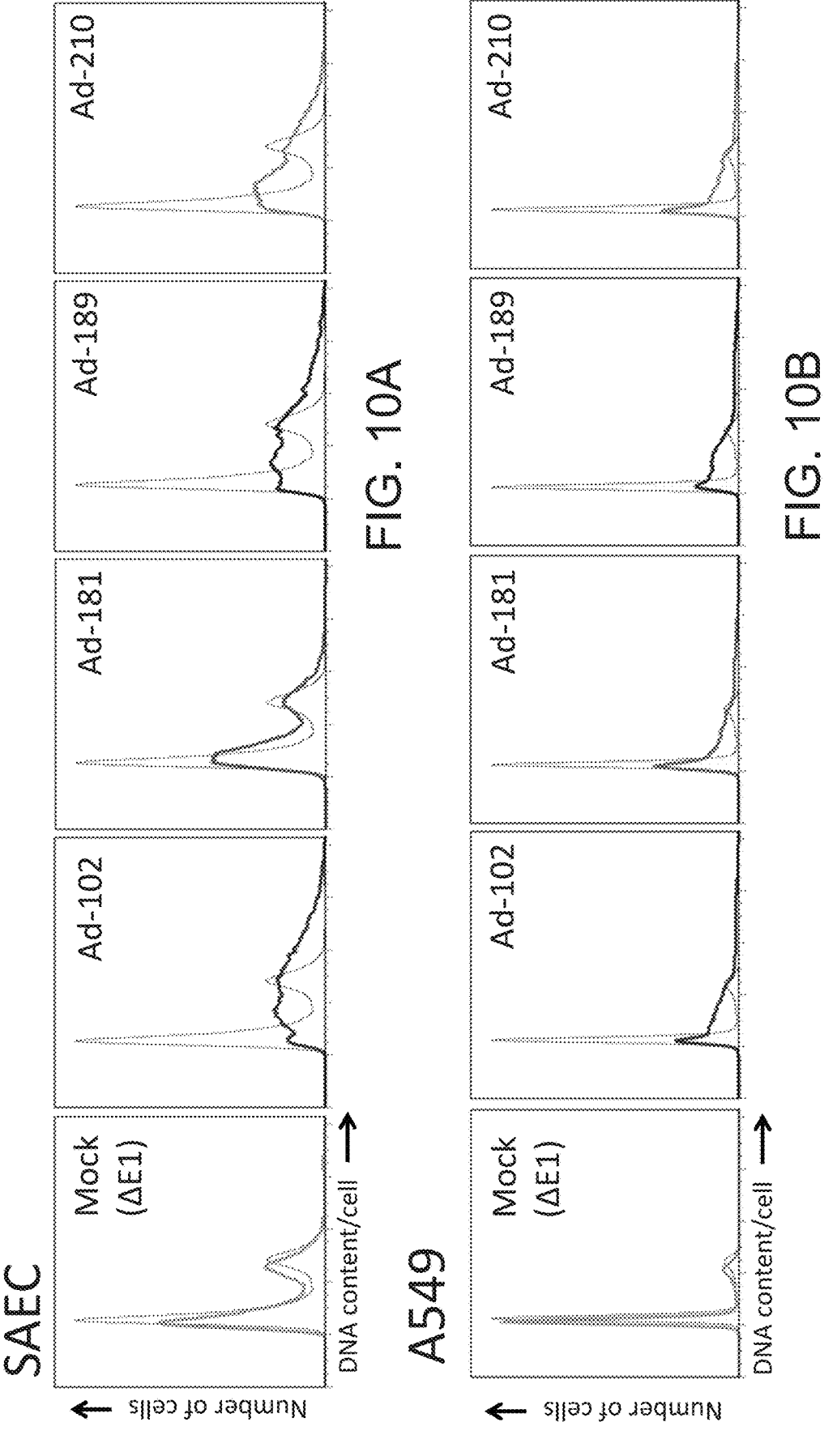
FIGS. 10A and 10B are FACS histograms showing DNA replication quantified with PI by FACS in infected SAEC and A549. Cells were infected with mock (ΔE1), Ad-102 (AdSyn-CO102) (wild type), Ad-181 (AdSyn-CO181) (E1A ΔLXCXE/ΔE4orf6/7), Ad-189 (AdSyn-CO189) (E1A ΔLXCXE), or Ad-210 (AdSyn-C0210) (ΔE4orf6/7), and collected 48 hours post-infection. DNA content of uninfected cells is shown in background profile. The Y-axis is the relative abundance of cells, and the X-axis is the fluorescence from PI in the cell which is proportional to the amount of DNA. For FIG. 10A, quiescent SAEC infected MOI 10. Ad-181 (AdSyn-CO181) infection reveals a strong DNA replication defect in SAEC relative to Ad-102 (AdSyn-CO102), which is linked to decreased virus replication. A modest defect is also apparent in Ad-210 (AdSyn-C0210) infected SAEC at this time point. For FIG. 10B, human lung adenocarcinoma cells (A549) were infected at MOI 30. No DNA replication defect is apparent with any mutant virus infection.
Figures 11A, 11B:
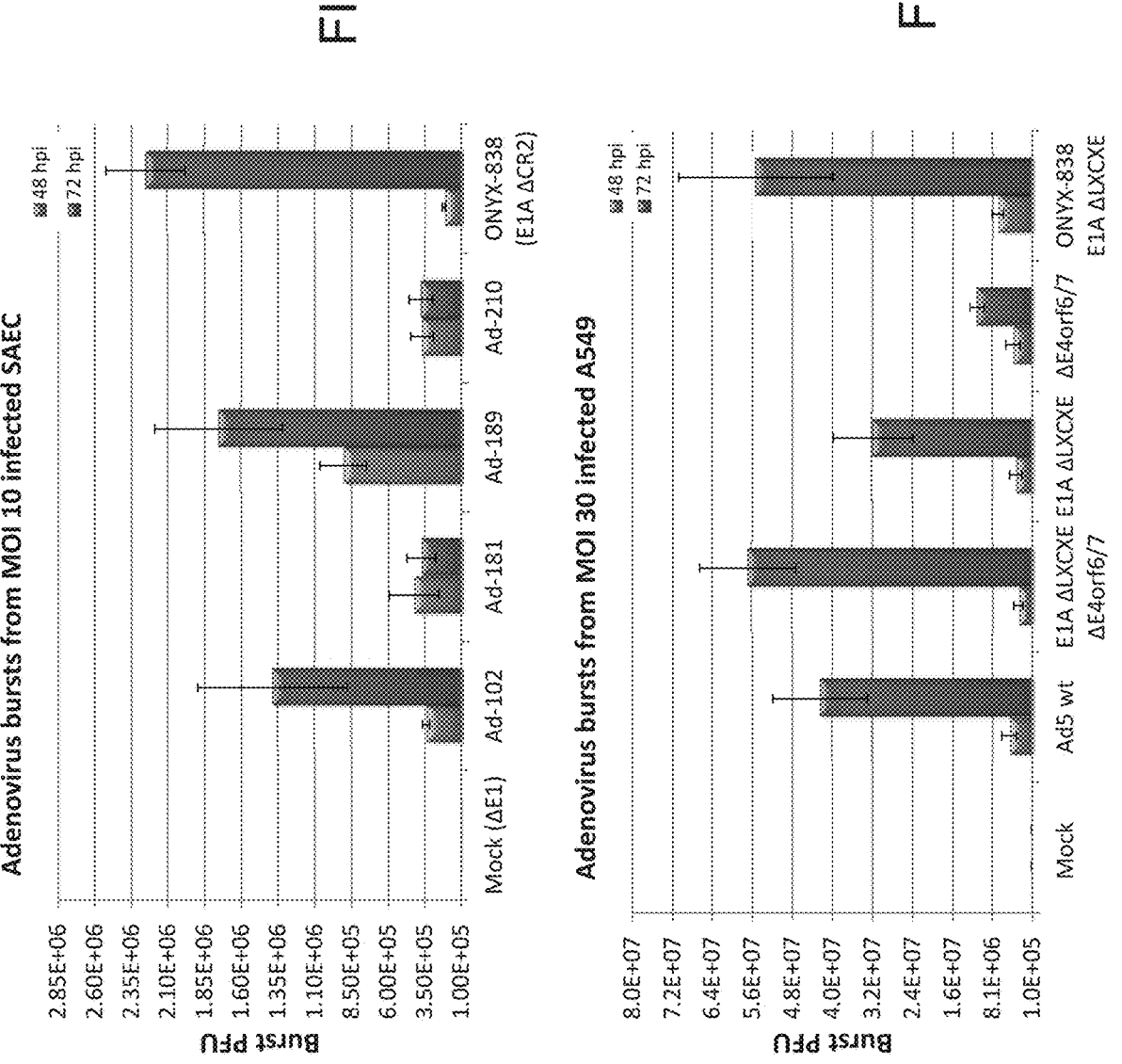
FIGS. 11A and 11B are graphs showing adenovirus bursts from infected SAEC and A549. Cells were infected with mock (ΔE1), Ad-102 (AdSyn-CO102) (wild type), Ad-181 (AdSyn-CO181) (E1A ΔLXCXE/ΔE4orf6/7), Ad-189 (AdSyn-CO189) (E1A ΔLXCXE), Ad-210 (AdSyn-C0210) (ΔE4orf6/7), or ONYX-838 (E1A ΔCR2) and the media was collected 48 and 72 hours post-infection. Infectious virus particles in the media were quantified by ELISA. For FIG. 11A, quiescent SAEC were infected at MOI 10. Both Ad-181 (AdSyn-CO181) and Ad-210 (AdSyn-C0210) infection reveal strong replication defects in SAEC relative to Ad-102 (AdSyn-CO102). For FIG. 11B, A549 cells were infected MOI 30. With the exception of Ad-210 (AdSyn-C0210) at these time points, there is no defect in virus replication.
Figures 12A, 12B:
FIGS. 12A and 12B are graphs showing cell viability of infected SAEC and A549 after 7 days of infection. Cells were infected with a serial dilution of mock (ΔE1), Ad-102 (AdSyn-CO102) (wild type), Ad-181 (AdSyn-CO181) (E1A ΔLXCXE/ΔE4orf6/7), Ad-189 (AdSyn-CO189) (E1A ΔLXCXE), Ad-210 (AdSyn-C0210) (ΔE4orf6/7), or ONYX-838 (E1A ΔCR2) and the cellular metabolic activity was quantified by WST-1 assay (Roche, Basel, Switzerland).
Figures 13A, 13B, 13C:
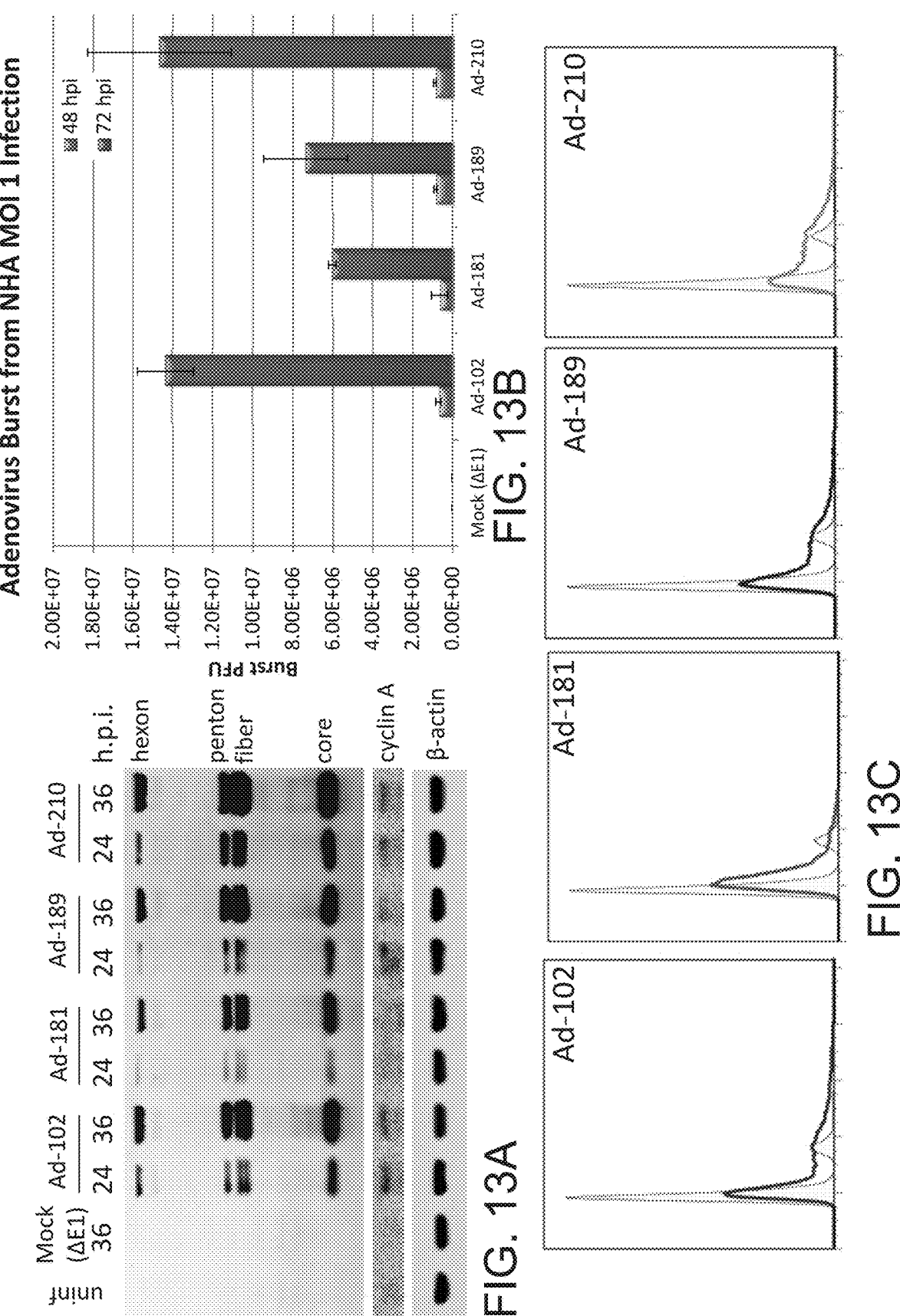
FIG. 13A is a picture of immunoblots of cell lysates and FIGS. 13B and 13C are graphs showing Ad-181 (AdSyn-CO181) has attenuated infection in normal human astrocytes (NHA). For FIG. 13A, MOI 10 infected NHA were subject to immunoblot to detect adenovirus late structural protein expression and cellular cyclin induction. Ad-181 (AdSyn-CO181) does not induce cyclin A, and demonstrates delayed and decreased late viral protein expression relative to Ad-102 (AdSyn-C0102), which are indicative of replication efficiency. For FIG. 13B, NHA was infected by the panel of viruses, and the number of infectious particles in the media was quantified 48 and 72 hours post-infection. Ad-181 (AdSyn-CO181) and Ad-189 (AdSyn-CO189) demonstrate a replication defect in NHA relative to Ad-102 (AdSyn-CO102). For FIG. 13C, DNA replication was quantified in MOI 10 infected NHA 48 hours post-infection by PI FACS. DNA content of uninfected cells is shown in background profile of the histograms. The Y-axis is the relative abundance of cells, and the X-axis is the fluorescence from PI in the cell which is proportional to the amount of nucleic acid. Ad-181 (AdSyn-CO181) demonstrates a diminished induction of DNA replication relative to Ad-102 (AdSyn-CO102), which is linked to decreased virus replication.
Figures 14A, 14B, 14C:
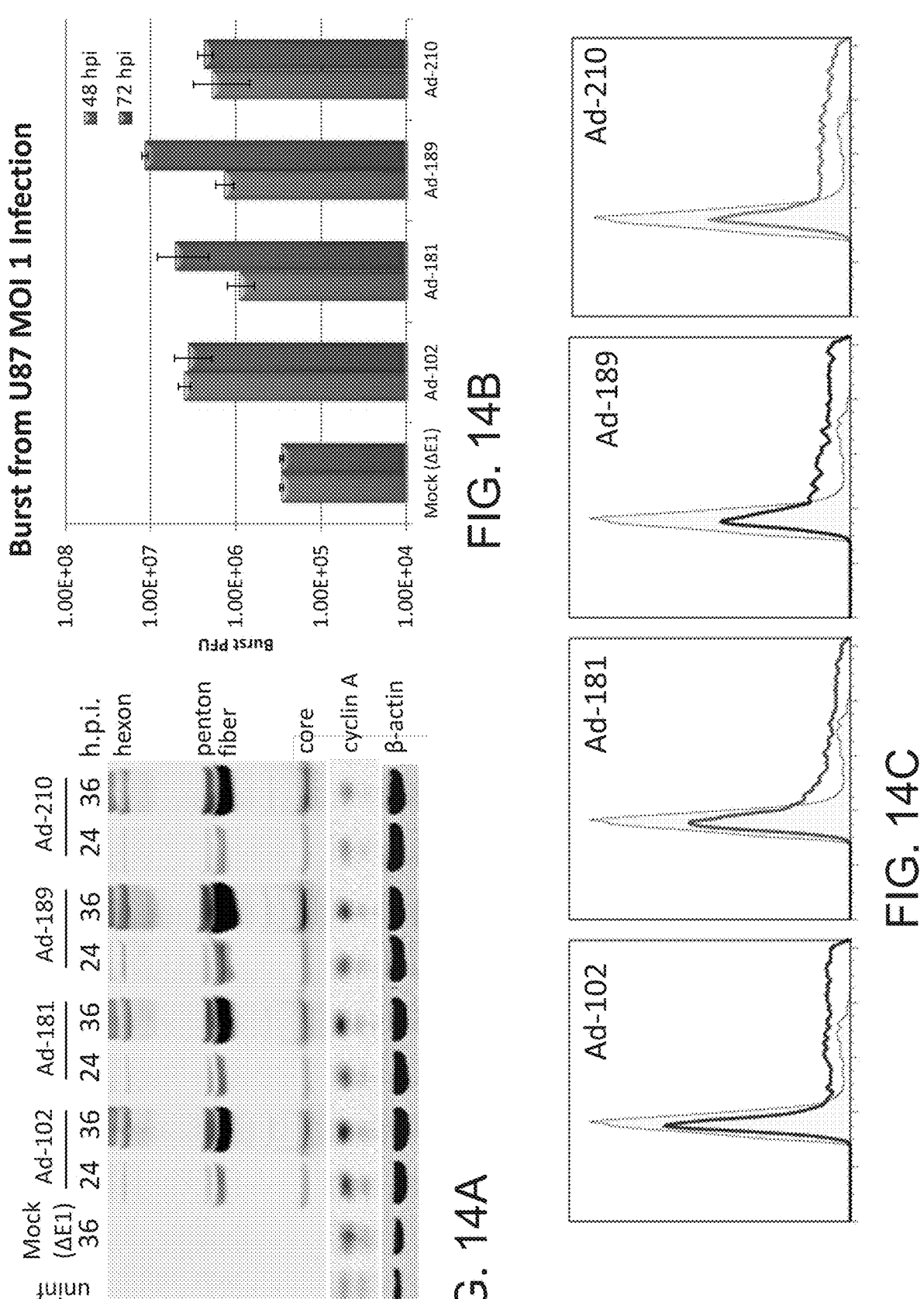
FIG. 14A is a picture of immunoblots of cell lysates from infected glioblastoma U87 cells and FIGS. 14B and 14C are graphs showing mutant Ads have no replication defects in glioblastoma U87 cells. For FIG. 14A, MOI 20 infected U87 cells were subjected to immunoblot to detect adenovirus late structural protein expression and cellular cyclin induction. B) U87 was infected by the panel of viruses, and the number of infectious particles in the media was quantified 48 and 72 hours post-infection. C) DNA replication was quantified in MOI 20 infected U87 48 hours post-infection by PI FACS. DNA content of uninfected cells is shown in background profile of the histograms. The Y-axis is the relative abundance of cells, and the X-axis is the fluorescence from PI in the cell which is proportional to the amount of nucleic acid.
Figures 15A, 15B, 15C:
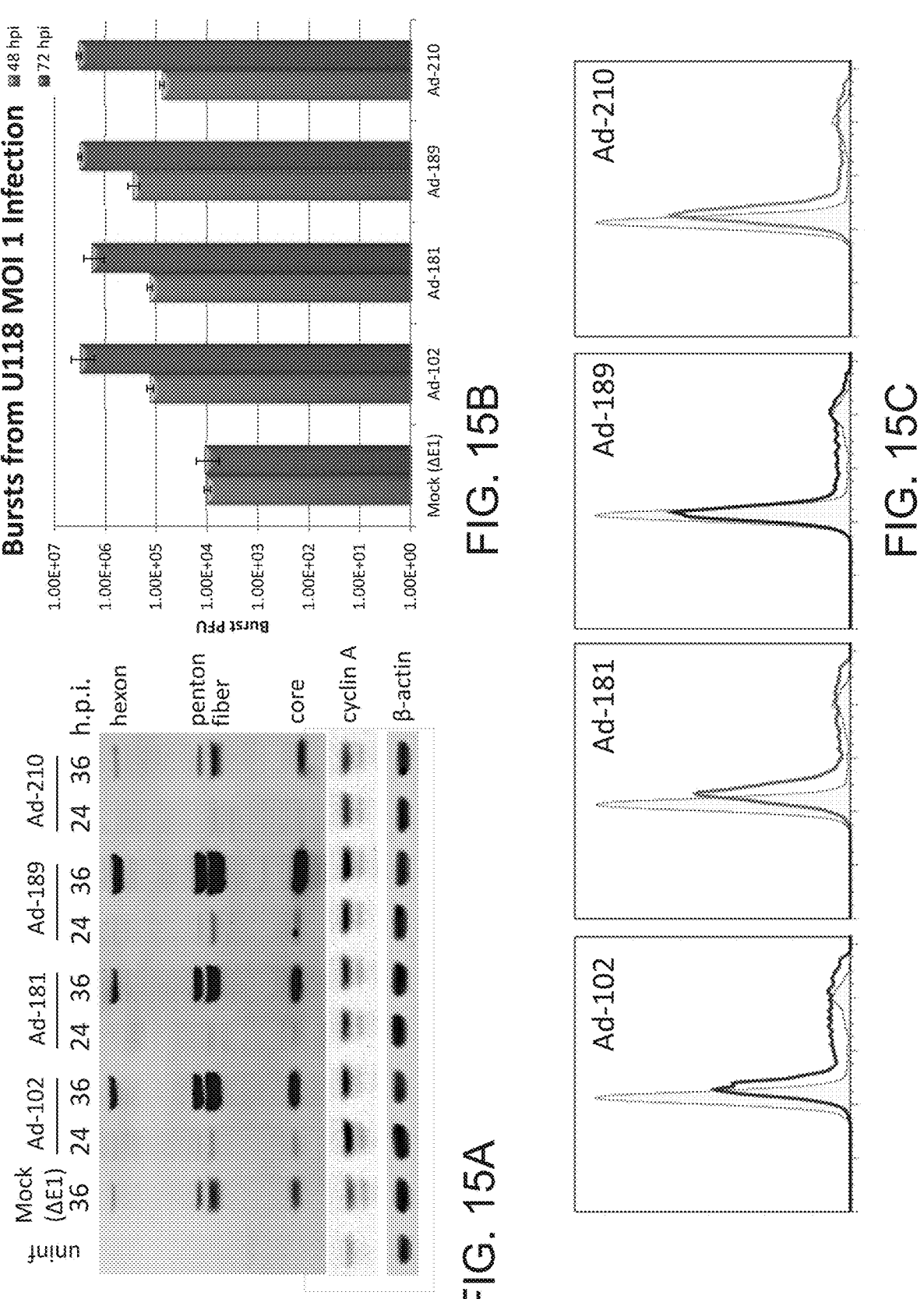
FIG. 15A is a picture of immunoblots of cell lysates from infected glioblastoma U118 cells and FIGS. 15B and 15C are graphs showing mutant Ads have no replication defects in glioblastoma U118 cells. For FIG. 15A, MOI 20 infected U118 cells were subjected to immunoblot to detect adenovirus late structural proteins expression and cellular cyclin induction. B) U87 was infected by the panel of viruses, and the number of infectious particles in the media was quantified 48 and 72 hours post-infection. C) DNA replication was quantified in MOI 20 infected U118 48 hours post-infection by PI FACS. DNA content of uninfected cells is shown in background profile of the histograms. The Y-axis is the relative abundance of cells, and the X-axis is the fluorescence from PI in the cell which is proportional to the amount of nucleic acid.
Figures 16A, 16B, 16C:
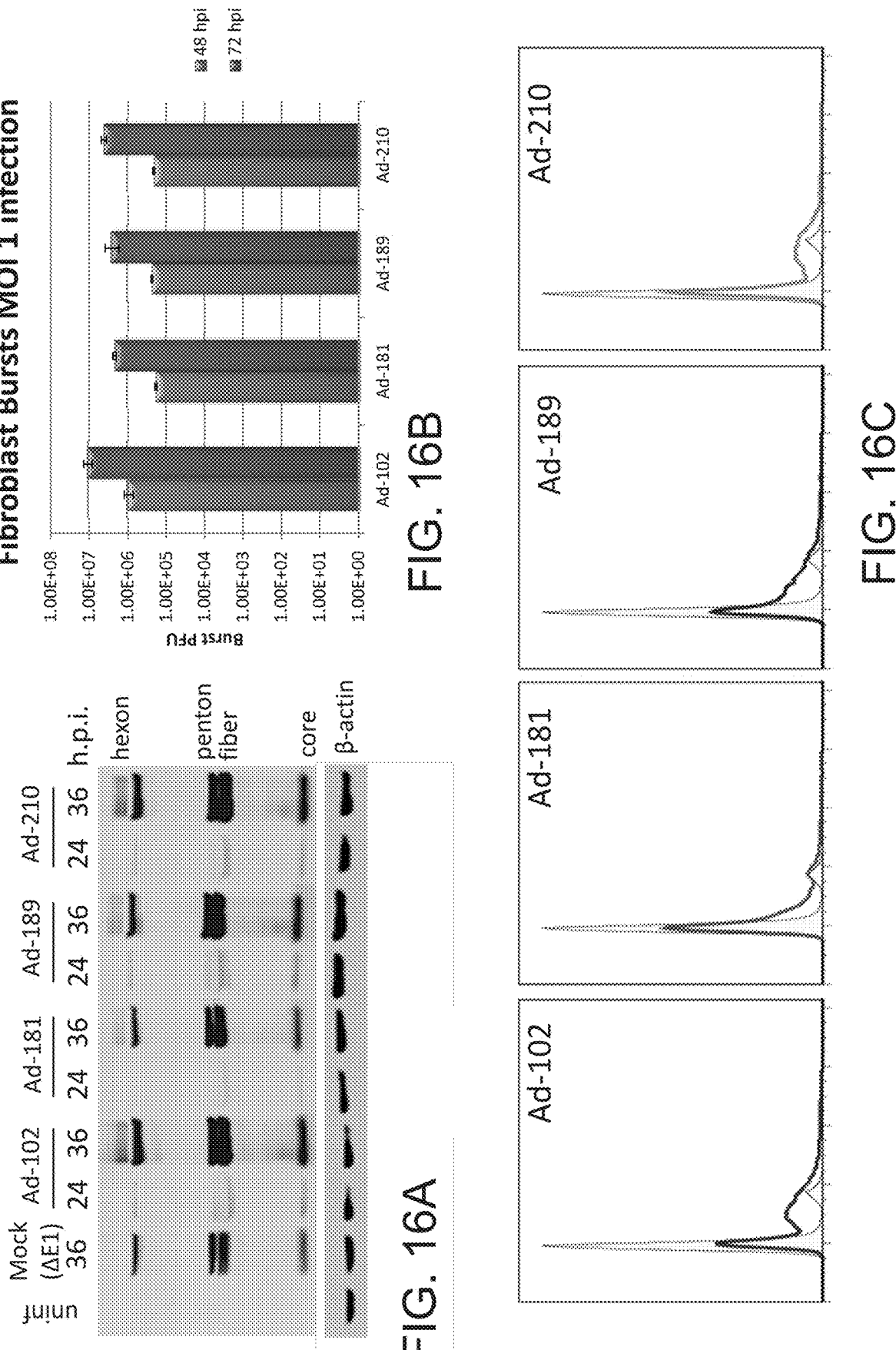
FIG. 16A is a picture of a gel and FIGS. 16B and 16C are graphs showing Ad-181 (AdSyn-CO181) has modest replication defects in human fibroblasts (IMR90). For FIG. 16A, MOI 10 infected fibroblasts were subjected to immunoblot to detect late structural protein expression. Ad-181 (AdSyn-CO 181) demonstrates delayed and decreased late viral protein expression relative to Ad-102 (AdSyn-CO102), which are indicative of replication efficiency. For FIG. 16B, fibroblasts were infected by the panel of viruses, and the number of infectious particles in the media was quantified 48 and 72 hours post-infection. With this assay at these time points, there was not a clear difference in replication capacity of the mutant adenoviruses. For FIG. 16C, DNA replication was quantified in MOI 20 infected fibroblasts 48 hours post-infection by PI FACS. DNA content of uninfected cells is shown in background profile of the histograms. The Y-axis is the relative abundance of cells, and the X-axis is the fluorescence from PI in the cell which is proportional to the amount of nucleic acid. Ad-181 (AdSyn-CO181) demonstrates a diminished induction of DNA replication relative to Ad-102 (AdSyn-CO102), which is linked to decreased virus replication.

To test these viruses, cells infected with mock (ΔE1), Ad-102 (AdSyn-CO102) (wild type), Ad-181 (AdSyn-CO181) (E1A ΔLXCXE/ΔE4orf6/7), Ad-189 (AdSyn-CO189) (E1A ΔLXCXE), or ONYX-838 (E1A ΔCR2). ONYX-838 also lacks ΔLXCXE which is in the CR2 domain of E1A. Quiescent human primary small airway epithelial cells (SAEC) were infected at MOI 10. Ad-102 (AdSyn-CO102) shows expected decrease of E1A levels at later times during infection (FIG. 8A). Similarly Ad-189 (AdSyn-CO189) and ONYX-838 show a decrease of E1A levels at later times during infection, but have stronger expression at the earlier time point. Ad-181 (AdSyn-CO181) shows stronger and continued expression of E1A throughout the infection, which is indicative of failure to progress through the adenovirus lifecycle. Confluent lung adenocarcinoma cells (A549) were infected at MOI 30. All infections show expected decrease of E1A levels at later times during infection, indicative of typical adenovirus lifecycle progression (FIG. 8B). Testing of adenovirus late protein and cyclin expression of the mutant adenoviruses in infected cells is shown in FIG. 9. There are no apparent defects in expression of late structural proteins, and cyclin remains present in all infected A549 samples. DNA replication of infected SAEC and A549 cells is shown in FIG. 10. No DNA replication defect is apparent with any mutant virus infection. FIG. 11 shows adenovirus bursts from infected SAEC and A549. With the exception of Ad-210 (AdSyn-C0210) at these time points with this burst assay, there is no defect in virus replication. FIG. 12 shows the cell viability of infected SAEC and A549 after 7 days of infection. Of the viruses there is no defect in cell killing by mutant viruses relative to wild type. FIG. 13 shows that the mutant viruses do have attenuated infection in normal human astrocytes (NHA)

which FIGS. 14 and 15 show that the mutant adenoviruses have no replication defects in glioblastoma U87 and U118 cells, respectively.

Thus, the data show that, in contrast to wild type and E1AΔCR2 viruses, E1AΔCR2/ΔE4orf6/7 and also ΔE4orf6/7 viruses replicate poorly in primary cells as evidenced by lack of capsid protein expression, failure to induce the E2F target genes-Cyclin A and B, failure to elicit S phase entry and viral replication. See, e.g., FIGS. 9, 10, and 11. In contrast, these viruses replicate to wild type (WT) virus levels in A549 cells and a panel of tumor cell-lines. Therefore, the provided adenoviruses are selective cancer therapeutic agents.

Figure 17:
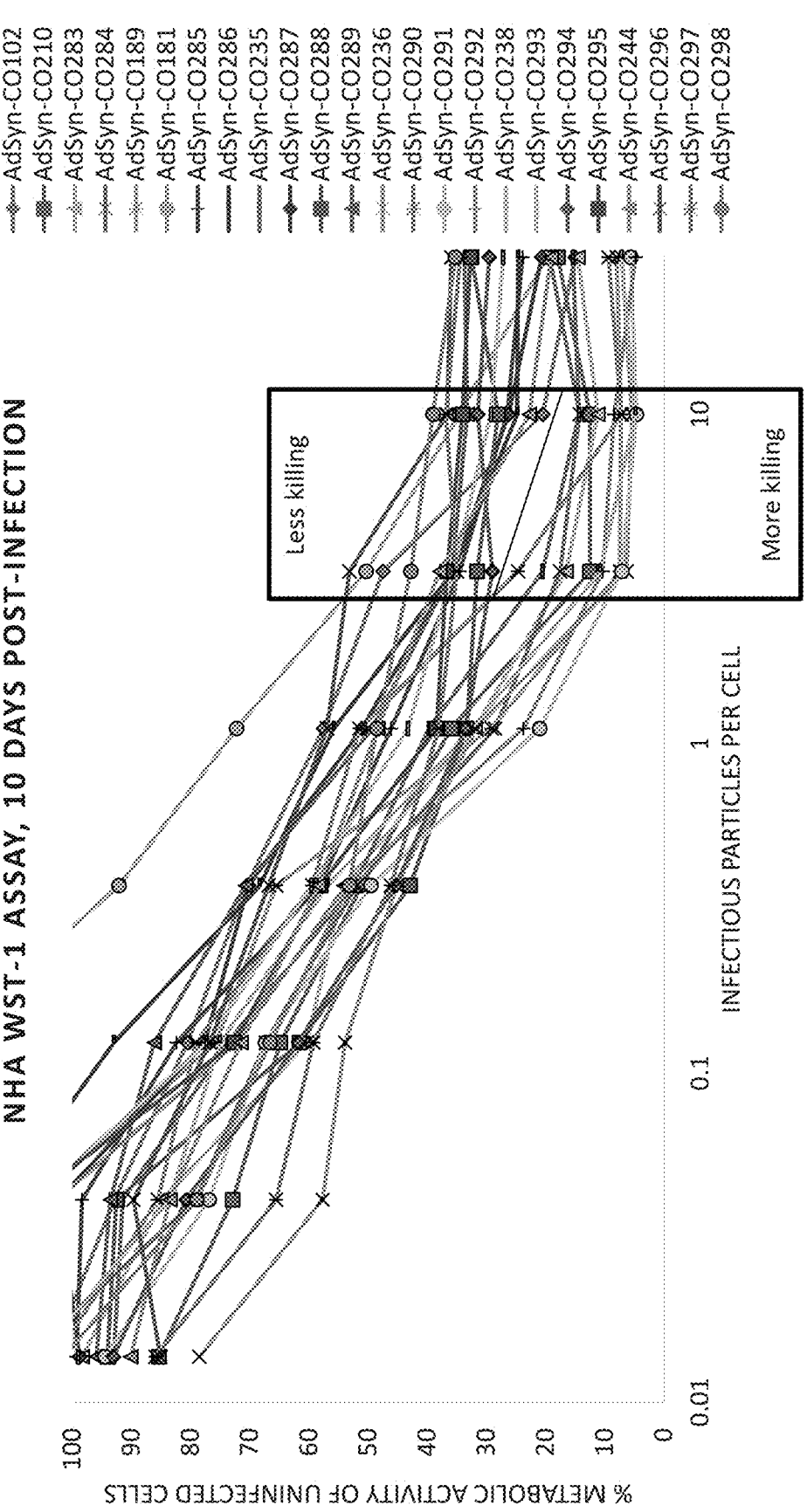
FIG. 17 is a graph showing the cell viability of infected primary normal human astrocyte cells (NHA) after 10 days of infection. Cells were infected with a serial dilution of wt and mutant viruses (see Table 1 below). The metabolic activity was quantified by WST-1 assay (Roche, Basel, Switzerland). The viability of cells at three and ten infectious particles per cell show a separation of cell killing by viruses into two groups, less and more killing. The group of viruses that exhibit less killing bear both an E1A with an Rb-binding mutation and deletion of E4orf6/7. The group of viruses the exhibit more killing either have a wild type E1 or wild type E4.
Figure 18:
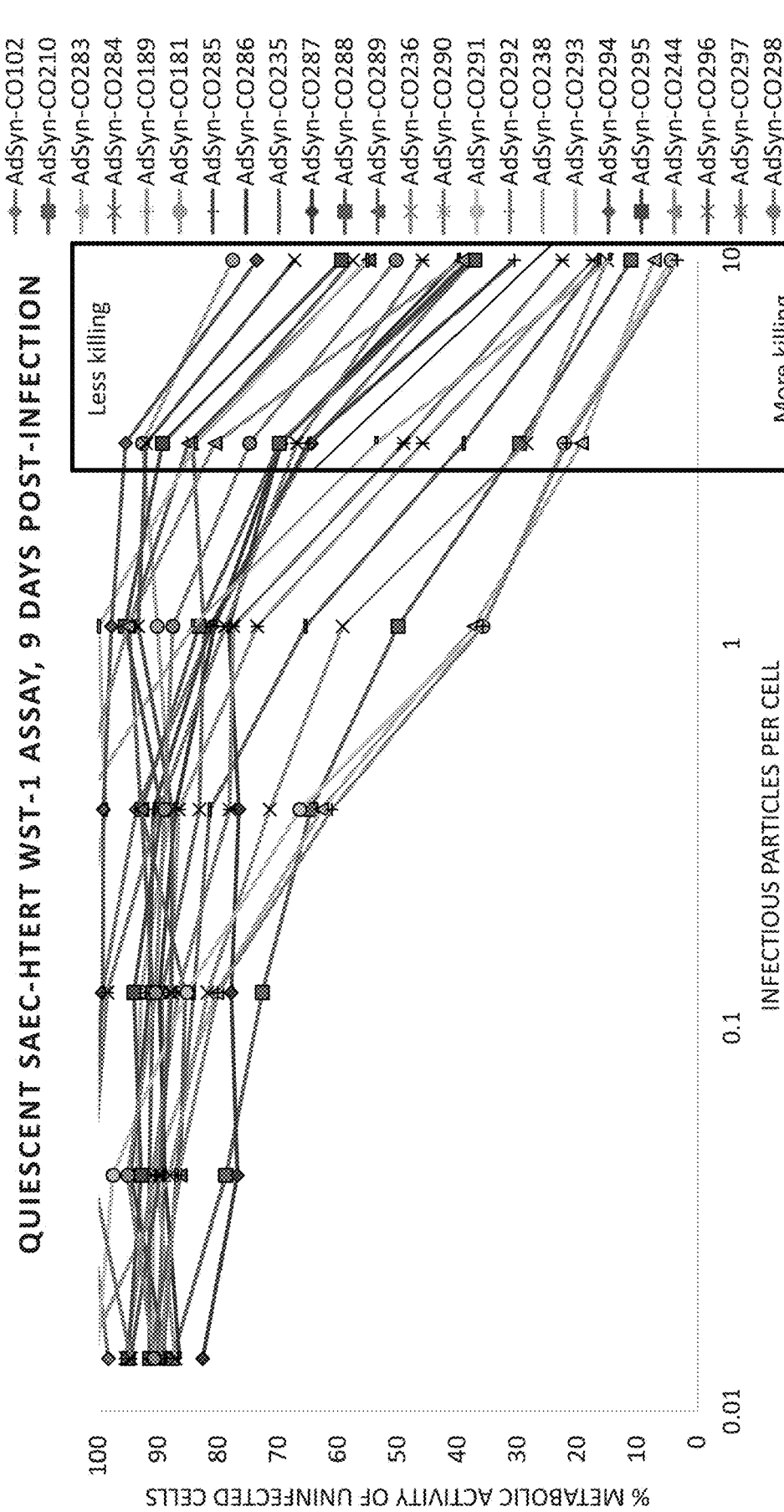
FIG. 18 is a graph showing the cell viability of infected quiescent SAEC-hTERT cells after 9 days of infection. Cells were infected with a serial dilution of wt and mutant viruses (see Table 1 below). The metabolic activity was quantified by WST-1 assay (Roche, Basel, Switzerland). The viability of cells at three and ten infectious particles per cell show a separation of cell killing by viruses into two groups, less and more killing. The group of viruses that exhibit less killing bear both an E1A with an Rb-binding mutation and deletion of E4orf6/7. The group of viruses the exhibit more killing either have a wild type E1 or wild type E4.
Figure 19:
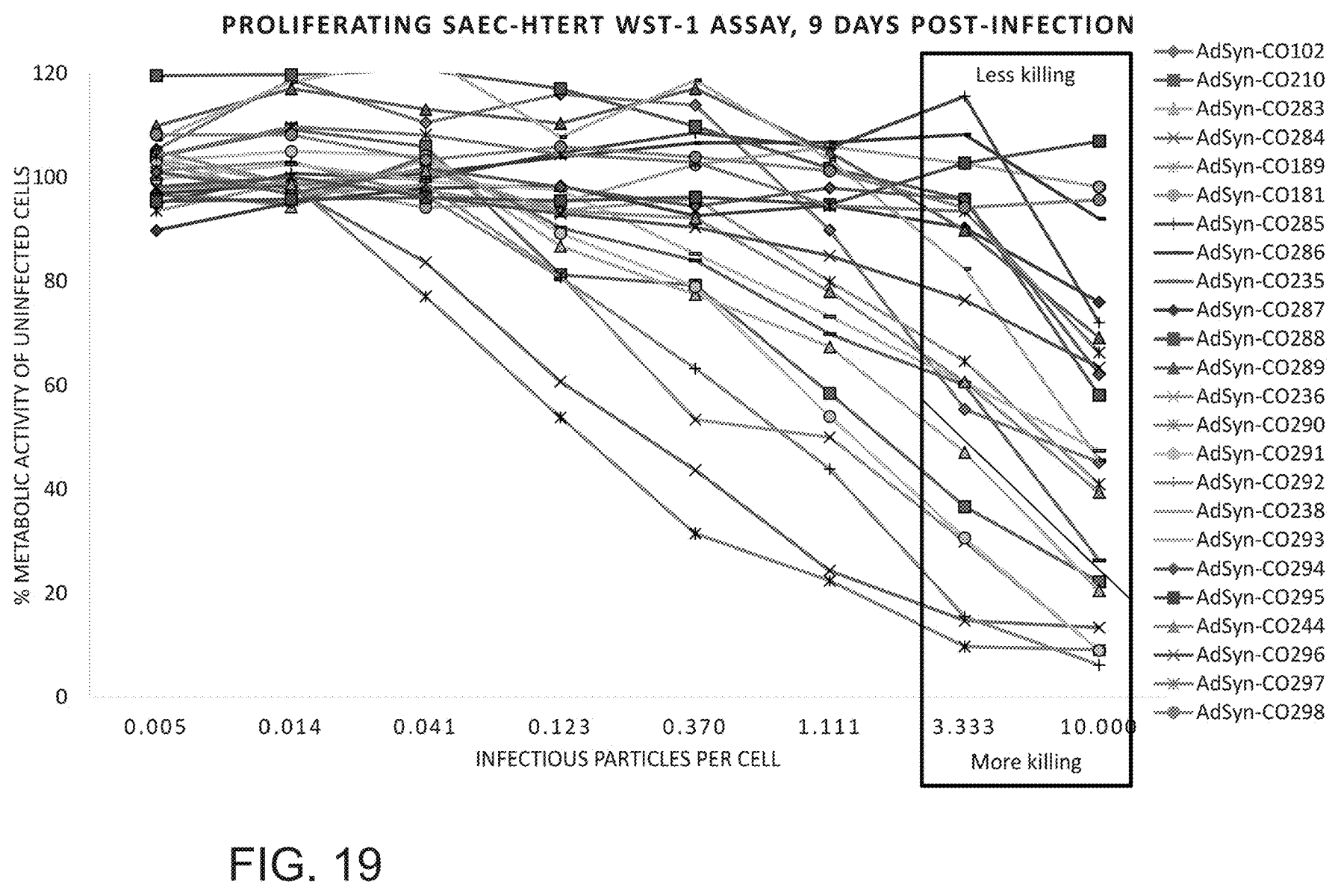
Figure 20:
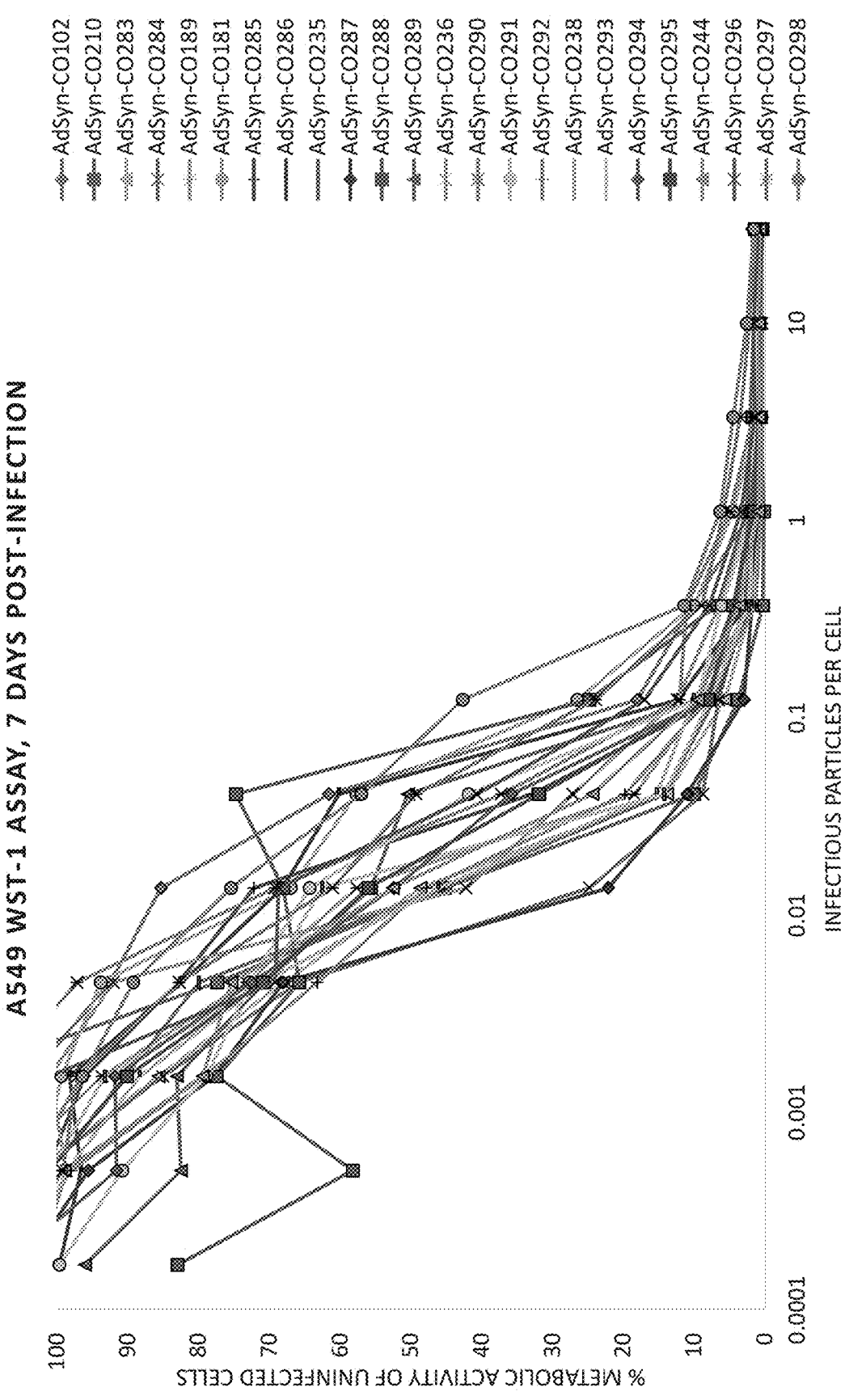
FIG. 20 is a graph showing the cell viability of infected A549 cells after 7 days of infection. Cells were infected with a serial dilution of wt and mutant viruses (see Table 1 below). The metabolic activity was quantified by WST-1 assay (Roche, Basel, Switzerland).
Figure 21:
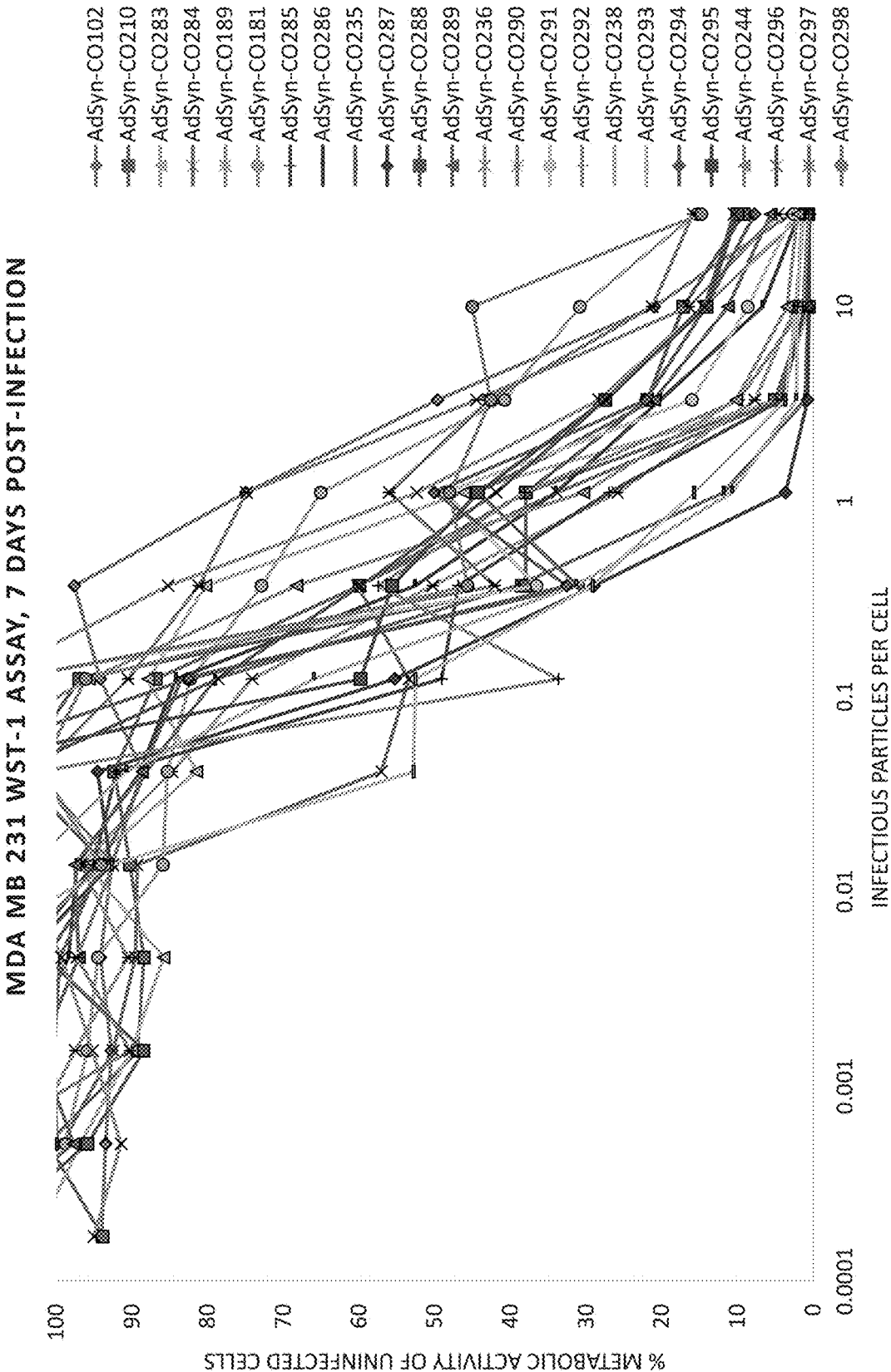
FIG. 21 is a graph showing the cell viability of infected human breast cancer cells (MDA MB 231) after 7 days of infection. Cells were infected with a serial dilution of wt and mutant viruses (see Table 1 below). The metabolic activity was quantified by WST-1 assay (Roche, Basel, Switzerland).
Figure 22:
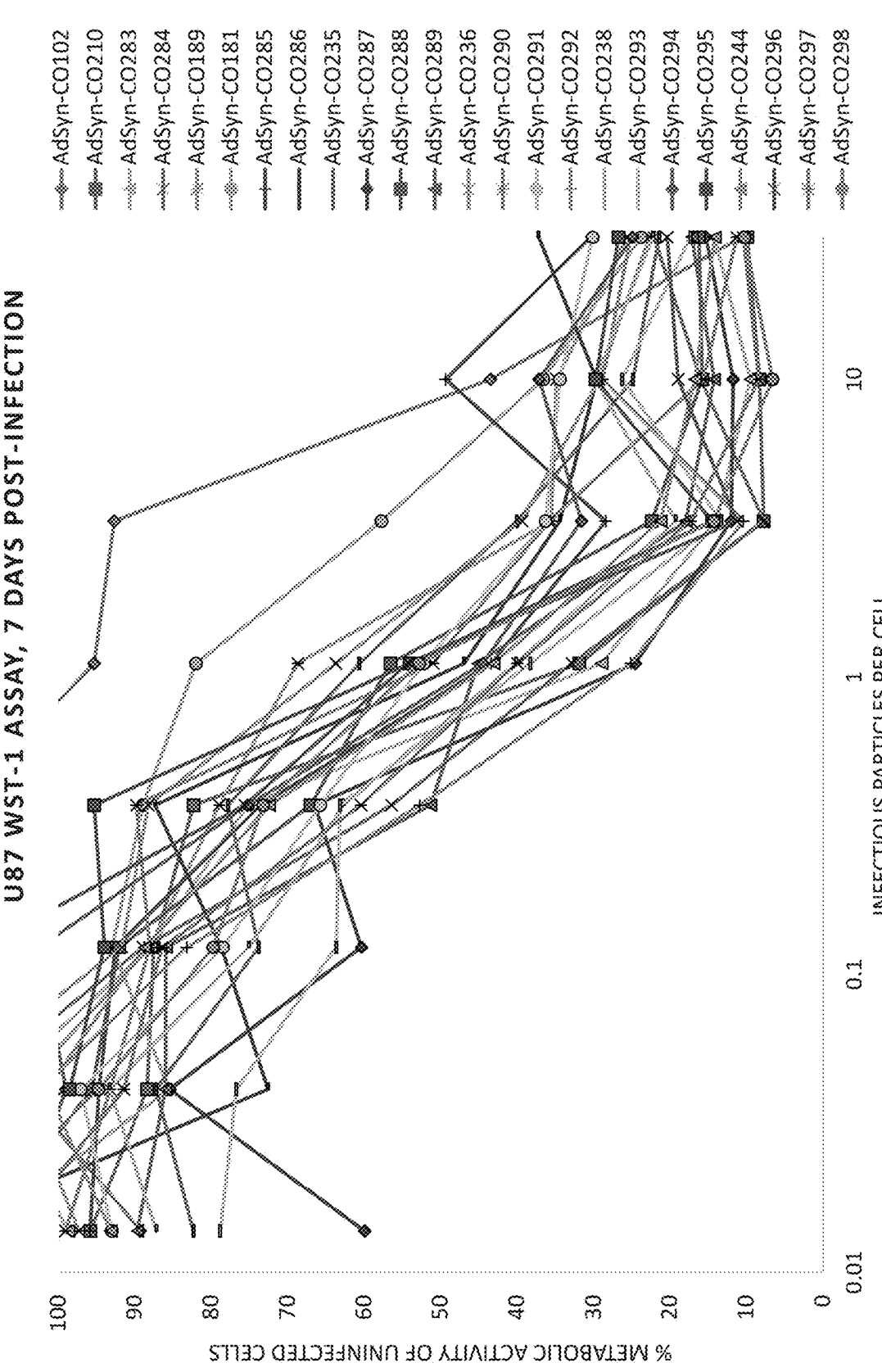
FIG. 22 is a graph showing the cell viability of infected glioblastoma cells (U87) after 7 days of infection. Cells were infected with a serial dilution of wt and mutant viruses (see Table 1 below). The metabolic activity was quantified by WST-1 assay (Roche, Basel, Switzerland).
Figure 23:
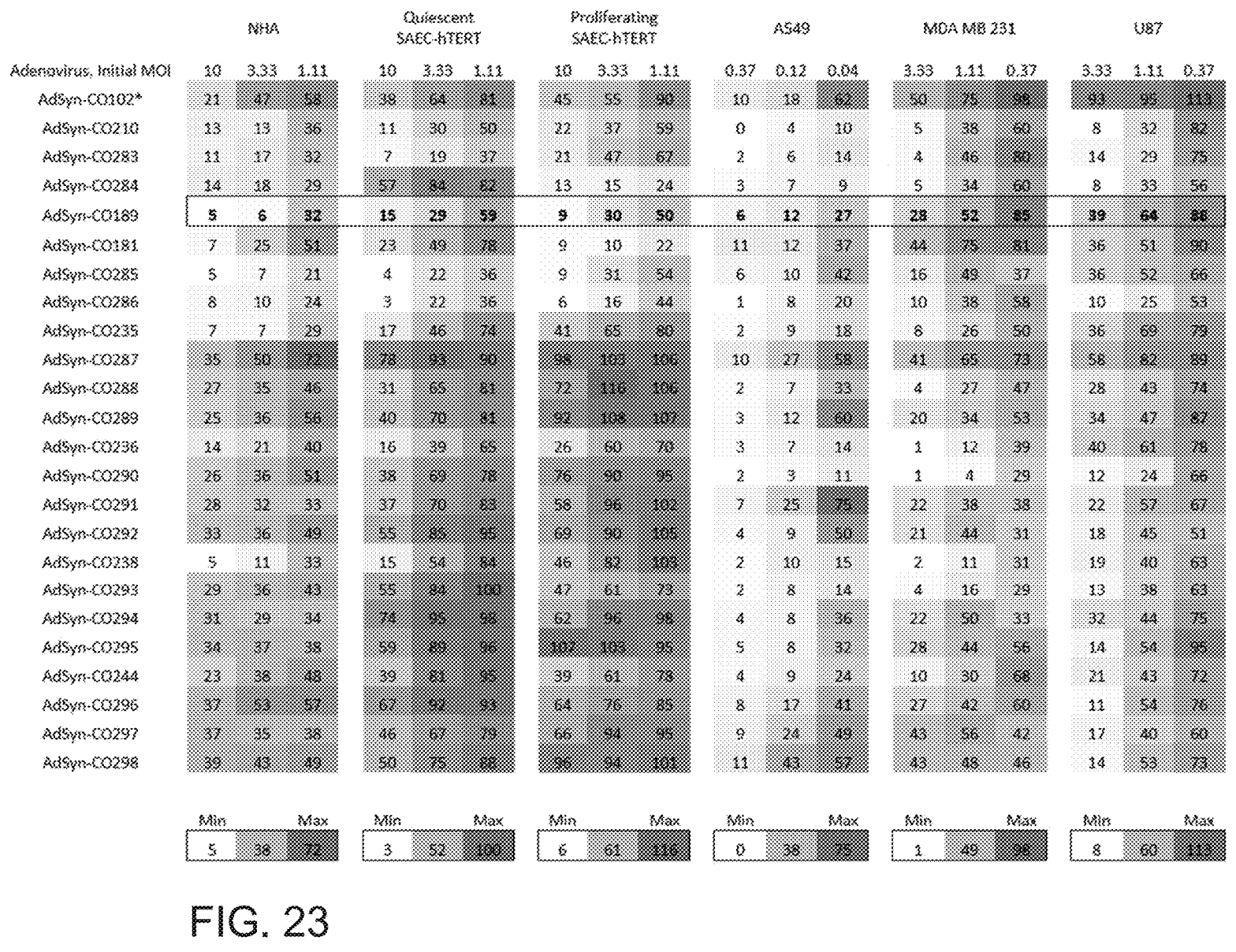
Figure 24:
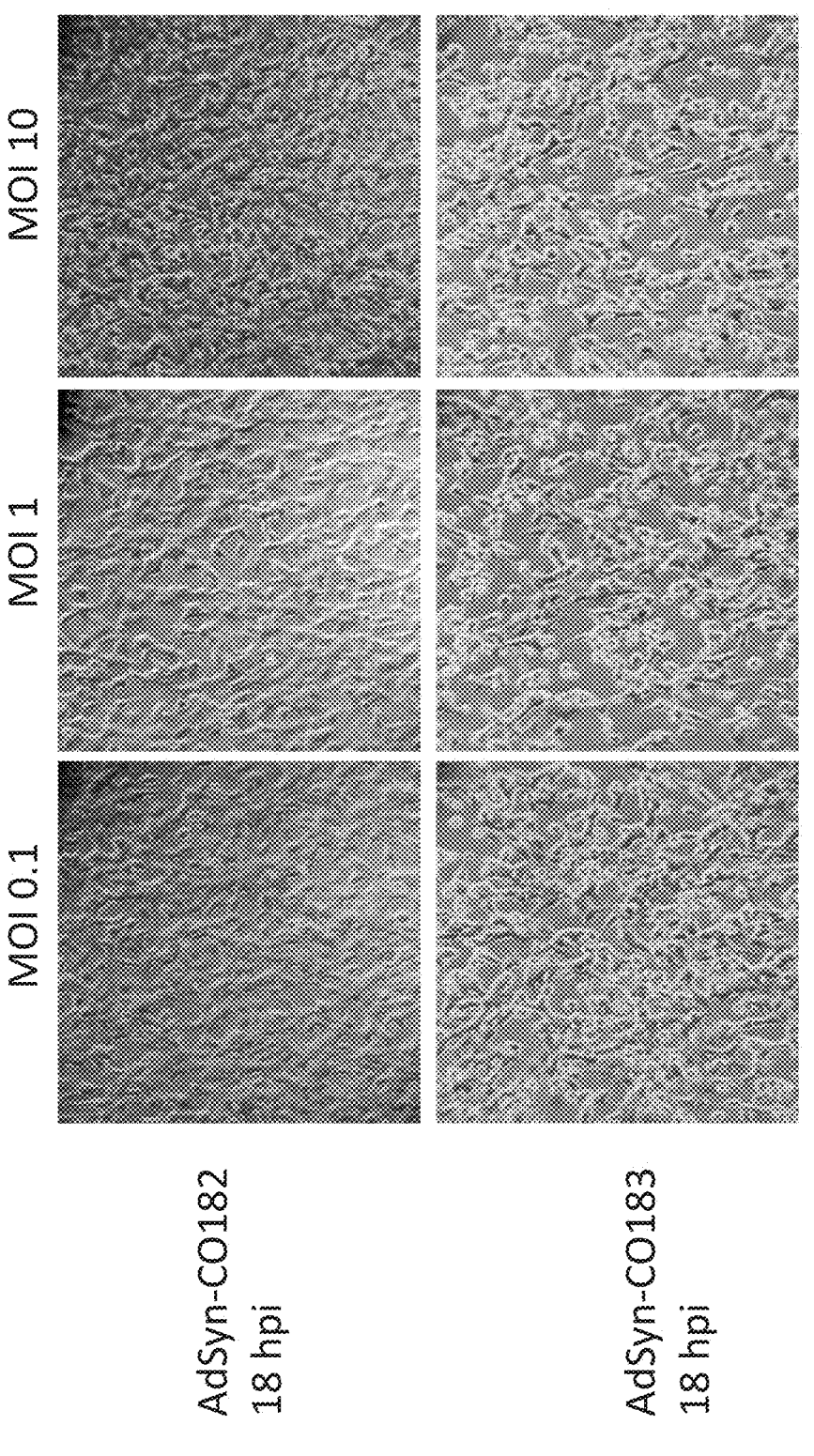
FIG. 24 shows CPE microscopy images of 293 cells infected with AdSyn-CO182 and AdSyn-CO183. Both AdSyn-CO182 and AdSyn-CO183 bear the E1A ΔLXCXE and ΔE4orf6/7 mutations, and additionally bear an insertion in the E3-12.5K ORF. In AdSyn-CO182, the E3-12.5K ORF is replaced by a sequence encoding fluorescent protein mCherry. In AdSyn-CO183, the E3-12.5K ORF is replaced by a sequence encoding a non-cleavable FasL, which signals for apoptosis.

Results of the replication specificity of the larger set of mutant adenoviruses, including mutations in E4orf1 (see Table 1) are shown in FIGS. 17-22 and summarized in FIG. 23. FIG. 17 is a graph showing the cell viability of infected primary normal human astrocytes (NHA) after 10 days of infection. FIG. 18 is a graph showing the cell viability of infected quiescent normal small airway epithelial cells (SAEC-hTERT) after 9 days of infection. FIG. 19 is a graph showing the cell viability of infected proliferating SAEC-hTERT cells after 10 days of infection. FIG. 20 is a graph showing the cell viability of infected human lung adenocarcinoma cells (A549) after 7 days of infection. FIG. 21 is a graph showing the cell viability of infected human breast cancer cells (MDA MB 231) after 7 days of infection. FIG. 22 is a graph showing the cell viability of infected glioblastoma cells (U87) after 7 days of infection. FIG. 23 is a heatmap table showing the quantitation of cell viability assays for infected primary NHA, SAEC-hTERT (quiescent), SAEC-hTERT (proliferating), A549, MDA MB 231, and U87 cells after 7 days of infection. These data show that the combination of various modifications of E1A and E4orf6/7 results in selective oncolytic adenovirus that specifically replicate in cancer cells with a defective Rb tumor suppressor pathway.

EMBODIMENTS

Embodiment 1. An adenovirus comprising an E1A polypeptide comprising one or more modifications and comprising an E4orf6/7 polypeptide comprising one or more modifications.

Embodiment 2. The adenovirus of embodiment 1, wherein the E1A polypeptide comprises a modification in an Rb binding site of E1A.

Embodiment 3. The adenovirus of embodiment 1, wherein the E1A polypeptide comprises two Rb binding sites and wherein the E1A polypeptide comprises a modification in both Rb binding sites.

Embodiment 4. The adenovirus of embodiment 1, wherein the E1A polypeptide comprises a modification in one or more of amino acid residues 120-130 of the E1A polypeptide.

Embodiment 5. The adenovirus of embodiment 1, wherein the E1A polypeptide comprises a modification in one or more of amino acid residues 122-126 of the E1A polypeptide.

Embodiment 6. The adenovirus of any one of embodiments 1-5, wherein the E1A polypeptide comprises a modification in one or more of amino acid residues 35-55 of the E1A polypeptide.

Embodiment 7. The adenovirus of any one of embodiments 1-6, wherein the E1A polypeptide comprises a modification in one or more of amino acid residues 37-49 of the E1A polypeptide.

Embodiment 8. The adenovirus of any one of embodiments 1-7, wherein the E1A polypeptide comprises a deletion.

Embodiment 9. The adenovirus of embodiment 8, wherein the deletion is a deletion of amino acid residues 122-126 of the E1A polypeptide.

Embodiment 10. The adenovirus of embodiment 8, wherein the deletion is a deletion of amino acid residues 2-11 of the E1A polypeptide.

Embodiment 11. The adenovirus of embodiment 1, wherein the E1A polypeptide comprises the deletion ΔLXCXE.

Embodiment 12. The adenovirus of any one of embodiments 1-11, wherein the E1A polypeptide comprises one or more substitutions.

Embodiment 13. The adenovirus of embodiment 12, wherein the E1A polypeptide comprises a substitution at residue Y47, residue C124 or at both residues Y47 and C124.

Embodiment 14. The adenovirus of embodiment 12, wherein the E1A polypeptide comprises the substitution Y47H.

Embodiment 15. The adenovirus of embodiment 12, wherein the E1A polypeptide comprises the substitution C124G.

Embodiment 16. The adenovirus of embodiment 12, wherein the E1A polypeptide comprises the substitution Y47H and C124G.

Embodiment 17. The adenovirus of any one of embodiments 12-16, wherein the E1A polypeptide further comprises a deletion of amino acid residues 2-11.

Embodiment 18. The adenovirus of embodiment 1, wherein the E1A polypeptide comprises a deletion of amino acid residues 122-126 of E1A and a substitution at residue Y47.

Embodiment 19. The adenovirus of any one of embodiments 1-18, wherein the E1A polypeptide comprises SEQ ID NO: 1.

Embodiment 20. The adenovirus of any one of embodiments 1-18, wherein the E1A polypeptide comprises SEQ ID NO: 2.

Embodiment 21. The adenovirus of any one of embodiments 1-20, wherein the E4orf6/7 polypeptide comprises a modification in one or both of the E4orf6/7 exons.

Embodiment 22. The adenovirus of any one of embodiments 1-20, wherein the E4orf6/7 polypeptide comprises a deletion of one or both of the E4orf6/7 exons.

Embodiment 23. The adenovirus of any one of embodiments 1-22, wherein the E4orf6/7 polypeptide comprises SEQ ID NO: 3.

Embodiment 24. The adenovirus of any one of embodiments 1-22, wherein the E4orf6/7 polypeptide comprises SEQ ID NO: 4.

Embodiment 25. The adenovirus of any one of embodiments 1-24, further comprising an E4orf1 polypeptide comprising one or more modifications.

Embodiment 26. The adenovirus of embodiment 25, wherein the E4orf1 polypeptide comprises one or more deletions.

Embodiment 27. The adenovirus of embodiment 25, wherein the E4orf1 polypeptide comprises a deletion in the C-terminal region of E4orf1.

Embodiment 28. The adenovirus of embodiment 25, wherein the E4orf1 polypeptide comprises a deletion of residues 125-128 of the E4orf1 polypeptide.

Embodiment 29. The adenovirus of any one of embodiments 25-28, wherein the E4orf1 polypeptide comprises SEQ ID NO: 5.

Embodiment 30. An adenovirus comprising an E1A polypeptide comprising one or more modifications and comprising an E4orf1 polypeptide comprising one or more modifications.

Embodiment 31. The adenovirus of embodiment 30, wherein the E4orf1 polypeptide comprises one or more deletions.

Embodiment 32. The adenovirus of embodiment 31, wherein the E4orf1 polypeptide comprises a deletion in the C-terminal region of E4orf1.

Embodiment 33. The adenovirus of embodiment 31, wherein the E4orf1 polypeptide comprises a deletion of residues 125-128 of the E4orf1 polypeptide.

Embodiment 34. The adenovirus of any one of embodiments 30-33, wherein the E1A polypeptide comprises a modification in an Rb binding site of E1A.

Embodiment 35. The adenovirus of embodiment 34, wherein the E1A polypeptide comprises two Rb binding sites and wherein the E1A polypeptide comprises a modification in both Rb binding sites.

Embodiment 36. The adenovirus of any one of embodiments 30-33, wherein the E1A polypeptide comprises a modification in one or more of amino acid residues 120-130 of the E1A polypeptide.

Embodiment 37. The adenovirus of any one of embodiments 30-33, wherein the E1A polypeptide comprises a modification in one or more of amino acid residues 122-126 of the E1A polypeptide.

Embodiment 38. The adenovirus of any one of embodiments 30-33, wherein the E1A polypeptide comprises a modification in one or more of amino acid residues 35-55 of the E1A polypeptide.

Embodiment 39. The adenovirus of any one of embodiments 30-33, wherein the E1A polypeptide comprises a modification in one or more of amino acid residues 37-49 of the E1A polypeptide.

Embodiment 40. The adenovirus of any one of embodiments 30-33, wherein the E1A polypeptide comprises a deletion.

Embodiment 41. The adenovirus of embodiment 40, wherein the deletion is a deletion of amino acid residues 122-126 of the E1A polypeptide.

Embodiment 42. The adenovirus of embodiment 40, wherein the deletion is a deletion of amino acid residues 2-11 of the E1A polypeptide.

Embodiment 43. The adenovirus of any one of embodiments 30-33, wherein the E1A polypeptide comprises the deletion ΔLXCXE.

Embodiment 44. The adenovirus of any one of embodiments 30-33, wherein the E1A polypeptide comprises one or more substitutions.

Embodiment 45. The adenovirus of embodiment 44, wherein the E1A polypeptide comprises a substitution at residue Y47, residue C124 or both Y47 and C124.

Embodiment 46. The adenovirus of embodiment 44, wherein the E1A polypeptide comprises the substitution Y47H.

Embodiment 47. The adenovirus of embodiment 44, wherein the E1A polypeptide comprises the substitution C124G.

Embodiment 48. The adenovirus of embodiment 44, wherein the E1A polypeptide comprises the substitution Y47H and C124G.

Embodiment 49. The adenovirus of any one of embodiments 44-48, wherein the E1A polypeptide further comprises a deletion of amino acid residues 2-11.

Embodiment 50. The adenovirus of any one of embodiments 30-33, wherein the E1A polypeptide comprises a deletion of amino acid residues 122-126 of E1A and a substitution at residue Y47.

Embodiment 51. The adenovirus of any one of embodiments 30-50, wherein the E1A polypeptide comprises SEQ ID NO: 1.

Embodiment 52. The adenovirus of any one of embodiments 30-50, wherein the E1A polypeptide comprises SEQ ID NO: 2.

Embodiment 53. The adenovirus of any one of embodiments 1-52, wherein the adenovirus selectively replicates in Rb-deficient cells.

Embodiment 54. A pharmaceutical composition comprising the adenovirus of any one of embodiments 1-53 and a pharmaceutically acceptable carrier.

Embodiment 55. A kit comprising the pharmaceutical composition of embodiment 54 and instructions for use.

Embodiment 56. The kit of embodiment 55, further comprising one or more additional therapeutic agents.

Embodiment 57. The kit of embodiment 56, wherein the therapeutic agent is a chemotherapeutic agent.

Embodiment 58. A method of treating a proliferative disorder in a subject comprising administering the adenovirus of any one of embodiments 1-53 or the pharmaceutical composition of embodiment 54 to the subject.

Embodiment 59. The method of embodiment 58, wherein the adenovirus or pharmaceutical composition is administered intravenously, intravascularly, intrathecally, intramuscularly, subcutaneously, intraperitoneally, or orally.

Embodiment 60. The method of embodiment 58 or 59, further comprising administering to the subject one or more additional therapeutic agents.

Embodiment 61. The method of embodiment 60, wherein the therapeutic agent is a chemotherapeutic agent.

Embodiment 62. The method of any one of embodiments 58-61, wherein the proliferative disorder is selected from the group consisting of lung cancer, prostate cancer, colorectal cancer, breast cancer, thyroid cancer, renal cancer, liver cancer and leukemia.

Embodiment 63. The method of any one of embodiments 58-62, wherein approximately 103 to 1012 plaque forming units of the adenovirus is administered to the subject.

Embodiment 64. The method of any one of embodiments 58-63, wherein the proliferative disorder is metastatic.

Embodiment 65. An adenovirus comprising E1A comprising one or more modifications and comprising E4orf6/7 comprising one or more modifications.

Embodiment 66. The adenovirus of embodiment 65, wherein the modification of E1A comprises a modification in the Rb binding site of E1A.

Embodiment 67. The adenovirus of embodiment 65, wherein the modification of E1A comprises a modification in one or more of amino acid residues 122-126 of the E1A polypeptide.

Embodiment 68. The adenovirus of embodiment 65, wherein the modification of E1A comprises a deletion.

Embodiment 69. The adenovirus of embodiment 65, wherein the deletion is a deletion of amino acid residues 122-126 of E1A.

Embodiment 70. The adenovirus of embodiment 65, wherein the modification of E1A is ΔLXCXE.

Embodiment 71. The adenovirus of any one of embodiments 65-70, wherein the modification of E4orf6/7 comprises a modification in one or both of the E4orf6/7 exons.

Embodiment 72. The adenovirus of any one of embodiments 65-70, wherein the modification of E4orf6/7 is a deletion of one or both of the E4orf6/7 exons.

Embodiment 73. The adenovirus of any one of embodiments 65-70, wherein the modification of E4orf6/7 is ΔE4orf6/7.

Embodiment 74. The adenovirus of embodiment 65, wherein the adenovirus comprises E1A ΔLXCXE and ΔE4orf6/7.

Embodiment 75. The adenovirus of any one of embodiments 65-74, wherein the adenovirus selectively replicates in Rb-deficient cells.

Embodiment 76. A pharmaceutical composition comprising the adenovirus of any one of embodiments 65-75 and a pharmaceutically acceptable carrier.

Embodiment 77. A kit comprising the pharmaceutical composition of embodiment 76 and instructions for use.

Embodiment 78. The kit of embodiment 77, further comprising one or more additional therapeutic agents.

Embodiment 79. The kit of embodiment 78, wherein the therapeutic agent is a chemotherapeutic agent.

Embodiment 80. A method of treating a proliferative disorder in a subject comprising administering the adenovirus of any one of embodiments 65-75 or the pharmaceutical composition of embodiment 76 to the subject.

Embodiment 81. The method of embodiment 80, wherein the adenovirus or pharmaceutical composition is administered intravenously, intravascularly, intrathecally, intramuscularly, subcutaneously, intraperitoneally, or orally.

Embodiment 82. The method of embodiment 80 or 81, further comprising administering to the subject one or more additional therapeutic agents.

Embodiment 83. The method of embodiment 82, wherein the therapeutic agent is a chemotherapeutic agent.

Embodiment 84. The method of any one of embodiments 65-83, wherein the proliferative disorder is selected from the group consisting of lung cancer, prostate cancer, colorectal cancer, breast cancer, thyroid cancer, renal cancer, liver cancer and leukemia.

Embodiment 85. The method of any one of embodiments 65-84, wherein approximately 103 to 1012 plaque forming units of the adenovirus is administered to the subject.

Embodiment 86. The method of any one of embodiments 65-85, wherein the proliferative disorder is metastatic.

The invention claimed is:

1. A method of inducing cytotoxicity in an Rb-deficient tumor cell in a tumor comprising contacting the tumor cell with a recombinant adenovirus by local administration of the recombinant adenovirus to the tumor, wherein the recombinant adenovirus comprises a genome comprising:

(i) an adenovirus E1A promoter operably linked to a nucleic acid sequence encoding an E1A protein comprising a modification in a first Rb-binding site; and (ii) an adenovirus E4 promoter operably linked to an E4orf6/7 gene product coding sequence comprising a deletion or modification of at least one of the two E4orf6/7 exons, wherein the deletion or the modification impairs E4orf6/7 gene product activity and/or expression, wherein the recombinant adenovirus induces cytotoxicity in the Rb-deficient tumor cell in the tumor.

2. The method of claim 1, wherein the E4orf6/7 gene product coding sequence comprises a deletion or modification of only one of the two E4orf6/7 exons.

3. The method of claim 1, wherein the E1A protein modification is selected from:

a deletion of the LXCXE motif;
a deletion of amino acid residues 122-126; a deletion of amino acid residues 2-11;
a substitution at residue Y47;
a substitution at residue C124;
and any combination of the above.

4. The method of claim 3, wherein the substitution at residue Y47 is a Y47H substitution, or the substitution at residue C124 is a C124G substitution, or both.

5. The method of claim 3, wherein the E1A protein modification comprises a deletion of the LXCXE motif.

6. The method of claim 5, wherein the adenovirus is serotype 5.

7. The method of claim 1, wherein the E1A protein further comprises a modification in a second Rb-binding site.

8. The method of claim 1, wherein the deletion or modification of at least one of the two E4orf6/7 exons comprises a deletion or modification of both of the E4orf6/7 exons.

9. The method of claim 1, wherein the genome comprises a nucleic acid encoding an E4orf6 polypeptide.

10. The method of claim 1, wherein the adenovirus is serotype 5.

* * * * *

SEQUENCE LISTING

<160> NUMBER OF SEQ ID NOS: 8

<210> SEQ ID NO 1
<211> LENGTH: 289
<212> TYPE: PRT
<213> ORGANISM: Human adenovirus type 2

```
<400> SEQUENCE: 1

Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
            20                  25                  30

Pro Pro Pro Ser His Phe Glu Pro Pro Thr Leu His Glu Leu Tyr Asp
        35                  40                  45

Leu Asp Val Thr Ala Pro Glu Asp Pro Asn Glu Glu Ala Val Ser Gln
    50                  55                  60

Ile Phe Pro Glu Ser Val Met Leu Ala Val Gln Glu Gly Ile Asp Leu
65                  70                  75                  80

Phe Thr Phe Pro Pro Ala Pro Gly Ser Pro Glu Pro Pro His Leu Ser
                85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Leu Thr Cys His Glu Ala Gly
            115                 120                 125

Phe Pro Pro Ser Asp Asp Glu Asp Glu Glu Gly Glu Glu Phe Val Leu
        130                 135                 140

Asp Tyr Val Glu His Pro Gly His Gly Cys Arg Ser Cys His Tyr His
145                 150                 155                 160

Arg Arg Asn Thr Gly Asp Pro Asp Ile Met Cys Ser Leu Cys Tyr Met
                165                 170                 175

Arg Thr Cys Gly Met Phe Val Tyr Ser Pro Val Ser Glu Pro Glu Pro
                180                 185                 190

Glu Pro Glu Pro Glu Pro Glu Pro Ala Arg Pro Thr Arg Arg Pro Lys
            195                 200                 205

Leu Val Pro Ala Ile Leu Arg Arg Pro Thr Ser Pro Val Ser Arg Glu
    210                 215                 220

Cys Asn Ser Ser Thr Asp Ser Cys Asp Ser Gly Pro Ser Asn Thr Pro
225                 230                 235                 240

Pro Glu Ile His Pro Val Val Pro Leu Cys Pro Ile Lys Pro Val Ala
                245                 250                 255

Val Arg Val Gly Gly Arg Arg Gln Ala Val Glu Cys Ile Glu Asp Leu
                260                 265                 270

Leu Asn Glu Ser Gly Gln Pro Leu Asp Leu Ser Cys Lys Arg Pro Arg
            275                 280                 285

Pro

<210> SEQ ID NO 2
<211> LENGTH: 289
<212> TYPE: PRT
<213> ORGANISM: Human adenovirus type 5

<400> SEQUENCE: 2

Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
            20                  25                  30

Pro Pro Pro Ser His Phe Glu Pro Pro Thr Leu His Glu Leu Tyr Asp
        35                  40                  45

Leu Asp Val Thr Ala Pro Glu Asp Pro Asn Glu Glu Ala Val Ser Gln
    50                  55                  60

Ile Phe Pro Asp Ser Val Met Leu Ala Val Gln Glu Gly Ile Asp Leu
```

```
65                    70                    75                    80

Leu Thr Phe Pro Pro Ala Pro Gly Ser Pro Glu Pro Pro His Leu Ser
                 85                    90                    95

Arg Gln Pro Glu Gln Pro Glu Gln Arg Ala Leu Gly Pro Val Ser Met
                100                   105                   110

Pro Asn Leu Val Pro Glu Val Ile Asp Leu Thr Cys His Glu Ala Gly
             115                   120                   125

Phe Pro Pro Ser Asp Asp Glu Asp Glu Glu Glu Glu Phe Val Leu
         130                   135                   140

Asp Tyr Val Glu His Pro Gly His Gly Cys Arg Ser Cys His Tyr His
145                   150                   155                   160

Arg Arg Asn Thr Gly Asp Pro Asp Ile Met Cys Ser Leu Cys Tyr Met
                 165                   170                   175

Arg Thr Cys Gly Met Phe Val Tyr Ser Pro Val Ser Glu Pro Glu Pro
             180                   185                   190

Glu Pro Glu Pro Glu Pro Glu Pro Ala Arg Pro Thr Arg Arg Pro Lys
             195                   200                   205

Met Ala Pro Ala Ile Leu Arg Arg Pro Thr Ser Pro Val Ser Arg Glu
         210                   215                   220

Cys Asn Ser Ser Thr Asp Ser Cys Asp Ser Gly Pro Ser Asn Thr Pro
225                   230                   235                   240

Pro Glu Ile His Pro Val Val Pro Leu Cys Pro Ile Lys Pro Val Ala
             245                   250                   255

Val Arg Val Gly Gly Arg Arg Gln Ala Val Glu Cys Ile Glu Asp Leu
             260                   265                   270

Leu Asn Glu Pro Gly Gln Pro Leu Asp Leu Ser Cys Lys Arg Pro Arg
         275                   280                   285

Pro
```

```
<210> SEQ ID NO 3
<211> LENGTH: 150
<212> TYPE: PRT
<213> ORGANISM: Human adenovirus type 2

<400> SEQUENCE: 3

Met Thr Thr Ser Gly Val Pro Phe Gly Met Thr Leu Arg Pro Thr Arg
1                    5                    10                    15

Ser Arg Leu Ser Arg Arg Thr Pro Tyr Ser Arg Asp Arg Leu Pro Pro
                 20                    25                    30

Phe Glu Thr Glu Thr Arg Ala Thr Ile Leu Glu Asp His Pro Leu Leu
             35                    40                    45

Pro Glu Cys Asn Thr Leu Thr Met His Asn Ala Trp Thr Ser Pro Ser
         50                    55                    60

Pro Pro Val Glu Gln Pro Gln Val Gly Gln Gln Pro Val Ala Gln Gln
65                    70                    75                    80

Leu Asp Ser Asp Met Asn Leu Ser Glu Leu Pro Gly Glu Phe Ile Asn
                 85                    90                    95

Ile Thr Asp Glu Arg Leu Ala Arg Gln Glu Thr Val Trp Asn Ile Thr
                100                   105                   110

Pro Lys Asn Met Ser Val Thr His Asp Met Met Leu Phe Lys Ala Ser
             115                   120                   125

Arg Gly Glu Arg Thr Val Tyr Ser Val Cys Trp Glu Gly Gly Gly Arg
         130                   135                   140

Leu Asn Thr Arg Val Leu
```

-continued

```
145                     150

<210> SEQ ID NO 4
<211> LENGTH: 150
<212> TYPE: PRT
<213> ORGANISM: Human adenovirus type 5

<400> SEQUENCE: 4

Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
                20                  25                  30

Phe Glu Thr Glu Thr Arg Ala Thr Ile Leu Glu Asp His Pro Leu Leu
                35                  40                  45

Pro Glu Cys Asn Thr Leu Thr Met His Asn Ala Trp Thr Ser Pro Ser
        50                  55                  60

Pro Pro Val Lys Gln Pro Gln Val Gly Gln Gln Pro Val Ala Gln Gln
65                  70                  75                  80

Leu Asp Ser Asp Met Asn Leu Ser Glu Leu Pro Gly Glu Phe Ile Asn
                    85                  90                  95

Ile Thr Asp Glu Arg Leu Ala Arg Gln Glu Thr Val Trp Asn Ile Thr
                100                 105                 110

Pro Lys Asn Met Ser Val Thr His Asp Met Met Leu Phe Lys Ala Ser
            115                 120                 125

Arg Gly Glu Arg Thr Val Tyr Ser Val Cys Trp Glu Gly Gly Gly Arg
        130                 135                 140

Leu Asn Thr Arg Val Leu
145                 150

<210> SEQ ID NO 5
<211> LENGTH: 128
<212> TYPE: PRT
<213> ORGANISM: Human adenovirus type 2

<400> SEQUENCE: 5

Met Ala Ala Ala Val Glu Ala Leu Tyr Val Val Leu Glu Arg Glu Gly
1               5                   10                  15

Ala Ile Leu Pro Arg Gln Glu Gly Phe Ser Gly Val Tyr Val Phe Phe
                20                  25                  30

Ser Pro Ile Asn Phe Val Ile Pro Pro Met Gly Ala Val Met Leu Ser
        35                  40                  45

Leu Arg Leu Arg Val Cys Ile Pro Pro Gly Tyr Phe Gly Arg Phe Leu
        50                  55                  60

Ala Leu Thr Asp Val Asn Gln Pro Asp Val Phe Thr Glu Ser Tyr Ile
65                  70                  75                  80

Met Thr Pro Asp Met Thr Glu Glu Leu Ser Val Val Leu Phe Asn His
                85                  90                  95

Gly Asp Gln Phe Phe Tyr Gly His Ala Gly Met Ala Val Val Arg Leu
                100                 105                 110

Met Leu Ile Arg Val Val Phe Pro Val Val Arg Gln Ala Ser Asn Val
            115                 120                 125

<210> SEQ ID NO 6
<211> LENGTH: 128
<212> TYPE: PRT
<213> ORGANISM: Human adenovirus type 5

<400> SEQUENCE: 6
```

-continued

```
Met Ala Ala Ala Val Glu Ala Leu Tyr Val Val Leu Glu Arg Glu Gly
1               5                   10                  15

Ala Ile Leu Pro Arg Gln Glu Gly Phe Ser Gly Val Tyr Val Phe Phe
                20                  25                  30

Ser Pro Ile Asn Phe Val Ile Pro Pro Met Gly Ala Val Met Leu Ser
            35                  40                  45

Leu Arg Leu Arg Val Cys Ile Pro Pro Gly Tyr Phe Gly Arg Phe Leu
        50                  55                  60

Ala Leu Thr Asp Val Asn Gln Pro Asp Val Phe Thr Glu Ser Tyr Ile
65                  70                  75                  80

Met Thr Pro Asp Met Thr Glu Glu Leu Ser Val Val Leu Phe Asn His
                85                  90                  95

Gly Asp Gln Phe Phe Tyr Gly His Ala Gly Met Ala Val Val Arg Leu
                100                 105                 110

Met Leu Ile Arg Val Val Phe Pro Val Val Arg Gln Ala Ser Asn Val
            115                 120                 125
```

<210> SEQ ID NO 7
<211> LENGTH: 35938
<212> TYPE: DNA
<213> ORGANISM: Human adenovirus type 5

<400> SEQUENCE: 7

```
catcatcaat aatatacctt attttggatt gaagccaata tgataatgag ggggtggagt        60
ttgtgacgtg gcgcggggcg tgggaacggg gcgggtgacg tagtagtgtg gcggaagtgt       120
gatgttgcaa gtgtggcgga acacatgtaa gcgacggatg tggcaaaagt gacgtttttg       180
gtgtgcgccg tgtacacag  gaagtgacaa ttttcgcgcg gttttaggcg gatgttgtag       240
taaatttggg cgtaaccgag taagatttgg ccattttcgc gggaaaactg aataagagga       300
agtgaaatct gaataatttt gtgttactca tagcgcgtaa tatttgtcta gggccgcggg       360
gactttgacc gtttacgtgg agactcgccc aggtgttttt ctcaggtgtt ttccgcgttc       420
cgggtcaaag ttggcgtttt attattatag tcagctgacg tgtagtgtat ttatacccgg       480
tgagttcctc aagaggccac tcttgagtgc cagcgagtag agttttctcc tccgagccgc       540
tccgacaccg ggactgaaaa tgagacatat tatctgccac ggaggtgtta ttaccgaaga       600
aatggccgcc agtcttttgg accagctgat cgaagaggta ctggctgata atcttccacc       660
tcctagccat tttgaaccac ctacccttca cgaactgtat gatttagacg tgacggcccc       720
cgaagatccc aacgaggagg cggtttcgca gattttttccc gactctgtaa tgttggcggt       780
gcaggaaggg attgacttac tcactttttcc gccggcgccc ggttctccgg agccgcctca       840
cctttcccgg cagcccgagc agccggagca gagagccttg ggtccggttt ctatgccaaa       900
ccttgtaccg gaggtgatcg atcttacctg ccacgaggct ggctttccac ccagtgacga       960
cgaggatgaa gagggtgagg agtttgtgtt agattatgtg gagcaccccg gcacggttg       1020 caggtcttgt cattatcacc ggaggaatac gggggaccca gatattatgt gttcgctttg      1080
ctatatgagg acctgtggca tgtttgtcta cagtaagtga aaattatggg cagtgggtga      1140
tagagtggtg ggtttggtgt ggtaattttt tttttaattt ttacagtttt gtggtttaaa      1200
gaattttgta ttgtgatttt tttaaaaggt cctgtgtctg aacctgagcc tgagcccgag      1260
ccagaaccgg agcctgcaag acctacccgc cgtcctaaaa tggcgcctgc tatcctgaga      1320
cgcccgacat cacctgtgtc tagagaatgc aatagtagta cggatagctg tgactccggt      1380
```

-continued

```
ccttctaaca cacctcctga gatacacccg gtggtcccgc tgtgccccat taaaccagtt   1440
gccgtgagag ttggtggggcg tcgccaggct gtggaatgta tcgaggactt gcttaacgag   1500
cctgggcaac ctttggactt gagctgtaaa cgccccaggc cataaggtgt aaacctgtga   1560
ttgcgtgtgt ggttaacgcc tttgtttgct gaatgagttg atgtaagttt aataaagggt   1620
gagataatgt ttaacttgca tggcgtgtta aatggggcgg ggcttaaagg gtatataatg   1680
cgccgtgggc taatcttggt tacatctgac ctcatggagg cttgggagtg tttggaagat   1740
ttttctgctg tgcgtaactt gctggaacag agctctaaca gtacctcttg gttttggagg   1800
tttctgtggg gctcatccca ggcaaagtta gtctgcagaa ttaaggagga ttacaagtgg   1860
gaatttgaag agctttttgaa atcctgtggt gagctgtttg attcttttgaa tctgggtcac   1920 caggcgcttt tccaagagaa ggtcatcaag actttggatt tttccacacc ggggcgcgct   1980
gcggctgctg ttgctttttt gagttttata aaggataaat ggagcgaaga aacccatctg   2040 agcgggggt acctgctgga tttttctggcc atgcatctgt ggagagcggt tgtgagacac   2100
aagaatcgcc tgctactgtt gtcttccgtc cgcccggcga taataccgac ggaggagcag   2160
cagcagcagc aggaggaagc caggcggcgg cggcaggagc agagcccatg gaacccgaga   2220
gccggcctgg accctcggga atgaatgttg tacaggtggc tgaactgtat ccagaactga   2280
gacgcatttt gacaattaca gaggatgggc aggggctaaa gggggtaaag agggagcggg   2340
gggcttgtga ggctacagag gaggctagga atctagcttt tagcttaatg accagacacc   2400
gtcctgagtg tattactttt caacagatca aggataattg cgctaatgag cttgatctgc   2460
tggcgcagaa gtattccata gagcagctga ccacttactg gctgcagcca ggggatgatt   2520
ttgaggaggc tattagggta tatgcaaagg tggcacttag gccagattgc aagtacaaga   2580
tcagcaaact tgtaaatatc aggaattgtt gctacatttc tgggaacggg gccgaggtgg   2640
agatagatac ggaggatagg gtggccttta gatgtagcat gataaatatg tggccggggg   2700
tgcttggcat ggacggggtg gttattatga atgtaaggtt tactggcccc aattttagcg   2760
gtacggtttt cctggccaat accaacctta tcctacacgg tgtaagcttc tatgggttta   2820
acaatacctg tgtggaagcc tggaccgatg taagggttcg gggctgtgcc ttttactgct   2880
gctggaaggg ggtggtgtgt cgccccaaaa gcagggcttc aattaagaaa tgcctctttg   2940
aaaggtgtac cttgggtatc ctgtctgagg gtaactccag ggtgcgccac aatgtggcct   3000
ccgactgtgg ttgcttcatg ctagtgaaaa gcgtggctgt gattaagcat aacatggtat   3060
gtggcaactg cgaggacagg gcctctcaga tgctgacctg ctcggacggc aactgtcacc   3120
tgctgaagac cattcacgta gccagccact ctcgcaaggc ctggccagtg tttgagcata   3180
acatactgac ccgctgttcc ttgcatttgg gtaacaggag gggggtgttc ctaccttacc   3240
aatgcaattt gagtcacact aagatattgc ttgagcccga gagcatgtcc aaggtgaacc   3300
tgaacggggt gtttgacatg accatgaaga tctggaaggt gctgaggtac gatgagaccc   3360
gcaccaggtg cagaccctgc gagtgtggcg gtaaacatat taggaaccag cctgtgatgc   3420
tggatgtgac cgaggagctg aggcccgatc acttggtgct ggcctgcacc cgcgctgagt   3480
ttggctctag cgatgaagat acagattgag gtactgaaat gtgtgggcgt ggcttaaggg   3540
tgggaaagaa tatataaggt gggggtctta tgtagttttg tatctgtttt gcagcagccg   3600
ccgccgccat gagcaccaac tcgtttgatg gaagcattgt gagctcatat ttgacaacgc   3660
gcatgccccc atgggccggg gtgcgtcaga atgtgatggg ctccagcatt gatggtcgcc   3720
ccgtcctgcc cgcaaactct actaccttga cctacgagac cgtgtctgga acgccgttgg   3780
```

```
agactgcagc ctccgccgcc gcttcagccg ctgcagccac cgcccgcggg attgtgactg    3840
actttgcttt cctgagcccg cttgcaagca gtgcagcttc ccgttcatcc gcccgcgatg    3900
acaagttgac ggctcttttg gcacaattgg attctttgac ccgggaactt aatgtcgttt    3960
ctcagcagct gttggatctg cgccagcagg tttctgccct gaaggcttcc tcccctccca    4020
atgcggttta aaacataaat aaaaaaccag actctgtttg gatttggatc aagcaagtgt    4080
cttgctgtct ttatttaggg gttttgcgcg cgcggtaggc ccgggaccag cggtctcggt    4140
cgttgagggt cctgtgtatt ttttccagga cgtggtaaag gtgactctgg atgttcagat    4200
acatgggcat aagcccgtct ctggggtgga ggtagcacca ctgcagagct tcatgctgcg    4260
gggtggtgtt gtagatgatc cagtcgtagc aggagcgctg ggcgtggtgc ctaaaaatgt    4320 cttttcagtag caagctgatt gccaggggca ggcccttggt gtaagtgttt acaaagcggt    4380
taagctggga tgggtgcata cgtggggata tgagatgcat cttggactgt attttttaggt    4440 tggctatgtt cccagccata tccctccggg gattcatgtt gtgcagaacc accagcacag    4500
tgtatccggt gcacttggga aatttgtcat gtagcttaga aggaaatgcg tggaagaact    4560
tggagacgcc cttgtgacct ccaagatttt ccatgcattc gtccataatg atggcaatgg    4620
gcccacgggc ggcggcctgg gcgaagatat ttctgggatc actaacgtca tagttgtgtt    4680
ccaggatgag atcgtcatag gccattttta caaagcgcgg gcggagggtg ccagactgcg    4740
gtataatggt tccatccggc ccaggggcgt agttaccctc acagatttgc atttcccacg    4800
ctttgagttc agatgggggg atcatgtcta cctgcggggc gatgaagaaa acggtttccg    4860 gggtaggga gatcagctgg gaagaaagca ggttcctgag cagctgcgac ttaccgcagc    4920
cggtgggccc gtaaatcaca cctattaccg ggtgcaactg gtagttaaga gagctgcagc    4980
tgccgtcatc cctgagcagg ggggccactt cgttaagcat gtccctgact cgcatgtttt    5040
ccctgaccaa atccgccaga aggcgctcgc cgcccagcga tagcagttct tgcaaggaag    5100
caaagttttt caacggtttg agaccgtccg ccgtaggcat gcttttgagc gtttgaccaa    5160
gcagttccag gcggtcccac agctcggtca cctgctctac ggcatctcga tccagcatat    5220
ctcctcgttt cgcgggttgg ggcggctttc gctgtacggc agtagtcggt gctcgtccag    5280
acgggccagg gtcatgtctt tccacgggcg cagggtcctc gtcagcgtag tctgggtcac    5340
ggtgaagggg tgcgctccgg gctgcgcgct ggccagggtg cgcttgaggc tggtcctgct    5400
ggtgctgaag cgctgccggt cttcgccctg cgcgtcggcc aggtagcatt tgaccatggt    5460
gtcatagtcc agcccctccg cggcgtggcc cttggcgcgc agcttgccct tggaggaggc    5520
gccgcacgag gggcagtgca gacttttgag ggcgtagagc ttgggcgcga gaaataccga    5580
ttccggggag taggcatccg cgccgcaggc cccgcagacg gtctcgcatt ccacgagcca    5640
ggtgagctct ggccgttcgg ggtcaaaaac caggtttccc ccatgctttt tgatgcgttt    5700
cttacctctg gtttccatga gccggtgtcc acgctcggtg acgaaaaggc tgtccgtgtc    5760
cccgtataca gacttgagag gcctgtcctc gagcggtgtt ccgcggtcct cctcgtatag    5820
aaactcggac cactctgaga caaaggctcg cgtccaggcc agcacgaagg aggctaagtg    5880
ggaggggtag cggtcgttgt ccactagggg gtccactcgc tccagggtgt gaagacacat    5940
gtcgccctct tcggcatcaa ggaaggtgat tggtttgtag gtgtaggcca cgtgaccggg    6000
tgttcctgaa gggggctat aaaaggggg ggggcgcgt cgtcctcac tctcttccgc        6060 atcgctgtct gcgagggcca gctgttgggg tgagtactcc ctctgaaaag cgggcatgac    6120
```

-continued

```
ttctgcgcta agattgtcag tttccaaaaa cgaggaggat ttgatattca cctggcccgc      6180
ggtgatgcct ttgagggtgg ccgcatccat ctggtcagaa aagacaatct ttttgttgtc      6240
aagcttggtg gcaaacgacc cgtagagggc gttggacagc aacttggcga tggagcgcag      6300
ggtttggttt ttgtcgcgat cggcgcgctc cttggccgcg atgtttagct gcacgtattc      6360
gcgcgcaacg caccgccatt cgggaaagac ggtggtgcgc tcgtcgggca ccaggtgcac      6420
gcgccaaccg cggttgtgca gggtgacaag gtcaacgctg gtggctacct ctccgcgtag      6480
gcgctcgttg gtccagcaga ggcggccgcc cttgcgcgag cagaatggcg gtagggggtc      6540
tagctgcgtc tcgtccgggg ggtctgcgtc cacggtaaag accccgggca gcaggcgcgc      6600
gtcgaagtag tctatcttgc atccttgcaa gtctagcgcc tgctgccatg cgcgggcggc      6660
aagcgcgcgc tcgtatgggt tgagtggggg accccatggc atgggtgggg tgagcgcgga      6720
ggcgtacatg ccgcaaatgt cgtaaacgta gaggggctct ctgagtattc caagatatgt      6780
agggtagcat cttccaccgc ggatgctggc gcgcacgtaa tcgtatagtt cgtgcgaggg      6840
agcgaggagg tcgggaccga ggttgctacg ggcgggctgc tctgctcgga agactatctg      6900
cctgaagatg gcatgtgagt tggatgatat ggttggacgc tggaagacgt tgaagctggc      6960
gtctgtgaga cctaccgcgt cacgcacgaa ggaggcgtag gagtcgcgca gcttgttgac      7020
cagctcggcg gtgacctgca cgtctagggc gcagtagtcc agggtttcct tgatgatgtc      7080
atacttatcc tgtccctttt ttttccacag ctcgcggttg aggacaaact cttcgcggtc      7140
tttccagtac tcttggatcg gaaacccgtc ggcctccgaa cggtaagagc ctagcatgta      7200
gaactggttg acggcctggt aggcgcagca tcccttttct acgggtagcg cgtatgcctg      7260
cgcggccttc cggagcgagg tgtgggtgag cgcaaaggtg tccctgacca tgactttgag      7320
gtactggtat ttgaagtcag tgtcgtcgca tccgccctgc tcccagagca aaaagtccgt      7380
gcgctttttg gaacgcggat ttggcagggc gaaggtgaca tcgttgaaga gtatctttcc      7440
cgcgcgaggc ataaagttgc gtgtgatgcg gaagggtccc ggcacctcgg aacggttgtt      7500
aattacctgg gcggcgagca cgatctcgtc aaagccgttg atgttgtggc ccacaatgta      7560
aagttccaag aagcgcggga tgcccttgat ggaaggcaat tttttaagtt cctcgtaggt      7620
gagctcttca ggggagctga gcccgtgctc tgaaagggcc cagtctgcaa gatgagggtt      7680
ggaagcgacg aatgagctcc acaggtcacg ggccattagc atttgcaggt ggtcgcgaaa      7740
ggtcctaaac tggcgaccta tggccatttt ttctggggtg atgcagtaga aggtaagcgg      7800
gtcttgttcc cagcggtccc atccaaggtt cgcggctagg tctcgcgcgg cagtcactag      7860
aggctcatct ccgccgaact tcatgaccag catgaagggc acgagctgct tcccaaaggc      7920
ccccatccaa gtataggtct ctacatcgta ggtgacaaag agacgctcgg tgcgaggatg      7980
cgagccgatc gggaagaact ggatctcccg ccaccaattg gaggagtggc tattgatgtg      8040
gtgaaagtag aagtccctgc gacgggccga acactcgtgc tggcttttgt aaaaacgtgc      8100
gcagtactgg cagcggtgca cgggctgtac atcctgcacg aggttgacct gacgaccgcg      8160
cacaaggaag cagagtggga atttgagccc ctcgcctggc gggtttggct ggtggtcttc      8220
tacttcggct gcttgtcctt gaccgtctgg ctgctcgagg ggagttacgg tggatcggac      8280
caccacgccg cgcgagccca aagtccagat gtccgcgcgc ggcggtcgga gcttgatgac      8340
aacatcgcgc agatgggagc tgtccatggt ctggagctcc gcggcgtca ggtcaggcgg      8400 gagctcctgc aggtttacct cgcatagacg ggtcagggcg cgggctagat ccaggtgata      8460
cctaatttcc aggggctggt tggtggcggc gtcgatggct tgcaagaggc cgcatccccg      8520
```

```
cggcgcgact acggtaccgc gcggcgggcg gtgggccgcg ggggtgtcct tggatgatgc   8580
atctaaaagc ggtgacgcgg gcgagccccc ggaggtaggg ggggctccgg acccgccggg   8640 agaggggca ggggcacgtc ggcgccgcgc gcgggcagga gctggtgctg cgcgcgtagg    8700
ttgctggcga acgcgacgac gcggcggttg atctcctgaa tctggcgcct ctgcgtgaag   8760
acgacgggcc cggtgagctt gagcctgaaa gagagttcga cagaatcaat ttcggtgtcg   8820
ttgacggcgg cctggcgcaa aatctcctgc acgtctcctg agttgtcttg ataggcgatc    8880
tcggccatga actgctcgat ctcttcctcc tggagatctc cgcgtccggc tcgctccacg    8940
gtggcggcga ggtcgttgga aatgcgggcc atgagctgcg agaaggcgtt gaggcctccc     9000
tcgttccaga cgcggctgta gaccacgccc ccttcggcat cgcgggcgcg catgaccacc     9060
tgcgcgagat tgagctccac gtgccgggcg aagacgcgct agtttcgcag gcgctgaaag     9120
aggtagttga gggtggtggc ggtgtgttct gccacgaaga agtacataac ccagcgtcgc     9180
aacgtggatt cgttgatatc ccccaaggcc tcaaggcgct ccatggcctc gtagaagtcc      9240
acggcgaagt tgaaaaactg ggagttgcgc gccgacacgg ttaactcctc ctccagaaga      9300
cggatgagct cggcgacagt gtcgcgcacc tcgcgctcaa aggctacagg ggcctcttct       9360
tcttcttcaa tctcctcttc cataagggcc tccccttctt cttcttctgg cggcggtggg       9420
ggagggggga cacggcggcg acgacggcgc accgggaggc ggtcgacaaa gcgctcgatc       9480
atctccccgc ggcgacggcg catggtctcg gtgacggcgc ggccgttctc gcggggggcgc      9540 agttggaaga cgccgcccgt catgtcccgg ttatgggttg gcgggggggct gccatgcggc      9600 agggatacgg cgctaacgat gcatctcaac aattgttgtg taggtactcc gccgccgagg       9660
gacctgagcg agtccgcatc gaccggatcg gaaaacctct cgagaaaggc gtctaaccag       9720
tcacagtcgc aaggtaggct gagcaccgtg gcgggcggca gcgggcggcg gtcggggttg       9780
tttctggcgg aggtgctgct gatgatgtaa ttaaagtagg cggtcttgag acggcggatg       9840
gtcgacagaa gcaccatgtc cttgggtccg gcctgctgaa tgcgcaggcg gtcggccatg        9900
ccccaggctt cgttttgaca tcggcgcagg tctttgtagt agtcttgcat gagcctttct        9960
accggcactt cttcttctcc ttcctcttgt cctgcatctc ttgcatctat cgctgcggcg       10020
gcggcggagt ttggccgtag gtggcgccct cttcctccca tgcgtgtgac cccgaagccc       10080
ctcatcggct gaagcagggc taggtcggcg acaacgcgct cggctaatat ggcctgctgc       10140
acctgcgtga gggtagactg gaagtcatcc atgtccacaa agcggtggta tgcgcccgtg       10200
ttgatggtgt aagtgcagtt ggccataacg gaccagttaa cggtctggtg acccggctgc       10260
gagagctcgg tgtacctgag acgcgagtaa gccctcgagt caaatacgta gtcgttgcaa       10320
gtccgcacca ggtactggta tcccaccaaa aagtgcggcg gcggctggcg gtagaggggc       10380
cagcgtaggg tggccggggc tccgggggcg agatcttcca acataaggcg atgatatccg       10440
tagatgtacc tggacatcca ggtgatgccg gcggcggtgg tggaggcgcg cggaaagtcg       10500
cggacgcggt tccagatgtt gcgcagcggc aaaaagtgct ccatggtcgg gacgctctgg       10560
ccggtcaggc gcgcgcaatc gttgacgctc tagaccgtgc aaaaggagag cctgtaagcg       10620
ggcactcttc cgtggtctgg tggataaatt cgcaagggta tcatggcgga cgaccggggt       10680
tcgagccccg tatccggccg tccgccgtga tccatgcggt taccgcccgc gtgtcgaacc       10740
caggtgtgcg acgtcagaca acgggggagt gctccttttg gcttccttcc aggcgcggcg       10800
gctgctgcgc tagctttttt ggccactggc cgcgcgcagc gtaagcggtt aggctggaaa       10860
```

-continued

```
gcgaaagcat taagtggctc gctccctgta gccggagggt tattttccaa gggttgagtc   10920
gcgggacccc cggttcgagt ctcggaccgg ccggactgcg cgaacgggg gtttgcctcc   10980 ccgtcatgca agacccgct tgcaaattcc tccggaaaca gggacgagcc cctttttgc   11040 ttttcccaga tgcatccggt gctgcggcag atgcgcccc ctcctcagca gcggcaagag   11100
caagagcagc ggcagacatg cagggcaccc tccctcctc ctaccgcgtc aggaggggcg   11160
acatccgcgg ttgacgcggc agcagatggt gattacgaac ccccgcggcg ccgggcccgg   11220
cactacctgg acttggagga gggcgagggc ctggcgcggc taggagcgcc ctctcctgag   11280
cggtacccaa gggtgcagct gaagcgtgat acgcgtgagg cgtacgtgcc gcggcagaac   11340
ctgtttcgcg accgcgaggg agaggagccc gaggagatgc gggatcgaaa gttccacgca   11400
gggcgcgagc tgcggcatgg cctgaatcgc gagcggttgc tgcgcgagga ggactttgag   11460
cccgacgcgc gaaccgggat tagtcccgcg cgcgcacacg tggcggccgc cgacctggta   11520
accgcatacg agcagacggt gaaccaggag attaactttc aaaaaagctt taacaaccac   11580
gtgcgtacgc ttgtggcgcg cgaggaggtg gctataggac tgatgcatct gtgggacttt   11640
gtaagcgcgc tggagcaaaa cccaaatagc aagccgctca tggcgcagct gttccttata   11700
gtgcagcaca gcagggacaa cgaggcattc agggatgcgc tgctaaacat agtagagccc   11760
gagggccgct ggctgctcga tttgataaac atcctgcaga gcatagtggt gcaggagcgc   11820
agcttgagcc tggctgacaa ggtggccgcc atcaactatt ccatgcttag cctgggcaag   11880
ttttacgccc gcaagatata ccataccccct tacgttccca tagacaagga ggtaaagatc   11940 gagggggttct acatgcgcat ggcgctgaag gtgcttacct tgagcgacga cctgggcgtt   12000
tatcgcaacg agcgcatcca caaggccgtg agcgtgagcc ggcggcgcga gctcagcgac   12060
cgcgagctga tgcacagcct gcaaagggcc ctggctggca cgggcagcgg cgatagagag   12120
gccgagtcct actttgacgc gggcgctgac ctgcgctggg ccccaagccg acgcgccctg   12180
gaggcagctg gggccggacc tgggctggcg gtggcacccg cgcgcgctgg caacgtcggc   12240
ggcgtggagg aatatgacga ggacgatgag tacgagccag aggacggcga gtactaagcg   12300
gtgatgtttc tgatcagatg atgcaagacg caacggaccc ggcggtgcgg cggcgctgc   12360 agagccagcc gtccggcctt aactccacgg acgactggcg ccaggtcatg gaccgcatca   12420
tgtcgctgac tgcgcgcaat cctgacgcgt tccggcagca gccgcaggcc aaccggctct   12480
ccgcaattct ggaagcggtg gtcccggcgc gcgcaaaccc cacgcacgag aaggtgctgg   12540
cgatcgtaaa cgcgctggcc gaaaacaggg ccatccggcc cgacgaggcc ggcctggtct   12600
acgacgcgct gcttcagcgc gtggctcgtt acaacagcgg caacgtgcag accaacctgg   12660
accggctggt ggggggatgtg cgcgaggccg tggcgcagcg tgagcgcgcg cagcagcagg   12720
gcaacctggg ctccatggtt gcactaaacg ccttcctgag tacacagccc gccaacgtgc   12780
cgcggggaca ggaggactac accaactttg tgagcgcact gcggctaatg gtgactgaga   12840
caccgcaaag tgaggtgtac cagtctgggc cagactattt tttccagacc agtagacaag   12900
gcctgcagac cgtaaacctg agccaggctt tcaaaaactt gcaggggctg tggggggtgc   12960
gggctcccac aggcgaccgc gcgaccgtgt ctagcttgct gacgcccaac tcgcgcctgt   13020
tgctgctgct aatagcgccc ttcacggaca gtggcagcgt gtcccgggac acatacctag   13080
gtcacttgct gacactgtac cgcgaggcca taggtcaggc gcatgtggac gagcatactt   13140
tccaggagat tacaagtgtc agccgcgcgc tggggcagga ggacacgggc agcctggagg   13200
caaccctaaa ctacctgctg accaaccggc ggcagaagat cccctcgttg cacagtttaa   13260
```

-continued

```
acagcgagga ggagcgcatt ttgcgctacg tgcagcagag cgtgagcctt aacctgatgc  13320
gcgacggggt aacgcccagc gtggcgctgg acatgaccgc gcgcaacatg gaaccgggca  13380
tgtatgcctc aaaccggccg tttatcaacc gcctaatgga ctacttgcat cgcgcggccg  13440
ccgtgaaccc cgagtatttc accaatgcca tcttgaaccc gcactggcta ccgcccctg   13500 gtttctacac cgggggattc gaggtgcccg agggtaacga tggattcctc tgggacgaca  13560
tagacgacag cgtgttttcc ccgcaaccgc agacctgct  agagttgcaa cagcgcgagc  13620
aggcagaggc ggcgctgcga aaggaaagct tccgcaggcc aagcagcttg tccgatctag  13680
gcgctgcggc cccgcggtca gatgctagta gcccattcc  aagcttgata gggtctctta  13740
ccagcactcg caccacccgc ccgcgcctgc tgggcgagga ggagtaccta aacaactcgc  13800
tgctgcagcc gcagcgcgaa aaaaacctgc ctccggcatt tcccaacaac gggatagaga  13860
gcctagtgga caagatgagt agatggaaga cgtacgcgca ggagcacagg gacgtgccag  13920
gcccgcgccc gcccacccgt cgtcaaaggc acgaccgtca gcgggtctg  gtgtgggagg  13980 acgatgactc ggcagacgac agcagcgtcc tggatttggg agggagtggc aacccgtttg  14040
cgcaccttcg ccccaggctg gggagaatgt tttaaaaaaa aaaaagcatg atgcaaaata  14100
aaaaactcac caaggccatg gcaccgagcg ttggtttct  tgtattcccc ttagtatgcg  14160
gcgcgcggcg atgtatgagg aaggtcctcc tccctcctac gagagtgtgg tgagcgcggc  14220
gccagtggcg gcggcgctgg gttctccctt cgatgctccc ctggaccccgc cgtttgtgcc  14280 tccgcggtac ctgcggccta ccggggggag aaacagcatc cgttactctg agttggcacc  14340
cctattcgac accacccgtg tgtacctggt ggacaacaag tcaacggatg tggcatccct  14400
gaactaccag aacgaccaca gcaactttct gaccacggtc attcaaaaca atgactacag  14460
cccgggggag gcaagcacac agaccatcaa tcttgacgac cggtcgcact ggggcggcga  14520
cctgaaaacc atcctgcata ccaacatgcc aaatgtgaac gagttcatgt ttaccaataa  14580
gtttaaggcg cgggtgatgg tgtcgcgctt gcctactaag gacaatcagg tggagctgaa  14640
atacgagtgg gtggagttca cgctgcccga gggcaactac tccgagacca tgaccataga  14700
ccttatgaac aacgcgatcg tggagcacta cttgaaagtg ggcagacaga acgggggttct  14760 ggaaagcgac atcggggtaa agtttgacac ccgcaacttc agactgggggt ttgaccccgt  14820 cactggtctt gtcatgcctg gggtatatac aaacgaagcc ttccatccag acatcatttt  14880
gctgccagga tgcgggggtgg acttcaccca cagccgcctg agcaacttgt tgggcatccg  14940
caagcggcaa cccttccagg agggcttttag gatcacctac gatgatctgg agggtggtaa  15000
cattcccgca ctgttggatg tggacgccta ccaggcgagc ttgaaagatg acaccgaaca  15060
gggcgggggt ggcgcaggcg gcagcaacag cagtggcagc ggcgcggaag agaactccaa  15120
cgcggcagcc gcggcaatgc agccggtgga ggacatgaac gatcatgcca ttcgcggcga  15180 caccttttgcc acacgggctg aggagaagcg cgctgaggcc gaagcagcgg ccgaagctgc  15240
cgcccccgct gcgcaacccg aggtcgagaa gcctcagaag aaaccggtga tcaaacccct  15300
gacagaggac agcaagaaac gcagttacaa cctaataagc aatgacagca ccttcaccca  15360
gtaccgcagc tggtaccttg catacaacta cggcgaccct cagaccggaa tccgctcatg  15420 gacccctgctt tgcactcctg acgtaacctg cggctcggag caggtctact ggtcgttgcc  15480
agacatgatg caagaccccg tgaccttccg ctccacgcgc cagatcagca cttttccggt  15540
ggtgggcgcc gagctgttgc ccgtgcactc caagagcttc tacaacgacc aggccgtcta  15600
```

-continued

```
ctcccaactc atccgccagt ttacctctct gacccacgtg ttcaatcgct ttcccgagaa   15660
ccagattttg gcgcgcccgc cagcccccac catcaccacc gtcagtgaaa acgttcctgc   15720
tctcacagat cacgggacgc taccgctgcg caacagcatc ggaggagtcc agcgagtgac   15780
cattactgac gccagacgcc gcacctgccc ctacgtttac aaggccctgg gcatagtctc   15840
gccgcgcgtc ctatcgagcc gcactttttg agcaagcatg tccatcctta tatcgcccag   15900
caataacaca ggctggggcc tgcgcttccc aagcaagatg tttggcgggg ccaagaagcg   15960
ctccgaccaa cacccagtgc gcgtgcgcgg gcactaccgc gcgccctggg gcgcgcacaa   16020
acgcggccgc actgggcgca ccaccgtcga tgacgccatc gacgcggtgg tggaggaggc   16080
gcgcaactac acgcccacgc cgccaccagt gtccacagtg gacgcggcca ttcagaccgt   16140
ggtgcgcgga gcccggcgct atgctaaaat gaagagacgg cggaggcgcg tagcacgtcg   16200
ccaccgccgc cgacccggca ctgccgccca acgcgcggcg gcggccctgc ttaaccgcgc   16260
acgtcgcacc ggccgacggg cggccatgcg ggccgctcga aggctggccg cgggtattgt   16320
cactgtgccc cccaggtcca ggcgacgagc ggccgccgca gcagccgcgg ccattagtgc   16380
tatgactcag ggtcgcaggg gcaacgtgta ttgggtgcgc gactcggtta gcggcctgcg   16440
cgtgcccgtg cgcacccgcc ccccgcgcaa ctagattgca agaaaaaact acttagactc   16500
gtactgttgt atgtatccag cggcggcggc gcgcaacgaa gctatgtcca agcgcaaaat   16560
caaagaagag atgctccagg tcatcgcgcc ggagatctat ggccccccga agaaggaaga   16620
gcaggattac aagccccgaa agctaaagcg ggtcaaaaag aaaaagaaag atgatgatga   16680
tgaacttgac gacgaggtgg aactgctgca cgctaccgcg cccaggcgac gggtacagtg   16740
gaaaggtcga cgcgtaaaac gtgttttgcg acccggcacc accgtagtct ttacgcccgg   16800
tgagcgctcc acccgcacct acaagcgcgt gtatgatgag gtgtacggcg acgaggacct   16860
gcttgagcag gccaacgagc gcctcgggga gtttgcctac ggaaagcggc ataaggacat   16920
gctggcgttg ccgctggacg agggcaaccc aacacctagc ctaaagcccg taacactgca   16980
gcaggtgctg cccgcgcttg caccgtccga agaaaagcgc ggcctaaagc gcgagtctgg   17040
tgacttggca cccaccgtgc agctgatggt acccaagcgc cagcgactgg aagatgtctt   17100
ggaaaaaatg accgtggaac ctgggctgga gcccgaggtc cgcgtgcggc caatcaagca   17160
ggtggcgccg ggactgggcg tgcagaccgt ggacgttcag atacccacta ccagtagcac   17220
cagtattgcc accgccacag agggcatgga gacacaaacg tccccggttg cctcagcggt   17280
ggcggatgcc gcggtgcagg cggtcgctgc ggccgcgtcc aagacctcta cggaggtgca   17340
aacggacccg tggatgtttc gcgtttcagc cccccggcgc ccgcgcggtt cgaggaagta   17400
cggcgccgcc agcgcgctac tgcccgaata tgccctacat ccttccattg cgcctacccc   17460
cggctatcgt ggctacacct accgccccag aagacgagca actacccgac gccgaaccac   17520
cactggaacc cgccgccgcc gtcgccgtcg ccagcccgtg ctggcccga tttccgtgcg    17580 cagggtggct cgcgaaggag gcaggaccct ggtgctgcca acagcgcgct accaccccag   17640
catcgtttaa aagccggtct ttgtggttct tgcagatatg gccctcacct gccgcctccg   17700
tttcccggtg ccgggattcc gaggaagaat gcaccgtagg aggggcatgg ccggccacgg   17760
cctgacgggc ggcatgcgtc gtgcgcacca ccggcggcgg cgcgcgtcgc accgtcgcat   17820
gcgcggcggt atcctgcccc tccttattcc actgatcgcc gcggcgattg cgccgtgcc    17880 cggaattgca tccgtggcct tgcaggcgca gagacactga ttaaaaacaa gttgcatgtg   17940
gaaaaatcaa aataaaaagt ctggactctc acgctcgctt ggtcctgtaa ctattttgta   18000
```

-continued

```
gaatggaaga catcaacttt gcgtctctgg ccccgcgaca cggctcgcgc ccgttcatgg   18060
gaaactggca agatatcggc accagcaata tgagcggtgg cgccttcagc tggggctcgc   18120
tgtggagcgg cattaaaaat ttcggttcca ccgttaagaa ctatggcagc aaggcctgga   18180
acagcagcac aggccagatg ctgagggata agttgaaaga gcaaaatttc caacaaaagg   18240
tggtagatgg cctggcctct ggcattagcg gggtggtgga cctggccaac caggcagtgc   18300
aaaataagat taacagtaag cttgatcccc gccctcccgt agaggagcct ccaccggccg   18360
tggagacagt gtctccagag gggcgtggcg aaaagcgtcc gcgccccgac agggaagaaa   18420
ctctggtgac gcaaatagac gagcctccct cgtacgagga ggcactaaag caaggcctgc   18480
ccaccacccg tcccatcgcg cccatggcta ccggagtgct gggccagcac acacccgtaa   18540
cgctggacct gcctcccccc gccgacaccc agcagaaacc tgtgctgcca ggcccgaccg   18600
ccgttgttgt aacccgtcct agccgcgcgt ccctgcgccg cgccgccagc ggtccgcgat   18660
cgttgcggcc cgtagccagt ggcaactggc aaagcacact gaacagcatc gtgggtctgg   18720
gggtgcaatc cctgaagcgc cgacgatgct tctgaatagc taacgtgtcg tatgtgtgtc   18780
atgtatgcgt ccatgtcgcc gccagaggag ctgctgagcc gccgcgcgcc cgctttccaa   18840
gatggctacc ccttcgatga tgccgcagtg gtcttacatg cacatctcgg gccaggacgc   18900
ctcggagtac ctgagccccg ggctggtgca gtttgcccgc gccaccgaga cgtacttcag   18960
cctgaataac aagtttagaa accccacggt ggcgcctacg cacgacgtga ccacagaccg   19020 gtccagcgt ttgacgctgc ggttcatccc tgtggaccgt gaggatactg cgtactcgta   19080
caaggcgcgg ttcacccctag ctgtgggtga taaccgtgtg ctggacatgg cttccacgta   19140
ctttgacatc cgcggcgtgc tggacagggg ccctactttt aagccctact ctggcactgc   19200
ctacaacgcc ctggctccca agggtgcccc aaatccttgc gaatgggatg aagctgctac   19260
tgctcttgaa ataaacctag aagaagagga cgatgacaac gaagacgaag tagacgagca   19320
agctgagcag caaaaaactc acgtatttgg gcaggcgcct tattctggta taaatattac   19380
aaaggagggt attcaaatag gtgtcgaagg tcaaacacct aaatatgccg ataaaacatt   19440
tcaacctgaa cctcaaatag gagaatctca gtggtacgaa actgaaatta atcatgcagc   19500
tgggagagtc cttaaaaaga ctaccccaat gaaaccatgt tacggttcat atgcaaaacc   19560
cacaaatgaa aatggagggc aaggcattct tgtaaagcaa caaaatggaa agctagaaag   19620
tcaagtggaa atgcaatttt tctcaactac tgaggcgacc gcaggcaatg gtgataactt   19680
gactcctaaa gtggtattgt acagtgaaga tgtagatata gaaaccccag acactcatat   19740
ttcttacatg cccactatta aggaaggtaa ctcacgagaa ctaatgggcc aacaatctat   19800
gcccaacagg cctaattaca ttgctttttag ggacaatttt attggtctaa tgtattacaa   19860
cagcacgggt aatatgggtg ttctggcggg ccaagcatcg cagttgaatg ctgttgtaga   19920
tttgcaagac agaaacacag agctttcata ccagcttttg cttgattcca ttggtgatag   19980
aaccaggtac ttttctatgt ggaatcaggc tgttgacagc tatgatccag atgttagaat   20040
tattgaaaat catggaactg aagatgaact tccaaattac tgctttccac tgggaggtgt   20100
gattaataca gagactctta ccaaggtaaa acctaaaaca ggtcaggaaa atggatggga   20160
aaaagatgct acagaatttt cagataaaaa tgaaataaga gttggaaata ttttgccat   20220 ggaaatcaat ctaaatgcca acctgtggag aaatttcctg tactccaaca tagcgctgta   20280
tttgcccgac aagctaaagt acagtccttc caacgtaaaa atttctgata acccaaacac   20340
```

-continued

```
ctacgactac atgaacaagc gagtggtggc tcccgggtta gtggactgct acattaacct   20400
tggagcacgc tggtcccttg actatatgga caacgtcaac ccatttaacc accaccgcaa   20460
tgctggcctg cgctaccgct caatgttgct gggcaatggt cgctatgtgc ccttccacat   20520
ccaggtgcct cagaagttct ttgccattaa aaacctcctt ctcctgccgg gctcatacac   20580
ctacgagtgg aacttcagga aggatgttaa catggttctg cagagctccc taggaaatga   20640
cctaaggggt gacggagcca gcattaagtt tgatagcatt tgcctttacg ccaccttctt   20700
ccccatggcc cacaacaccg cctccacgct tgaggccatg cttagaaacg acaccaacga   20760
ccagtccttt aacgactatc tctccgccgc caacatgctc taccctatac ccgccaacgc   20820
taccaacgtg cccatatcca tcccctcccg caactgggcg gctttccgcg gctgggcctt   20880
cacgcgcctt aagactaagg aaaccccatc actgggctcg ggctacgacc cttattacac   20940
ctactctggc tctataccct acctagatgg aaccttttac ctcaaccaca cctttaagaa   21000
ggtggccatt acctttgact cttctgtcag ctggcctggc aatgaccgcc tgcttacccc   21060
caacgagttt gaaattaagc gctcagttga cggggagggt tacaacgttg cccagtgtaa   21120
catgaccaaa gactggttcc tggtacaaat gctagctaac tacaacattg gctaccaggg   21180
cttctatatc ccagagagct acaaggaccg catgtactcc ttctttagaa acttccagcc   21240
catgagccgt caggtggtgg atgatactaa atacaaggac taccaacagg tgggcatcct   21300
acaccaacac aacaactctg gatttgttgg ctaccttgcc cccaccatgc gcgaaggaca   21360
ggcctaccct gctaacttcc cctatccgct tataggcaag accgcagttg acagcattac   21420
ccagaaaaag tttctttgcg atcgcaccct ttggcgcatc ccattctcca gtaactttat   21480
gtccatgggc gcactcacag acctgggcca aaaccttctc tacgccaact ccgcccacgc   21540
gctagacatg acttttgagg tggatcccat ggacgagccc acccttcttt atgtttttgtt   21600 tgaagtcttt gacgtggtcc gtgtgcaccg gccgcaccgc ggcgtcatcg aaaccgtgta   21660
cctgcgcacg cccttctcgg ccggcaacgc cacaacataa agaagcaagc aacatcaaca   21720
acagctgccg ccatgggctc cagtgagcag gaactgaaag ccattgtcaa agatcttggt   21780
tgtgggccat attttttggg cacctatgac aagcgctttc caggctttgt ttctccacac   21840
aagctcgcct gcgccatagt caatacggcc ggtcgcgaga ctgggggcgt acactggatg   21900
gcctttgcct ggaacccgca ctcaaaaaca tgctacctct ttgagccctt tggctttttct   21960 gaccagcgac tcaagcaggt ttaccagttt gagtacgagt cactcctgcg ccgtagcgcc   22020
attgcttctt cccccgaccg ctgtataacg ctggaaaagt ccacccaaag cgtacagggg   22080
cccaactcgg ccgcctgtgg actattctgc tgcatgtttc tccacgcctt tgccaactgg   22140
ccccaaactc ccatggatca caaccccacc atgaacctta ttaccggggt acccaactcc   22200
atgctcaaca gtccccaggt acagcccacc ctgcgtcgca accaggaaca gctctacagc   22260
ttcctggagc gccactcgcc ctacttccgc agccacagtg cgcagattag gagcgccact   22320 tcttttttgtc acttgaaaaa catgtaaaaa taatgtacta gagacacttt caataaaggc   22380
aaatgctttt atttgtacac tctcgggtga ttatttaccc ccacccttgc cgtctgcgcc   22440
gtttaaaaat caaaggggtt ctgccgcgca tcgctatgcg ccactggcag gacacgttg   22500 cgatactggt gtttagtgct ccacttaaac tcaggcacaa ccatccgcgg cagctcggtg   22560
aagttttcac tccacaggct gcgcaccatc accaacgcgt ttagcaggtc gggcgccgat   22620
atcttgaagt cgcagttggg gcctccgccc tgcgcgcgcg agttgcgata cacagggttg   22680
cagcactgga acactatcag cgccgggtgg tgcacgctgg ccagcacgct cttgtcggag   22740
```

```
atcagatccg cgtccaggtc ctccgcgttg ctcagggcga acggagtcaa ctttggtagc   22800
tgccttccca aaaagggcgc gtgcccaggc tttgagttgc actcgcaccg tagtggcatc   22860
aaaaggtgac cgtgcccggt ctgggcgtta ggatacagcg cctgcataaa agccttgatc   22920
tgcttaaaag ccacctgagc ctttgcgcct tcagagaaga acatgccgca agacttgccg   22980
gaaaactgat tggccggaca ggccgcgtcg tgcacgcagc accttgcgtc ggtgttggag   23040
atctgcacca catttcggcc ccaccggttc ttcacgatct tggccttgct agactgctcc   23100
ttcagcgcgc gctgcccgtt ttcgctcgtc acatccattt caatcacgtg ctccttattt   23160
atcataatgc ttccgtgtag acacttaagc tcgccttcga tctcagcgca gcggtgcagc   23220
cacaacgcgc agcccgtggg ctcgtgatgc ttgtaggtca cctctgcaaa cgactgcagg   23280
tacgcctgca ggaatcgccc catcatcgtc acaaaggtct tgttgctggt gaaggtcagc   23340
tgcaacccgc ggtgctcctc gttcagccag gtcttgcata cggccgccag agcttccact   23400
tggtcaggca gtagtttgaa gttcgccttt agatcgttat ccacgtggta cttgtccatc   23460
agcgcgcgcg cagcctccat gcccttctcc cacgcagaca cgatcggcac actcagcggg   23520
ttcatcaccg taatttcact ttccgcttcg ctgggctctt cctcttcctc ttgcgtccgc   23580
ataccacgcg ccactgggtc gtcttcattc agccgccgca ctgtgcgctt acctcctttg   23640
ccatgcttga ttagcaccgg tgggttgctg aaacccacca tttgtagcgc cacatcttct   23700
ctttcttcct cgctgtccac gattacctct ggtgatggcg ggcgctcggg cttgggagaa   23760
gggcgcttct ttttcttctt gggcgcaatg gccaaatccg ccgccgaggt cgatggccgc   23820
gggctgggtg tgcgcggcac cagcgcgtct tgtgatgagt cttcctcgtc ctcggactcg   23880
atacgccgcc tcatccgctt ttttgggggc gcccggggag gcggcggcga cggggacggg   23940
gacgacacgt cctccatggt tggggacgt cgcgccgcac cgcgtccgcg ctcggggtg    24000 gtttcgcgct gctcctcttc ccgactggcc atttccttct cctataggca gaaaaagatc   24060
atggagtcag tcgagaagaa ggacagccta accgcccccct ctgagttcgc caccaccgcc   24120
tccaccgatg ccgccaacgc gcctaccacc ttccccgtcg aggcacccc gcttgaggag    24180 gaggaagtga ttatcgagca ggacccaggt tttgtaagcg aagacgacga ggaccgctca   24240
gtaccaacag aggataaaaa gcaagaccag gacaacgcag aggcaaacga ggaacaagtc   24300
gggcgggggg acgaaaggca tggcgactac ctagatgtgg gagacgacgt gctgttgaag   24360
catctgcagc gccagtgcgc cattatctgc gacgcgttgc aagagcgcag cgatgtgccc   24420
ctcgccatag cggatgtcag ccttgcctac gaacgccacc tattctcacc gcgcgtaccc   24480
cccaaacgcc aagaaaacgg cacatgcgag cccaacccgc gcctcaactt ctaccccgta   24540
tttgccgtgc cagaggtgct tgccacctat cacatctttt tccaaaactg caagataccc   24600
ctatcctgcc gtgccaaccg cagccgagcg gacaagcagc tggccttgcg gcagggcgct   24660
gtcatacctg atatcgcctc gctcaacgaa gtgccaaaaa tctttgaggg tcttggacgc   24720
gacgagaagc gcgcggcaaa cgctctgcaa caggaaaaca gcgaaaatga aagtcactct   24780
ggagtgttgg tggaactcga gggtgacaac gcgcgcctag ccgtactaaa acgcagcatc   24840
gaggtcaccc actttgccta cccggcactt aacctacccc ccaaggtcat gagcacagtc   24900
atgagtgagc tgatcgtgcg ccgtgcgcag cccctggaga gggatgcaaa tttgcaagaa   24960
caaacagagg agggcctacc cgcagttggc gacgagcagc tagcgcgctg gcttcaaacg   25020
cgcgagcctg ccgacttgga ggagcgacgc aaactaatga tggccgcagt gctcgttacc   25080
```

-continued

```
gtggagcttg agtgcatgca gcggttcttt gctgacccgg agatgcagcg caagctagag   25140
gaaacattgc actacacctt tcgacagggc tacgtacgcc aggcctgcaa gatctccaac   25200
gtggagctct gcaacctggt ctcctacctt ggaattttgc acgaaaaccg ccttgggcaa   25260
aacgtgcttc attccacgct caagggcgag gcgcgccgcg actacgtccg cgactgcgtt   25320
tacttatttc tatgctacac ctggcagacg gccatgggcg tttggcagca gtgcttggag   25380
gagtgcaacc tcaaggagct gcagaaactg ctaaagcaaa acttgaagga cctatggacg   25440
gccttcaacg agcgctccgt ggccgcgcac ctggcggaca tcattttccc cgaacgcctg   25500
cttaaaaccc tgcaacaggg tctgccagac ttcaccagtc aaagcatgtt gcagaacttt   25560
aggaacttta tcctagagcg ctcaggaatc ttgcccgcca cctgctgtgc acttcctagc   25620
gactttgtgc ccattaagta ccgcgaatgc cctccgccgc tttggggcca ctgctacctt   25680
ctgcagctag ccaactacct tgcctaccac tctgacataa tggaagacgt gagcggtgac   25740
ggtctactgg agtgtcactg tcgctgcaac ctatgcaccc cgcaccgctc cctggtttgc   25800
aattcgcagc tgcttaacga aagtcaaatt atcggtacct ttgagctgca gggtccctcg   25860
cctgacgaaa agtccgcggc tccggggttg aaactcactc cggggctgtg gacgtcggct   25920
taccttcgca aatttgtacc tgaggactac cacgcccacg agattaggtt ctacgaagac   25980
caatcccgcc cgccaaatgc ggagcttacc gcctgcgtca ttacccaggg ccacattctt   26040
ggccaattgc aagccatcaa caaagcccgc caagagtttc tgctacgaaa gggacggggg   26100
gtttacttgg accccagtc cggcgaggag ctcaacccaa tccccccgcc gccgcagccc   26160
tatcagcagc agccgcgggc ccttgcttcc caggatggca cccaaaaaga agctgcagct   26220
gccgccgcca cccacggacg aggaggaata ctgggacagt caggcagagg aggttttgga   26280
cgaggaggag gaggacatga tggaagactg ggagagccta gacgaggaag cttccgaggt   26340
cgaagaggtg tcagacgaaa caccgtcacc ctcggtcgca ttcccctcgc cggcgcccca   26400
gaaatcggca accggttcca gcatggctac aacctccgct cctcaggcgc cgccggcact   26460
gcccgttcgc cgacccaacc gtagatggga caccactgga accagggccg gtaagtccaa   26520
gcagccgccg ccgttagccc aagagcaaca acagcgccaa ggctaccgct catggcgcgg   26580
gcacaagaac gccatagttg cttgcttgca agactgtggg ggcaacatct ccttcgcccg   26640
ccgctttctt ctctaccatc acggcgtggc cttcccccgt aacatcctgc attactaccg   26700
tcatctctac agcccatact gcaccggcgg cagcggcagc ggcagcaaca gcagcggcca   26760
cacagaagca aaggcgaccg gatagcaaga ctctgacaaa gcccaagaaa tccacagcgg   26820
cggcagcagc aggaggagga gcgctgcgtc tggcgcccaa cgaacccgta tcgacccgcg   26880
agcttagaaa caggattttt cccactctgt atgctatatt tcaacagagc aggggccaag   26940
aacaagagct gaaaataaaa aacaggtctc tgcgatccct cacccgcagc tgcctgtatc   27000 acaaagcga agatcagctt cggcgcacg tggaagacgc ggaggctctc ttcagtaaat   27060
actgcgcgct gactcttaag gactagtttc gcgccctttc tcaaatttaa gcgcgaaaac   27120
tacgtcatct ccagcggcca cacccggcgc cagcacctgt cgtcagcgcc attatgagca   27180
aggaaattcc cacgccctac atgtggagtt accagccaca aatgggactt gcggctggag   27240
ctgcccaaga ctactcaacc cgaataaact acatgagcgc gggaccccac atgatatccc   27300
gggtcaacgg aatccgcgcc caccgaaacc gaattctctt ggaacaggcg gctattacca   27360
ccacacctcg taataacctt aatccccgta gttggcccgc tgcctggtg taccaggaaa   27420 gtcccgctcc caccactgtg gtacttccca gagacgccca ggccgaagtt cagatgacta   27480
```

-continued

```
actcaggggc gcagcttgcg ggcggctttc gtcacagggt gcggtcgccc gggcagggta   27540
taactcacct gacaatcaga gggcgaggta ttcagctcaa cgacgagtcg gtgagctcct   27600
cgcttggtct ccgtccggac gggacatttc agatcggcgg cgccggccgt ccttcattca   27660
cgcctcgtca ggcaatccta actctgcaga cctcgtcctc tgagccgcgc tctggaggca   27720
ttggaactct gcaatttatt gaggagtttg tgccatcggt ctactttaac cccttctcgg   27780
gacctcccgg ccactatccg gatcaattta ttcctaactt tgacgcggta aaggactcgg   27840
cggacggcta cgactgaatg ttaagtggag aggcagagca actgcgcctg aaacacctgg   27900
tccactgtcg ccgccacaag tgctttgccc gcgactccgg tgagttttgc tactttgaat   27960
tgcccgagga tcatatcgag ggcccggcgc acggcgtccg gcttaccgcc cagggagagc   28020
ttgcccgtag cctgattcgg gagtttaccc agcgcccccct gctagttgag cgggacaggg   28080
gaccctgtgt tctcactgtg atttgcaact gtcctaacct tggattacat caagatcttt   28140
gttgccatct ctgtgctgag tataataaat acagaaatta aaatatactg gggctcctat   28200
cgccatcctg taaacgccac cgtcttcacc cgcccaagca aaccaaggcg aaccttacct   28260
ggtactttta acatctctcc ctctgtgatt tacaacagtt tcaacccaga cggagtgagt   28320
ctacgagaga acctctccga gctcagctac tccatcagaa aaaacaccac cctccttacc   28380
tgccgggaac gtacgagtgc gtcaccggcc gctgcaccac acctaccgcc tgaccgtaaa   28440
ccagactttt tccggacaga cctcaataac tctgtttacc agaacaggag gtgagcttag   28500 aaaacccta gggtattagg ccaaaggcgc agctactgtg gggtttatga acaattcaag   28560
caactctacg ggctattcta attcaggttt ctctagaatc ggggttgggg ttattctctg   28620
tcttgtgatt ctctttattc ttatactaac gcttctctgc ctaaggctcg ccgcctgctg   28680
tgtgcacatt tgcatttatt gtcagctttt taaacgctgg ggtcgccacc caagatgatt   28740
aggtacataa tcctaggttt actcacccctt gcgtcagccc acggtaccac ccaaaaggtg   28800
gattttaagg agccagcctg taatgttaca ttcgcagctg aagctaatga gtgcaccact   28860
cttataaaat gcaccacaga acatgaaaag ctgcttattc gccacaaaaa caaaattggc   28920
aagtatgctg tttatgctat ttggcagcca ggtgacacta cagagtataa tgttacagtt   28980
ttccagggta aaagtcataa aacttttatg tatacttttc cattttatga aatgtgcgac   29040
attaccatgt acatgagcaa acagtataag ttgtggcccc cacaaaattg tgtggaaaac   29100
actggcactt tctgctgcac tgctatgcta attacagtgc tcgctttggt ctgtaccccta   29160 ctctatatta aatacaaaag cagacgcagc tttattgagg aaaagaaaat gccttaattt   29220
actaagttac aaagctaatg tcaccactaa ctgctttact cgctgcttgc aaaacaaatt   29280
caaaaagtta gcattataat tagaatagga tttaaacccc ccggtcattt cctgctcaat   29340
accattcccc tgaacaattg actctatgtg ggatatgctc cagcgctaca accttgaagt   29400
caggcttcct ggatgtcagc atctgacttt ggccagcacc tgtcccgcgg atttgttcca   29460
gtccaactac agcgacccac cctaacagag atgaccaaca caaccaacgc ggccgccgct   29520
accggactta catctaccac aaatacaccc caagtttctg cctttgtcaa taactgggat   29580
aacttgggca tgtggtggtt ctccatagcg cttatgtttg tatgccttat tattatgtgg   29640
ctcatctgct gcctaaagcg caaacgcgcc cgaccaccca tctatagtcc catcattgtg   29700
ctacacccaa acaatgatgg aatccataga ttggacggac tgaaacacat gttctttct   29760 cttacagtat gattaaatga gacatgattc ctcgagtttt tatattactg acccttgttg   29820
```

```
cgcttttttg tgcgtgctcc acattggctg cggtttctca catcgaagta gactgcattc   29880
cagccttcac agtctatttg ctttacggat ttgtcaccct cacgctcatc tgcagcctca   29940
tcactgtggt catcgccttt atccagtgca ttgactgggt ctgtgtgcgc tttgcatatc   30000
tcagacacca tccccagtac agggacagga ctatagctga gcttcttaga attctttaat   30060
tatgaaattt actgtgactt ttctgctgat tatttgcacc ctatctgcgt tttgttcccc   30120
gacctccaag cctcaaagac atatatcatg cagattcact cgtatatgga atattccaag   30180
ttgctacaat gaaaaaagcg atctttccga agcctggtta tatgcaatca tctctgttat   30240
ggtgttctgc agtaccatct tagccctagc tatatatccc taccttgaca ttggctggaa   30300
acgaatagat gccatgaacc acccaacttt ccccgcgccc gctatgcttc cactgcaaca   30360
agttgttgcc ggcggctttg tcccagccaa tcagcctcgc cccacttctc ccacccccac   30420
tgaaatcagc tactttaatc taacaggagg agatgactga caccctagat ctagaaatgg   30480
acggaattat tacagagcag cgcctgctag aaagacgcag ggcagcggcc gagcaacagc   30540
gcatgaatca agagctccaa gacatggtta acttgcacca gtgcaaaagg ggtatctttt   30600
gtctggtaaa gcaggccaaa gtcacctacg acagtaatac caccggacac cgccttagct   30660
acaagttgcc aaccaagcgt cagaaattgg tggtcatggt gggagaaaag cccattacca   30720
taactcagca ctcggtagaa accgaaggct gcattcactc accttgtcaa ggacctgagg   30780
atctctgcac ccttattaag accctgtgcg gtctcaaaga tcttattccc tttaactaat   30840
aaaaaaaaat aataaagcat cacttactta aaatcagtta gcaaatttct gtccagttta   30900
ttcagcagca cctccttgcc ctcctcccag ctctggtatt gcagcttcct cctggctgca   30960
aactttctcc acaatctaaa tggaatgtca gtttcctcct gttcctgtcc atccgcaccc   31020
actatcttca tgttgttgca gatgaagcgc gcaagaccgt ctgaagatac cttcaacccc   31080
gtgtatccat atgacacgga aaccggtcct ccaactgtgc cttttcttac tcctcccttt   31140
gtatccccca atgggtttca agagagtccc cctggggtac tctctttgcg cctatccgaa   31200
cctctagtta cctccaatgg catgcttgcg ctcaaaatgg caacggcct  ctctctggac   31260 gaggccggca accttacctc ccaaaatgta accactgtga gcccacctct caaaaaaacc   31320
aagtcaaaca taaacctgga aatatctgca cccctcacag ttacctcaga agccctaact   31380
gtggctgccg ccgcacctct aatggtcgcg ggcaacacac tcaccatgca atcacaggcc   31440
ccgctaaccg tgcacgactc caaacttagc attgccaccc aaggacccct cacagtgtca   31500
gaaggaaagc tagccctgca aacatcaggc cccctcacca ccaccgatag cagtaccctt   31560
actatcactg cctcaccccc tctaactact gccactggta gcttgggcat tgacttgaaa   31620
gagcccattt atacacaaaa tggaaaacta ggactaaagt acgggggctcc tttgcatgta   31680 acagacgacc taaacacttt gaccgtagca actggtccag gtgtgactat taataatact   31740
tccttgcaaa ctaaagttac tggagccttg ggttttgatt cacaaggcaa tatgcaactt   31800
aatgtagcag gaggactaag gattgattct caaaacagac gccttatact tgatgttagt   31860
tatccgtttg atgctcaaaa ccaactaaat ctaagactag acagggccc  tctttttata   31920 aactcagccc acaacttgga tattaactac aacaaaggcc tttacttgtt tacagcttca   31980
aacaattcca aaaagcttga ggttaaccta agcactgcca aggggttgat gtttgacgct   32040
acagccatag ccattaatgc aggagatggg cttgaatttg gttcacctaa tgcaccaaac   32100
acaaatcccc tcaaaacaaa aattggccat ggcctagaat ttgattcaaa caaggctatg   32160
gttcctaaac taggaactgg ccttagtttt gacagcacag gtgccattac agtaggaaac   32220
```

-continued

```
aaaaataatg ataagctaac tttgtggacc acaccagctc catctcctaa ctgtagacta   32280
aatgcagaga aagatgctaa actcactttg gtcttaacaa aatgtggcag tcaaatactt   32340
gctacagttt cagttttggc tgttaaaggc agtttggctc caatatctgg aacagttcaa   32400
agtgctcatc ttattataag atttgacgaa aatggagtgc tactaaacaa ttccttcctg   32460
gacccagaat attggaactt tagaaatgga gatcttactg aaggcacagc ctatacaaac   32520
gctgttggat ttatgcctaa cctatcagct tatccaaaat ctcacggtaa aactgccaaa   32580
agtaacattg tcagtcaagt ttacttaaac ggagacaaaa ctaaacctgt aacactaacc   32640
attacactaa acggtacaca ggaaacagga gacacaactc caagtgcata ctctatgtca   32700
ttttcatggg actggtctgg ccacaactac attaatgaaa tatttgccac atcctcttac   32760 acttttcat acattgccca agaataaaga atcgtttgtg ttatgtttca acgtgtttat   32820
ttttcaattg cagaaaattt caagtcattt ttcattcagt agtatagccc caccaccaca   32880
tagcttatac agatcaccgt accttaatca aactcacaga accctagtat tcaacctgcc   32940
acctccctcc caacacacag agtacacagt cctttctccc cggctggcct taaaaagcat   33000
catatcatgg gtaacagaca tattcttagg tgttatattc cacacggttt cctgtcgagc   33060
caaacgctca tcagtgatat taataaactc cccgggcagc tcacttaagt tcatgtcgct   33120
gtccagctgc tgagccacag gctgctgtcc aacttgcggt tgcttaacgg gcggcgaagg   33180
agaagtccac gcctacatgg gggtagagtc ataatcgtgc atcaggatag ggcggtggtg   33240
ctgcagcagc gcgcgaataa actgctgccg ccgccgctcc gtcctgcagg aatacaacat   33300
ggcagtggtc tcctcagcga tgattcgcac cgcccgcagc ataaggcgcc ttgtcctccg   33360
ggcacagcag cgcaccctga tctcacttaa atcagcacag taactgcagc acagcaccac   33420
aatattgttc aaaatcccac agtgcaaggc gctgtatcca aagctcatgg cggggaccac   33480
agaacccacg tggccatcat accacaagcg caggtagatt aagtggcgac ccctcataaa   33540
cacgctggac ataaacatta cctcttttgg catgttgtaa ttcaccacct cccggtacca   33600
tataaacctc tgattaaaca tggcgccatc caccaccatc ctaaaccagc tggccaaaac   33660
ctgcccgccg gctatacact gcagggaacc gggactggaa caatgacagt ggagagccca   33720
ggactcgtaa ccatggatca tcatgctcgt catgatatca atgttggcac aacacaggca   33780
cacgtgcata cacttcctca ggattacaag ctcctcccgc gttagaacca tatcccaggg   33840
aacaacccat tcctgaatca gcgtaaatcc cacactgcag ggaagacctc gcacgtaact   33900
cacgttgtgc attgtcaaag tgttacattc gggcagcagc ggatgatcct ccagtatggt   33960
agcgcgggtt tctgtctcaa aaggaggtag acgatcccta ctgtacggag tgcgccgaga   34020
caaccgagat cgtgttggtc gtagtgtcat gccaaatgga acgccggacg tagtcatatt   34080
tcctgaagca aaaccaggtg cgggcgtgac aaacagatct gcgtctccgg tctcgccgct   34140
tagatcgctc tgtgtagtag ttgtagtata tccactctct caaagcatcc aggcgccccc   34200
tggcttcggg ttctatgtaa actccttcat gcgccgctgc cctgataaca tccaccaccg   34260
cagaataagc cacacccagc caacctacac attcgttctg cgagtcacac acggaggag   34320 cgggaagagc tggaagaacc atgttttttt ttttattcca aaagattatc caaaacctca   34380
aaatgaagat ctattaagtg aacgcgctcc cctccggtgg cgtggtcaaa ctctacagcc   34440
aaagaacaga taatggcatt tgtaagatgt tgcacaatgg cttccaaaag gcaaacggcc   34500
ctcacgtcca agtggacgta aaggctaaac ccttcagggt gaatctcctc tataaacatt   34560
```

```
ccagcacctt caaccatgcc caaataattc tcatctcgcc accttctcaa tatatctcta   34620
agcaaatccc gaatattaag tccggccatt gtaaaaatct gctccagagc gccctccacc   34680
ttcagcctca agcagcgaat catgattgca aaaattcagg ttcctcacag acctgtataa   34740
gattcaaaag cggaacatta acaaaaatac cgcgatcccg taggtccctt cgcagggcca   34800
gctgaacata atcgtgcagg tctgcacgga ccagcgcggc cacttccccg ccaggaacca   34860
tgacaaaaga acccacactg attatgacac gcatactcgg agctatgcta accagcgtag   34920
ccccgatgta agcttgttgc atgggcggcg atataaaatg caaggtgctg ctcaaaaaat   34980
caggcaaagc ctcgcgcaaa aaagaaagca catcgtagtc atgctcatgc agataaaggc   35040
aggtaagctc cggaaccacc acagaaaaag acaccatttt tctctcaaac atgtctgcgg   35100
gtttctgcat aaacacaaaa taaaataaca aaaaacatt taaacattag aagcctgtct   35160
tacaacagga aaaacaaccc ttataagcat aagacggact acggccatgc cggcgtgacc   35220
gtaaaaaaac tggtcaccgt gattaaaaag caccaccgac agctcctcgg tcatgtccgg   35280
agtcataatg taagactcgg taaacacatc aggttgattc acatcggtca gtgctaaaaa   35340
gcgaccgaaa tagcccgggg gaatacatac ccgcaggcgt agagacaaca ttacagcccc   35400
cataggaggt ataacaaaat taataggaga gaaaaacaca taaacacctg aaaaaccctc   35460
ctgcctaggc aaaatagcac cctcccgctc cagaacaaca tacagcgctt ccacagcggc   35520
agccataaca gtcagcctta ccagtaaaaa agaaaaccta ttaaaaaaac accactcgac   35580
acggcaccag ctcaatcagt cacagtgtaa aaaagggcca agtgcagagc gagtatatat   35640
aggactaaaa aatgacgtaa cggttaaagt ccacaaaaaa cacccagaaa accgcacgcg   35700
aacctacgcc cagaaacgaa agccaaaaaa cccacaactt cctcaaatcg tcacttccgt   35760
tttcccacgt tacgtaactt cccatttttaa gaaaactaca attcccaaca catacaagtt   35820
actccgccct aaaacctacg tcacccgccc cgttcccacg ccccgcgcca cgtcacaaac   35880 tccacccccct cattatcata ttggcttcaa tccaaaataa ggtatattat tgatgatg   35938
```

<210> SEQ ID NO 8
<211> LENGTH: 35937
<212> TYPE: DNA
<213> ORGANISM: Human adenovirus type 2

<400> SEQUENCE: 8

```
catcatcata atatacctta ttttggattg aagccaatat gataatgagg gggtggagtt    60
tgtgacgtgg cgcggggcgt gggaacgggg cgggtgacgt agtagtgtgg cggaagtgtg   120
atgttgcaag tgtggcggaa cacatgtaag cgccggatgt ggtaaaagtg acgtttttgg   180
tgtgcgccgg tgtatacggg aagtgacaat tttcgcgcgg ttttaggcgg atgttgtagt   240
aaatttgggc gtaaccaagt aatgtttggc cattttcgcg ggaaaactga ataagaggaa   300
gtgaaatctg aataattctg tgttactcat agcgcgtaat atttgtctag ggccgcgggg   360
actttgaccg tttacgtgga gactcgccca ggtgtttttc tcaggtgttt tccgcgttcc   420
gggtcaaagt tggcgtttta ttattatagt cagctgacgc gcagtgtatt tatacccggt   480
gagttcctca agaggccact cttgagtgcc agcgagtaga gttttctcct ccagccgct    540 ccgacaccgg gactgaaaat gagacatatt atctgccacg gaggtgttat taccgaagaa   600
atggccgcca gtcttttgga ccagctgatc gaagaggtac tggctgataa tcttccacct   660
cctagccatt ttgaaccacc taccccttcac gaactgtatg atttagacgt gacggccccc   720
gaagatccca cgaggaggc ggtttcgcag atttttcccg agtctgtaat gttggcggtg   780
```

```
caggaaggga ttgacttatt cactttttccg ccggcgcccg gttctccgga gccgcctcac    840
ctttcccggc agcccgagca gccggagcag agagccttgg gtccggtttc tatgccaaac    900
cttgtgccgg aggtgatcga tcttacctgc cacgaggctg gctttccacc cagtgacgac    960
gaggatgaag agggtgagga gtttgtgtta gattatgtgg agcaccccgg gcacggttgc   1020
aggtcttgtc attatcaccg gaggaatacg ggggacccag atattatgtg ttcgctttgc   1080
tatatgagga cctgtggcat gtttgtctac agtaagtgaa aattatgggc agtcggtgat   1140
agagtggtgg gtttggtgtg gtaatttttt tttaattttt acagttttgt ggtttaaaga   1200
attttgtatt gtgatttttt aaaaggtcct gtgtctgaac ctgagcctga gcccgagcca   1260
gaaccggagc ctgcaagacc tacccggcgt cctaaattgg tgcctgctat cctgagacgc   1320
ccgacatcac ctgtgtctag agaatgcaat agtagtacgg atagctgtga ctccggtcct   1380
tctaacacac ctcctgagat acacccggtg gtcccgctgt gccccattaa accagttgcc   1440
gtgagagttg gtgggcgtcg ccaggctgtg gaatgtatcg aggacttgct taacgagtct   1500
gggcaacctt tggacttgag ctgtaaacgc cccaggccat aaggtgtaaa cctgtgattg   1560
cgtgtgtggt taacgccttt gtttgctgaa tgagttgatg taagtttaat aaagggtgag   1620
ataatgttta acttgcatgg cgtgttaaat ggggcggggc ttaaagggta tataatgcgc   1680
cgtgggctaa tcttggttac atctgacctc atggaggctt gggagtgttt ggaagatttt   1740
tctgctgtgc gtaacttgct ggaacagagc tctaacagta cctcttggtt ttggaggttt   1800 ctgtgggggct cctcccaggc aaagttagtc tgcagaatta aggaggatta caagtgggaa   1860
tttgaagagc ttttgaaatc ctgtggtgag ctgtttgatt ctttgaatct gggtcaccag   1920
gcgcttttcc aagagaaggt catcaagact ttggattttt ccacaccggg gcgcgctgcg   1980
gctgctgttg cttttttgag ttttataaag gataaatgga gcgaagaaac ccatctgagc   2040
ggggggtacc tgctggattt tctggccatg catctgtgga gagcggtggt gagacacaag   2100
aatcgcctgc tactgttgtc ttccgtccgc ccggcaataa taccgacgga ggagcaacag   2160
caggaggaag ccaggcggcg gcggcggcag gagcagagcc catggaaccc gagagccggc   2220
ctggaccctc gggaatgaat gttgtacagg tggctgaact gtttccagaa ctgagacgca   2280
ttttaaccat taacgaggat gggcaggggc taaaggggggt aaagagggag cggggggctt   2340
ctgaggctac agaggaggct aggaatctaa cttttagctt aatgaccaga caccgtcctg   2400
agtgtgttac ttttcagcag attaaggata attgcgctaa tgagcttgat ctgctggcgc   2460
agaagtattc catagagcag ctgaccactt actggctgca gccaggggat gattttgagg   2520
aggctattag ggtatatgca aaggtggcac ttaggccaga ttgcaagtac aagattagca   2580
aacttgtaaa tatcaggaat tgttgctaca tttctgggaa cggggccgag gtggagatag   2640
atacggagga tagggtggcc tttagatgta gcatgataaa tatgtggccg ggggtgcttg   2700
gcatggacgg ggtggttatt atgaatgtga ggttactgg tcccaatttt agcggtacgg   2760
ttttcctggc caataccaat cttatcctac acggtgtaag cttctatggg tttaacaata   2820
cctgtgtgga agcctggacc gatgtaaggg ttcggggctg tgccttttac tgctgctgga   2880 aggggggtggt gtgtcgcccc aaaagcaggg cttcaattaa gaaatgcctg tttgaaaggt   2940
gtaccttggg tatcctgtct gagggtaact ccagggtgcg ccacaatgtg gcctccgact   3000
gtggttgctt catgctagtg aaaagcgtgg ctgtgattaa gcataacatg gtgtgtggca   3060
actgcgagga cagggcctct cagatgctga cctgctcgga cggcaactgt cacttgctga   3120
```

-continued

```
agaccattca cgtagccagc cactctcgca aggcctggcc agtgtttgag cacaacatac    3180
tgacccgctg ttccttgcat ttgggtaaca ggagggggt gttcctacct taccaatgca      3240
atttgagtca cactaagata ttgcttgagc ccgagagcat gtccaaggtg aacctgaacg     3300
gggtgtttga catgaccatg aagatctgga aggtgctgag gtacgatgag acccgcacca     3360
ggtgcagacc ctgcgagtgt ggcggtaaac atattaggaa ccagcctgtg atgctggatg     3420
tgaccgagga gctgaggccc gatcacttgg tgctggcctg cacccgcgct gagtttggct     3480
ctagcgatga agatacagat tgaggtactg aaatgtgtgg gcgtggctta agggtgggaa     3540
agaatatata aggtggggt ctcatgtagt tttgtatctg ttttgcagca gccgccgcca      3600
tgagcgccaa ctcgtttgat ggaagcattg tgagctcata tttgacaacg cgcatgcccc     3660
catgggccgg ggtgcgtcag aatgtgatgg gctccagcat tgatggtcgc cccgtcctgc     3720
ccgcaaactc tactaccttg acctacgaga ccgtgtctgg aacgccgttg gagactgcag     3780
cctccgccgc cgcttcagcc gctgcagcca ccgcccgcgg gattgtgact gactttgctt     3840
tcctgagccc gcttgcaagc agtgcagctt cccgttcatc cgcccgcgat gacaagttga     3900
cggctctttt ggcacaattg gattctttga cccgggaact taatgtcgtt tctcagcagc     3960
tgttggatct gcgccagcag gtttctgccc tgaaggcttc ctccctccc aatgcggttt      4020 aaaacataaa taaaaaccag actctgtttg gattttgatc aagcaagtgt cttgctgtct     4080
ttatttaggg gttttgcgcg cgcggtaggc ccgggaccag cggtctcggt cgttgagggt     4140
cctgtgtatt ttttccagga cgtggtaaag gtgactctgg atgttcagat acatgggcat     4200
aagcccgtct ctggggtgga ggtagcacca ctgcagagct tcatgctgcg gggtggtgtt     4260
gtagatgatc cagtcgtagc aggagcgctg ggcgtggtgc ctaaaaatgt ctttcagtag     4320
caagctgatt gccaggggca ggcccttggt gtaagtgttt acaaagcggt taagctggga     4380
tgggtgcata cgtggggata tgagatgcat cttggactgt attttaggt tggctatgtt      4440 cccagccata tccctccggg gattcatgtt gtgcagaacc accagcacag tgtatccggt     4500
gcacttggga aatttgtcat gtagcttaga aggaaatgcg tggaagaact tggagacgcc     4560
cttgtgacct ccgagatttt ccatgcattc gtccataatg atggcaatgg cccacgggc      4620 ggcggcctgg gcgaagatat ttctgggatc actaacgtca tagttgtgtt ccaggatgag     4680
atcgtcatag gccatttta caaagcgcgc gcgagggtg ccagactgcg gtataatggt       4740
tccatccggc ccaggggcgt agttaccctc acagatttgc atttcccacg ctttgagttc     4800
agatgggggg atcatgtcta cctgcgggc gatgaagaaa accgtttccg gggtagggga      4860
gatcagctgg gaagaaagca ggttcctgag cagctgcgac ttaccgcagc cggtgggccc     4920
gtaaatcaca cctattaccg gctgcaactg gtagttaaga gagctgcagc tgccgtcatc     4980
cctgagcagg ggggccactt cgttaagcat gtccctgact tgcatgtttt ccctgaccaa     5040
atgcgccaga aggcgctcgc cgcccagcga tagcagttct tgcaaggaag caaagttttt     5100
caacggtttg aggccgtccg ccgtaggcat gctttgagc gtttgaccaa gcagttccag      5160
gcggtcccac agctcggtca cgtgctctac ggcatctcga tccagcatat ctcctcgttt     5220
cgcgggttgg ggcggctttc gctgtacggc agtagtcggt gctcgtccag acgggccagg     5280
gtcatgtctt tccacgggcg cagggtcctc gtcagcgtag tctgggtcac ggtgaagggg     5340
tgcgctccgg gctgcgcgct ggccaggggt cgcttgaggc tggtcctgct ggtgctgaag     5400
cgctgccggt cttcgccctg cgcgtcgccc aggtagcatt tgaccatggt gtcatagtcc     5460 agccctccg cggcgtggcc cttggcgcgc agcttgccct tggaggaggc gccgcacgag       5520
```

-continued

```
gggcagtgca gacttttaag ggcgtagagc ttgggcgcga gaaataccga ttccggggag    5580
taggcatccg cgccgcaggc cccgcagacg gtctcgcatt ccacgagcca ggtgagctct    5640
ggccgttcgg ggtcaaaaac caggtttccc ccatgctttt tgatgcgttt cttacctctg    5700
gtttccatga gccggtgtcc acgctcggtg acgaaaaggc tgtccgtgtc cccgtataca    5760
gacttgagag gcctgtcctc gagcggtgtt ccgcggtcct cctcgtatag aaactcggac    5820
cactctgaga cgaaggctcg cgtccaggcc agcacgaagg aggctaagtg ggaggggtag    5880
cggtcgttgt ccactagggg gtccactcgc tccagggtgt gaagacacat gtcgccctct    5940
tcggcatcaa ggaaggtgat tggtttatag gtgtaggcca cgtgaccggg tgttcctgaa    6000
ggggggctat aaaagggggt gggggcgcgt tcgtcctcac tctcttccgc atcgctgtct    6060
gcgagggcca gctgttgggg tgagtactcc ctctcaaaag cgggcatgac ttctgcgcta    6120
agattgtcag tttccaaaaa cgaggaggat ttgatattca cctggcccgc ggtgatgcct    6180
ttgagggtgg ccgcgtccat ctggtcagaa aagacaatct ttttgttgtc aagcttggtg    6240
gcaaacgacc cgtagagggc gttggacagc aacttggcga tggagcgcag ggtttggttt    6300
ttgtcgcgat cggcgcgctc cttggccgcg atgtttagct gcacgtattc gcgcgcaacg    6360
caccgccatt cgggaaagac ggtggtgcgc tcgtcgggca ccaggtgcac gcgccaaccg    6420
cggttgtgca gggtgacaag gtcaacgctg gtggctacct ctccgcgtag gcgctcgttg    6480
gtccagcaga ggcggccgcc cttgcgcgaa cagaatggcg gtagtgggtc tagctgcgtc    6540
tcgtccgggg ggtctgcgtc cacggtaaag accccgggca gcaggcgcgc gtcgaagtag    6600
tctatcttgc atccttgcaa gtctagcgcc tgctgccatg cgcgggcggc aagcgcgcgc    6660
tcgtatgggt tgagtggggg accccatggc atggggtggg tgagcgcgga ggcgtacatg    6720
ccgcaaatgt cgtaaacgta gaggggctct ctgagtattc caagatatgt agggtagcat    6780
cttccaccgc ggatgctggc gcgcacgtaa tcgtatagtt cgtgcgaggg agcgaggagg    6840
tcgggaccga ggttgctacg ggcgggctgc tctgctcgga agactatctg cctgaagatg    6900
gcatgtgagt tggatgatat ggttggacgc tggaagacgt tgaagctggc gtctgtgaga    6960
cctaccgcgt cacgcacgaa ggaggcgtag gagtcgcgca gcttgttgac cagctcggcg    7020
gtgacctgca cgtctagggc gcagtagtcc agggtttcct tgatgatgtc atacttatcc    7080
tgtccctttt ttttccacag ctcgcggttg aggacaaact cttcgcggtc tttccagtac    7140
tcttggatcg gaaacccgtc ggcctccgaa cggtaagagc ctagcatgta gaactggttg    7200
acggcctggt aggcgcagca tcccttttct acgggtagcg cgtatgcctg cgcggccttc    7260
cggagcgagg tgtgggtgag cgcaaaggtg tccctaacca tgactttgag gtactggtat    7320
ttgaagtcag tgtcgtcgca tccgccctgc tcccagagca aaaagtccgt gcgctttttg    7380
gaacgcgggt ttggcagggc gaaggtgaca tcgttgaaaa gtatctttcc cgcgcgaggc    7440
ataaagttgc gtgtgatgcg gaagggtccc ggcacctcgg aacggttgtt aattacctgg    7500
gcggcgagca cgatctcgtc gaagccgttg atgttgtggc ccacgatgta aagttccaag    7560
aagcgcgggg tgcccttgat ggagggcaat tttttaagtt cctcgtaggt gagctcctca    7620
ggggagctga gcccgtgttc tgacagggcc cagtctgcaa gatgagggtt ggaagcgacg    7680
aatgagctcc acaggtcacg ggccattagc atttgcaggt ggtcgcgaaa ggtcctaaac    7740
tggcgaccta tggccatttt ttctgggggtg atgcagtaga aggtaagcgg gtcttgttcc    7800
cagcggtccc atccaaggtc cacggctagg tctcgcgcgg cggtcaccag aggctcatct    7860
```

-continued

```
ccgccgaact tcataaccag catgaagggc acgagctgct tcccaaaggc ccccatccaa    7920
gtataggtct ctacatcgta ggtgacaaag agacgctcgg tgcgaggatg cgagccgatc    7980
gggaagaact ggatctcccg ccaccagttg gaggagtggc tgttgatgtg gtgaaagtag    8040
aagtccctgc gacgggccga acactcgtgc tggcttttgt aaaaacgtgc gcagtactgg    8100
cagcggtgca cgggctgtac atcctgcacg aggttgacct gacgaccgcg cacaaggaag    8160
cagagtggga atttgagccc ctcgcctggc gggtttggct ggtggtcttc tacttcggct    8220
gcttgtcctt gaccgtctgg ctgctcgagg ggagttatgg tggatcggac caccacgccg    8280
cgcgagccca aagtccagat gtccgcgcgc ggcggtcgga gcttgatgac aacatcgcgc    8340
agatgggagc tgtccatggt ctggagctcc cgcggcgaca ggtcaggcgg gagctcctgc    8400
aggtttacct cgcatagccg ggtcaggcg cgggctaggt ccaggtgata cctgatttcc    8460
aggggctggt tggtggcggc gtcgatgact tgcaagaggc cgcatccccg cggcgcgact    8520
acggtaccgc gcggcgggcg gtgggccgcg ggggtgtcct tggatgatgc atctaaaagc    8580
ggtgacgcgg gcgggccccc ggaggtaggg ggggctcggg accgccggg agaggggca    8640 ggggcacgtc ggcgccgcgc gcgggcagga gctggtgctg cgcgcggagg ttgctggcga    8700
acgcgacgac gcggcggttg atctcctgaa tctggcgcct ctgcgtgaag acgacgggcc    8760
cggtgagctt gaacctgaaa gagagttcga cagaatcaat ttcggtgtcg ttgacggcgg    8820
cctggcgcaa aatctcctgc acgtctcctg agttgtcttg ataggcgatt tcggccatga    8880
actgctcgat ctcttcctcc tggagatctc cgcgtccggc tcgctccacg gtggcggcga    8940
ggtcgttgga gatgcgggcc atgagctgcg agaaggcgtt gaggcctccc tcgttccaga    9000
cgcggctgta gaccacgccc ccttcggcat cgcgggcgcg catgaccacc tgcgcgagat    9060
tgagctccac gtgccgggcg aagacggcgt agtttcgcag gcgctgaaag aggtagttga    9120
gggtggtggc ggtgtgttct gccacgaaga agtacataac ccagcgtcgc aacgtggatt    9180
cgttgatatc ccccaaggcc tcaaggcgct ccatggcctc gtagaagtcc acggcgaagt    9240
tgaaaaactg ggagttgcgc gccgacacgg ttaactcctc ctccagaaga cggatgagct    9300
cggcgacagt gtcgcgcacc tcgcgctcaa aggctacagg ggcctcttct tcttcaatct    9360
cctcttccat aagggcctcc ccttcttctt cttcttctgg cggcggtggg ggaggggga    9420 cacggcggcg acgacggcgc accgggaggc ggtcgacaaa gcgctcgatc atctccccgc    9480
ggcgacggcg catggtctcg gtgacggcgc ggccgttctc gcggggcgc agttggaaga    9540 cgccgcccgt catgtcccgg ttatgggttg gcgggggct gccgtgcggc agggatacgg    9600
cgctaacgat gcatctcaac aattgttgtg taggtactcc gccaccgagg gacctgagcg    9660
agtccgcatc gaccggatcg gaaaacctct cgagaaaggc gtctaaccag tcacagtcgc    9720
aaggtaggct gagcaccgtg gcgggcggca gcgggtggcg gtcggggttg tttctggcgg    9780
aggtgctgct gatgatgtaa ttaaagtagg cggtcttgag acggcggatg gtcgacagaa    9840
gcaccatgtc cttgggtccg gcctgctgaa tgcgcaggcg gtcggccatg ccccaggctt    9900
cgttttgaca tcggcgcagg tctttgtagt agtcttgcat gagcctttct accggcactt    9960
cttcttctcc ttcctcttgt cctgcatctc ttgcatctat cgctacggcg gcggcggagt    10020
ttggccgtag gtggcgccct cttcctccca tgcgtgtgac cccgaagccc ctcatcggct    10080
gaagcagggc caggtcggcg acaacgcgct cggctaatat ggcctgctgc acctgcgtga    10140
gggtagactg gaagtcatcc atgtccacaa agccggtggta tgcgcccgtg ttgatggtgt    10200
aagtgcagtt ggccataacg gaccagttaa cggtctggtg acccggctgc gagagctcgg    10260
```

-continued

```
tgtacctgag acgcgagtaa gcccttgagt caaagacgta gtcgttgcaa gtccgcacca   10320
ggtactgata tcccaccaaa aagtgcggcg gcggctggcg gtagaggggc cagcgtaggg   10380
tggccggggc tccggggggcg aggtcttcca acataaggcg atgatatccg tagatgtacc   10440
tggacatcca ggtgatgccg gcggcggtgg tggaggcgcg cggaaagtcg cggacgcggt   10500
tccagatgtt gcgcagcggc aaaaagtgct ccatggtcgg gacgctctgg ccggtgaggc   10560
gtgcgcagtc gttgacgctc tagaccgtgc aaaaggagag cctgtaagcg ggcactcttc   10620
cgtggtctgg tggataaatt cgcaagggta tcatggcgga cgaccggggt tcgaaccccg   10680
gatccggccg tccgccgtga tccatgcggt taccgcccgc gtgtcgaacc caggtgtgcg   10740
acgtcagaca acgggggagc gctccttttg gcttccttcc aggcgcggcg gctgctgcgc   10800
tagctttttt ggccactggc cgcgcgcggc gtaagcggtt aggctggaaa gcgaaagcat   10860
taagtggctc gctccctgta gccggagggt tattttccaa gggttgagtc gcaggacccc   10920
cggttcgagt ctcgggccgg ccggactgcg gcgaacgggg gtttgcctcc ccgtcatgca   10980
agaccccgct tgcaaattcc tccggaaaca gggacgagcc cctttttttgc ttttcccaga   11040 tgcatccggt gctgcggcag atgcgccccc ctcctcagca gcggcaagag caagagcagc   11100
ggcagacatg cagggcaccc tcccctcctc ctaccgcgtc aggaggggca acatccgcgg   11160
ctgacgcggc ggcagatggt gattacgaac ccccgcggcg ccgggcccgg cactacctgg   11220
acttggagga gggcgagggc ctggcgcggc taggagcgcc ctctcctgag cgacacccaa   11280
gggtgcagct gaagcgtgac acgcgcgagg cgtacgtgcc gcggcagaac ctgtttcgcg   11340
accgcgaggg agaggagccc gaggagatgc gggatcgaaa gttccacgca gggcgcgagt   11400
tgcggcatgg cctgaaccgc gagcggttgc tgcgcgagga ggactttgag cccgacgcgc   11460
ggaccgggat tagtcccgcg cgcgcacacg tggcggccgc cgacctggta accgcgtacg   11520
agcagacggt gaaccaggag attaactttc aaaaaagctt taacaaccac gtgcgcacgc   11580
ttgtggcgcg cgaggaggtg gctataggac tgatgcatct gtgggacttt gtaagcgcgc   11640
tggagcaaaa cccaaatagc aagccgctca tggcgcagct gttccttata gtgcagcaca   11700
gcagggacaa cgaggcattc agggatgcgc tgctaaacat agtagagccc gagggccgct   11760
ggctgctcga tttgataaac attctgcaga gcatagtggt gcaggagcgc agcttgagcc   11820
tggctgacaa ggtggccgcc attaactatt ccatgctcag tctgggcaag ttttacgccc   11880
gcaagatata ccatacccct tacgttccca tagacaagga ggtaaagatc gaggggttct   11940
acatgcgcat ggcgttgaag gtgcttacct tgagcgacga cctgggcgtt tatcgcaacg   12000
agcgcatcca caaggccgtg agcgtgagcc ggcggcgcga gctcagcgac cgcgagctga   12060
tgcacagcct gcaaagggcc ctggctggca cgggcagcgg cgatagagag gccgagtcct   12120
actttgacgc gggcgctgac ctgcgctggg ccccaagccg acgcgccctg gaggcagctg   12180
gggccggacc tggctggcg gtggcacccg cgcgcgctgg caacgtcggc ggcgtggagg   12240
aatatgacga ggacgatgag tacgagccag aggacggcga gtactaagcg gtgatgtttc   12300
tgatcagatg atgcaagacg caacggaccc ggcggtgcgg gcggcgctgc agagccagcc   12360
gtccggcctt aactccacgg acgactggcg ccaggtcatg accgcatca tgtcgctgac   12420 tgcgcgtaac cctgacgcgt tccggcagca gccgcaggcc aaccggctct ccgcaattct   12480
ggaagcggtg gtcccggcgc gcgcaaaccc cacgcacgag aaggtgctgg cgatcgtaaa   12540
cgcgctggcc gaaaacaggg ccatccggcc cgatgaggcc ggcctggtct acgacgcgct   12600
```

-continued

```
gcttcagcgc gtggctcgtt acaacagcgg caacgtgcag accaacctgg accggctggt   12660
gggggatgtg cgcgaggccg tggcgcagcg tgagcgcgcg cagcagcagg gcaacctggg   12720
ctccatggtt gcactaaacg ccttcctgag tacacagccc gccaacgtgc cgcggggaca   12780
ggaggactac accaactttg tgagcgcact gcggctaatg gtgactgaga caccgcaaag   12840
tgaggtgtac cagtccgggc cagactattt tttccagacc agtagacaag gcctgcagac   12900
cgtaaacctg agccaggctt tcaagaactt gcaggggctg tggggggtgc gggctcccac   12960
aggcgaccgc gcgaccgtgt ctagcttgct gacgcccaac tcgcgcctgt tgctgctgct   13020
aatagcgccc ttcacggaca gtggcagcgt gtccccgggac acatacctag gtcacttgct   13080
gacactgtac cgcgaggcca taggtcaggc gcatgtggac gagcatactt ccaggagat   13140 tacaagtgtc agccgcgcgc tggggcagga ggacacgggc agcctggagg caaccctgaa   13200
ctacctgctg accaaccggc ggcagaagat cccctcgttg cacagtttaa acagcgagga   13260
ggagcgcatc ttgcgctatg tgcagcagag cgtgagcctt aacctgatgc gcgacggggt   13320
aacgcccagc gtggcgctgg acatgaccgc gcgcaacatg gaaccgggca tgtatgcctc   13380
aaaccggccg tttatcaatc gcctaatgga ctacttgcat cgcgcggccg ccgtgaaccc   13440
cgagtatttc accaatgcca tcttgaaccc gcactggcta ccgcccctg gtttctacac   13500 cggggggattt gaggtgcccg agggtaacga tggattcctc tgggacgaca tagacgacag   13560 cgtgtttttcc ccgcaaccgc agaccctgct agagttgcaa cagcgcgagc aggcagaggc   13620
ggcgctgcga aaggaaagct tccgcaggcc aagcagcttg tccgatctag gcgctgcggc   13680
cccgcggtca gatgcgagta gcccatttcc aagcttgata gggtctttta ccagcactcg   13740
caccacccgc ccgcgcctgc tgggcgagga ggagtaccta aacaactcgc tgctgcagcc   13800
gcagcgcgaa aagaacctgc ctccggcatt tcccaacaac gggatagaga gcctagtgga   13860
caagatgagt agatggaaga cgtatgcgca ggagcacagg gatgtgcccg gcccgcgccc   13920
gcccacccgt cgtcaaaggc acgaccgtca gcggggtctg gtgtgggagg acgatgactc   13980
ggcagacgac agcagcgtcc tggatttggg agggagtggc aacccgtttg cgcaccttcg   14040
ccccaggctg gggagaatgt tttaaaaaaa aaaaaaaaa gcatgatgca aaataaaaaa   14100
ctcaccaagg ccatggcacc gagcgttggt tttcttgtat tcccccttagt atgcagcgcg   14160 cggcgatgta tgaggaaggt cctcctccct cctacgagag cgtggtgagc gcggcgccag   14220
tggcggcggc gctgggttcc cccttcgatg ctcccctgga cccgccgttt gtgcctccgc   14280
ggtacctgcg gcctaccggg gggagaaaca gcatccgtta ctctgagttg gcaccccctat   14340 tcgacaccac ccgtgtgtac cttgtggaca acaagtcaac ggatgtggca tccctgaact   14400
accagaacga ccacagcaac tttctaacca cggtcattca aaacaatgac tacagcccgg   14460
gggaggcaag cacacagacc atcaatcttg acgaccgttc gcactggggc ggcgacctga   14520
aaaccatcct gcataccaac atgccaaatg tgaacgagtt catgtttacc aataagttta   14580
aggcgcgggt gatggtgtcg cgctcgctta ctaaggacaa acaggtggag ctgaaatatg   14640
agtgggtgga gttcacgctg cccgagggca actactccga gaccatgacc atagacctta   14700
tgaacaacgc gatcgtggag cactacttga aagtgggcag gcagaacggg gttctggaaa   14760
gcgacatcgg ggtaaagttt gacacccgca acttcagact ggggtttgac ccagtcactg   14820
gtcttgtcat gcctggggta tatacaaacg aagccttcca tccagacatc attttgctgc   14880
caggatgcgg ggtggacttc acccacagcc gcctgagcaa cttgttgggc atccgcaagc   14940
ggcaaccctt ccaggagggc tttaggatca cctacgatga cctggagggt ggtaacattc   15000
```

-continued

```
ccgcactgtt ggatgtggac gcctaccagg caagcttaaa agatgacacc gaacagggcg    15060
gggatggcgc aggcggcggc aacaacagtg gcagcggcgc ggaagagaac tccaacgcgg    15120
cagccgcggc aatgcagccg gtggaggaca tgaacgatca tgccattcgc ggcgacacct    15180
ttgccacacg ggcggaggag aagcgcgctg aggccgaggc agcggcagaa gctgccgccc    15240
ccgctgcgca acccgaggtc gagaagcctc agaagaaacc ggtgatcaaa cccctgacag    15300
aggacagcaa gaaacgcagt tacaacctaa taagcaatga cagcaccttc acccagtacc    15360
gcagctggta ccttgcatac aactacggcg accctcagac cgggatccgc tcatggaccc    15420
tcctttgcac tcctgacgta acctgcggct cggagcaggc ctactggtcg ttgccagaca    15480
tgatgcaaga ccccgtgacc ttccgctcca cgagccagat cagcaacttt ccggtggtgg    15540
gcgccgagct gttgcccgtg cactccaaga gcttctacaa cgaccaggcc gtctactccc    15600
agctcatccg ccagtttacc tctctgaccc acgtgttcaa tcgctttccc gagaaccaga    15660
ttttggcgcg cccgccagcc cccaccatca ccaccgtcag tgaaaacgtt cctgctctca    15720
cagatcacgg gacgctaccg ctgcgcaaca gcatcggagg agtccagcga gtgaccatta    15780
ctgacgccag acgccgcacc tgcccctacg tttacaaggc cctgggcata gtctcgccgc    15840
gcgtcctatc gagccgcact ttttgagcaa acatgtccat ccttatatcg cccagcaata    15900
acacaggctg gggcctgcgc ttcccaagca agatgtttgg cggggcaaag aagcgctccg    15960
accaacaccc agtgcgcgtg cgcgggcact accgcgcgcc ctggggcgcg cacaaacgcg    16020
gccgcactgg gcgcaccacc gtcgatgacg ccattgacgc ggtggtggag gaggcgcgca    16080
actacacgcc cacgccgcca ccagtgtcca cagtggacgc ggccattcag accgtggtgc    16140
gcggagcccg gcgttatgct aaaatgaaga gacggcggag gcgcgtagca cgtcgccacc    16200
gccgccgacc cggcactgcc gcccaacgcg cggcggcggc cctgcttaac cgcgcacgtc    16260
gcaccggccg acgggcggcc atgcgggccg ctcgaaggct ggccgcgggt attgtcactg    16320 tgcccccccag gtccaggcga cgagcggccg ccgcagcagc cgcggccatt agtgctatga    16380
ctcagggtcg caggggcaac gtgtactggg tgcgcgactc ggttagcggc ctgcgcgtgc    16440
ccgtgcgcac ccgcccccccg cgcaactaga ttgcaagaaa aaactactta gactcgtact    16500
gttgtatgta tccagcggcg gcggcgcgca acgaagctat gtccaagcgc aaaatcaaag    16560
aagagatgct ccaggtcatc gcgccggaga tctatggccc cccgaagaag gaagagcagg    16620
attacaagcc ccgaaagcta aagcgggtca aaaagaaaaa gaaagatgat gatgatgatg    16680
aacttgacga cgaggtggaa ctgctgcacg caaccgcgcc caggcggcgg gtacagtgga    16740
aaggtcgacg cgtaagacgt gttttgcgac ccggcaccac cgtagttttt acgcccggtg    16800
agcgctccac ccgcacctac aagcgcgtgt atgatgaggt gtacggcgac gaggacctgc    16860
ttgagcaggc caacgagcgc ctcgggggagt ttgcctacgg aaagcggcat aaggacatgt    16920
tggcgttgcc gctggacgag ggcaacccaa cacctagcct aaagcccgtg acactgcagc    16980
aggtgctgcc cacgcttgca ccgtccgaag aaaagcgcgg cctaaagcgc gagtctggtg    17040
acttggcacc caccgtgcag ctgatggtac ccaagcgcca gcgactggaa gatgtcttgg    17100
aaaaaatgac cgtggagcct gggctggagc ccgaggtccg cgtgcggcca atcaagcagg    17160
tggcaccggg actgggcgtg cagaccgtgg acgttcagat acccaccacc agtagcacta    17220
gtattgccac tgccacagag ggcatggaga cacaaacgtc cccggttgcc tcggcggtgg    17280
cagatgccgc ggtgcaggcg gccgctgcgg ccgcgtccaa aacctctacg gaggtgcaaa    17340
```

-continued

```
cggacccgtg gatgtttcgc gtttcagccc cccggcgccc gcgccgttcc aggaagtacg   17400
gcaccgccag cgcactactg cccgaatatg ccctacatcc ttccatcgcg cctacccccg   17460
gctatcgtgg ctacacctac cgccccagaa gacgagcgac tacccgacgc cgaaccacca   17520
ctggaacccg ccgccgccgt cgccgtcgcc agcccgtgct ggccccgatt tccgtgcgca   17580
gggtggctcg cgaaggaggc aggaccctgg tgctgccaac agcgcgctac caccccagca   17640
tcgtttaaaa gccggtcttt gtggttcttg cagatatggc cctcacctgc cgcctccgtt   17700
tcccggtgcc gggattccga ggaagaatgc accgtaggag gggcatggcc ggccacggcc   17760
tgacgggcgg catgcgtcgt cgcgcaccacc ggcggcggcg cgcgtcgcac cgtcgcatgc   17820
gcggcggtat cctgcccctc cttattccac tgatcgccgc ggcgattggc gccgtgcccg   17880
gaattgcatc cgtggccttg caggcgcaga gacactgatt aaaaacaagt tgcatgtgga   17940
aaaatcaaaa taaaaagtct ggagtctcac gctcgcttgg tcctgtaact attttgtaga   18000
atggaagaca tcaactttgc gtctctggcc ccgcgacacg gctcgcgccc gttcatggga   18060
aactggcaag atatcggcac cagcaatatg agcggtggcg ccttcagctg gggctcgctg   18120
tggagcggca ttaaaaattt cggttccacc attaagaact atggcagcaa ggcctggaac   18180
agcagcacag gccagatgct gagggacaag ttgaaagagc aaaatttcca acaaaaggtg   18240
gtagatggcc tggcctctgg cattagcggg gtggtggacc tggccaacca ggcagtgcaa   18300
aataagatta acagtaagct tgatccccgc cctcccgtag aggagcctcc accggccgtg   18360
gagacagtgt ctccagaggg gcgtggcgaa aagcgtccgc ggcccgacag ggaagaaact   18420
ctggtgacgc aaatagatga gcctccctcg tacgaggagg cactaaagca aggcctgccc   18480
accacccgtc ccatcgcgcc catggctacc ggagtgctgg gccagcacac acctgtaacg   18540
ctggacctgc ctcccccgc tgacacccag cagaaacctg tgctgccagg gccgtccgcc   18600
gttgttgtaa cccgccctag ccgcgcgtcc ctgcgccgtg ccgccagcgg tccgcgatcg   18660
atgcggcccg tagccagtgg caactggcaa agcacactga acagcatcgt gggtctgggg   18720
gtgcaatccc tgaagcgccg acgatgcttc taaatagcta acgtgtcgta tgtgtcatgt   18780
atgcgtccat gtcgccgcca gaggagctgc tgagccgccg tgcgcccgct ttccaagatg   18840
gctacccctt cgatgatgcc gcagtggtct tacatgcaca tctcgggcca ggacgcctcg   18900
gagtacctga gccccgggct ggtgcagttt gcccgcgcca ccgagacgta cttcagcctg   18960
aataacaagt ttagaaaccc cacggtggca cctacgcacg acgtaaccac agaccggtcc   19020
cagcgtttga cgctgcggtt catccctgtg gaccgcgagg ataccgcgta ctcgtacaaa   19080
gcgcggttca ccctggctgt gggtgacaac cgtgtgcttg atatggcttc cacgtacttt   19140
gacatccgcg gcgtgctgga caggggggcct acttttaagc cctactccgg cactgcctac   19200
aacgctctag ctcccaaggg cgctcctaac tcctgtgagt gggaacaaac cgaagatagc   19260
ggccgggcag ttgccgagga tgaagaagag gaagatgaag atgaagaaga ggaagaagaa   19320
gagcaaaacg ctcgagatca ggctactaag aaaacacatg tctatgccca ggctcctttg   19380
tctggagaaa caattacaaa aagcgggcta caaataggat cagacaatgc agaaacacaa   19440
gctaaacctg tatacgcaga tccttcctat caaccagaac tcaaattgg cgaatctcag   19500 tggaacgaag ctgatgctaa tgcggcagga gggagagtgc ttaaaaaaac aactcccatg   19560
aaaccatgct atggatctta tgccaggcct acaaatcctt ttggtggtca atccgttctg   19620
gttccggatg aaaaaggggt gcctcttcca aaggttgact tgcaattctt ctcaaatact   19680
acctctttga acgaccggca aggcaatgct actaaaccaa aagtggtttt gtacagtgaa   19740
```

-continued

```
gatgtaaata tggaaacccc agacacacat ctgtcttaca aacctggaaa aggtgatgaa   19800
aattctaaag ctatgttggg tcaacaatct atgccaaaca gacccaatta cattgctttc   19860
agggacaatt ttattggcct aatgtattat aacagcactg gcaacatggg tgttcttgct   19920
ggtcaggcat cgcagctaaa tgccgtggta gatttgcaag acagaaacac agagctgtcc   19980
tatcaactct tgcttgattc cataggtgat agaaccagat attttttctat gtggaatcag   20040 gctgtagaca gctatgatcc agatgttaga atcattgaaa accatggaac tgaggatgaa   20100
ttgccaaatt attgttttcc tcttgggggt attggggtaa ctgacaccta tcaagctatt   20160
aaggctaatg gcaatggctc aggcgataat ggagatacta catggacaaa agatgaaact   20220
tttgcaacac gtaatgaaat aggagtgggt aacaactttg ccatggaaat taacctaaat   20280
gccaacctat ggagaaattt cctttactcc aatattgcgc tgtacctgcc agacaagcta   20340
aaatacaacc ccaccaatgt ggaaatatct gacaacccca acacctacga ctacatgaac   20400
aagcgagtgg tggctcccgg gcttgtagac tgctacatta accttggggc gcgctggtct   20460
ctggactaca tggacaacgt taatcccttt aaccaccacc gcaatgcggg cctccgttat   20520
cgctccatgt tgttgggaaa cggccgctac gtgccctttc acattcaggt gccccaaaag   20580
ttttttgcca ttaaaaacct cctcctcctg ccaggctcat atacatatga atggaacttc   20640
aggaaggatg ttaacatggt tctgcagagc tctctgggaa acgatcttag agttgacggg   20700
gctagcatta agtttgacag catttgtctt tacgccacct tcttccccat ggcccacaac   20760
acggcctcca cgctggaagc catgctcaga aatgacacca acgaccagtc ctttaatgac   20820
tacctttccg ccgccaacat gctataccc ataccgcca acgccaccaa cgtgcccatc   20880
tccatcccat cgcgcaactg ggcagcattt cgcggttggg ccttcacacg cttgaagaca   20940
aaggaaaccc cttccctggg atcaggctac gacccttact acacctactc tggctccata   21000
ccataccttg acggaacctt ctatcttaat cacaccttta agaaggtggc cattacctttt   21060 gactcttctg ttagctggcc gggcaacgac cgcctgctta ctcccaatga gtttgagatt   21120
aaacgctcag ttgacggggga gggctacaac gtagctcagt gcaacatgac caaggactgg   21180
ttcctggtgc agatgttggc caactacaat attggctacc agggcttcta cattccagaa   21240
agctacaagg accgcatgta ctcgttcttc agaaacttcc agcccatgag ccggcaagtg   21300
gttgacgata ctaaatacaa ggagtatcag caggttggaa ttcttcacca gcataacaac   21360
tcaggattcg taggctacct cgctcccacc atgcgcgagg gacaggctta ccccgccaac   21420
gtgccctacc cactaatagg caaaaccgcg gttgacagta ttacccagaa aaagtttctt   21480
tgcgatcgca ccctttggcg catcccattc tccagtaact ttatgtccat gggcgcactc   21540
acagacctgg gccaaaacct tctctacgcc aactccgccc acgcgctaga catgactttt   21600
gaggtggatc ccatggacga gcccacccct ctttatgttt tgtttgaagt ctttgacgtg   21660
gtccgtgtgc accagccgca ccgcggcgtc atcgagaccg tgtacctgcg cacgcccttc   21720
tcggccggca acgccacaac ataaaagaag caagcaacat caacaacagc tgccgccatg   21780
ggctccagtg agcaggaact gaaagccatt gtcaaagatc ttggttgtgg gccatatttt   21840
ttgggcacct atgacaagcg ctttccaggc tttgtttctc cacacaagct cgcctgcgcc   21900
atagtcaata cggccggtcg cgagactggg ggcgtacact ggatggcctt tgcctggaac   21960
ccgcgctcaa aaacatgcta cctctttgag ccctttggct tttctgacca acgactcaag   22020
caggtttacc agtttgagta cgagtcactc ctgcgccgta gcgccattgc ttcttccccc   22080
```

-continued

```
gaccgctgta taacgctgga aaagtccacc caaagcgtgc aggggcccaa ctcggccgcc   22140
tgtggactat tctgctgcat gtttctccac gcctttgcca actggcccca aactcccatg   22200
gatcacaacc ccaccatgaa ccttattacc ggggtaccca actccatgct taacagtccc   22260
caggtacagc ccaccctgcg tcgcaaccag gaacagctct acagcttcct ggagcgccac   22320
tcgccctact tccgcagcca cagtgcgcag attaggagcg ccacttcttt ttgtcacttg   22380
aaaaacatgt aaaaataatg tactaggaga cactttcaat aaaggcaaat gttttattt    22440 gtacactctc gggtgattat ttacccccca cccttgccgt ctgcgccgtt taaaaatcaa   22500
aggggttctg ccgcgcatcg ctatgcgcca ctggcaggga cacgttgcga tactggtgtt   22560
tagtgctcca cttaaactca ggcacaacca tccgcggcag ctcggtgaag tttcactcc    22620 acaggctgcg caccatcacc aacgcgttta gcaggtcggg cgccgatatc ttgaagtcgc   22680
agttggggcc tccgccctgc gcgcgcgagt tgcgatacac agggttgcag cactggaaca   22740
ctatcagcgc cgggtggtgc acgctggcca gcacgctctt gtcggagatc agatccgcgt   22800
ccaggtcctc cgcgttgctc agggcgaacg gagtcaactt tggtagctgc cttcccaaaa   22860
agggtgcatg cccaggcttt gagttgcact cgcaccgtag tggcatcaga aggtgaccgt   22920
gcccggtctg ggcgttagga tacagcgcct gcatgaaagc cttgatctgc ttaaaagcca   22980
cctgagcctt tgcgccttca gagaagaaca tgccgcaaga cttgccggaa aactgattgg   23040
ccggacaggc cgcgtcatgc acgcagcacc ttgcgtcggt gttggagatc tgcaccacat   23100
ttcggcccca ccggttcttc acgatcttgg ccttgctaga ctgctccttc agcgcgcgct   23160
gcccgttttc gctcgtcaca tccatttcaa tcacgtgctc cttatttatc ataatgctcc   23220
cgtgtagaca cttaagctcg ccttcgatct cagcgcagcg gtgcagccac aacgcgcagc   23280
ccgtgggctc gtggtgcttg taggttacct ctgcaaacga ctgcaggtac gcctgcagga   23340
atcgccccat catcgtcaca aaggtcttgt tgctggtgaa ggtcagctgc aacccgcggt   23400
gctcctcgtt tagccaggtc ttgcatacgg ccgccagagc ttccacttgg tcaggcagta   23460
gcttgaagtt tgcctttaga tcgttatcca cgtggtactt gtccatcaac gcgcgcgcag   23520
cctccatgcc cttctcccac gcagacacga tcggcaggct cagcgggttt atcaccgtgc   23580
tttcactttc cgcttcactg gactcttcct tttcctcttg cgtccgcata ccccgcgcca   23640
ctgggtcgtc ttcattcagc cgccgcaccg tgcgcttacc tcccttgccg tgcttgatta   23700
gcaccggtgg gttgctgaaa cccaccattt gtagcgccac atcttctctt tcttcctcgc   23760
tgtccacgat cacctctggg gatggcgggc gctcgggctt gggagagggg cgcttctttt   23820 tcttttttgga cgcaatggcc aaatccgccg tcgaggtcga tggccgcggg ctgggtgtgc   23880
gcggcaccag cgcatcttgt gacgagtctt cttcgtcctc ggactcgaga cgccgcctca   23940
gccgcttttt tgggggcgcg cggggaggcg gcggcgacgg cgacggggac gacacgtcct   24000
ccatggttgg tggacgtcgc gccgcaccgc gtccgcgctc ggggagtgtt tcgcgctgct   24060
cctcttcccg actggccatt tccttctcct ataggcagaa aaagatcatg gagtcagtcg   24120
agaaggagga cagcctaacc gcccccttg agttcgccac caccgcctcc accgatgccg   24180
ccaacgcgcc taccaccttc cccgtcgagg cacccccgct tgaggaggag gaagtgatta   24240
tcgagcagga cccaggtttt gtaagcgaag acgacgagga tcgctcagta ccaacagagg   24300
ataaaaagca agaccaggac gacgcagagg caaacgagga acaagtcggg cgggggacc     24360 aaaggcatgg cgactaccta gatgtgggag acgacgtgct gttgaagcat ctgcagcgcc   24420
agtgcgccat tatctgcgac gcgttgcaag agcgcagcga tgtgcccctc gccatagcgg   24480
```

```
atgtcagcct tgcctacgaa cgccacctgt tctcaccgcg cgtacccccc aaacgccaag   24540
aaaacggcac atgcgagccc aacccgcgcc tcaacttcta ccccgtattt gccgtgccag   24600
aggtgcttgc cacctatcac atctttttcc aaaactgcaa gataccccta tcctgccgtg   24660
ccaaccgcag ccgagcggac aagcagctgg ccttgcggca gggcgctgtc atacctgata   24720
tcgcctcgct cgacgaagtg ccaaaaatct ttgagggtct tggacgcgac gagaaacgcg   24780
cggcaaacgc tctgcaacaa gaaaacagcg aaaatgaaag tcactgtgga gtgctggtgg   24840
aacttgaggg tgacaacgcg cgcctagccg tgctgaaacg cagcatcgag gtcacccact   24900
ttgcctaccc ggcacttaac ctaccccca aggttatgag cacagtcatg agcgagctga   24960
tcgtgcgccg tgcacgaccc ctggagaggg atgcaaactt gcaagaacaa accgaggagg   25020
gcctacccgc agttggcgat gagcagctgg cgcgctggct tgagacgcgc gagcctgccg   25080
acttggagga gcgacgcaag ctaatgatgg ccgcagtgct tgttaccgtg gagcttgagt   25140
gcatgcagcg gttctttgct gacccggaga tgcagcgcaa gctagaggaa acgttgcact   25200
acacctttcg ccagggctac gtgcgccagg cctgcaaaat ttccaacgtg gagctctgca   25260
acctggtctc ctaccttgga attttgcacg aaaaccgcct cgggcaaaac gtgcttcatt   25320
ccacgctcaa gggcgaggcg cgccgcgact acgtccgcga ctgcgtttac ttatttctgt   25380
gctacacctg gcaaacggcc atgggcgtgt ggcagcaatg cctggaggag cgcaacctaa   25440
aggagctgca gaagctgcta aagcaaaact tgaaggacct atggacggcc ttcaacgagc   25500
gctccgtggc cgcgcacctg gcggacatta tcttccccga acgcctgctt aaaaccctgc   25560
aacagggtct gccagacttc accagtcaaa gcatgttgca aaactttagg aactttatcc   25620
tagagcgttc aggaattctg cccgccacct gctgtgcgct tcctagcgac tttgtgccca   25680
ttaagtaccg tgaatgccct ccgccgcttt ggggtcactg ctaccttctg cagctagcca   25740
actaccttgc ctaccactcc gacatcatgg aagacgtgag cggtgacggc ctactggagt   25800
gtcactgtcg ctgcaaccta tgcaccccgc accgctccct ggtctgcaat tcgcaactgc   25860
ttagcgaaag tcaaattatc ggtacctttg agctgcaggg tccctcgcct gacgaaaagt   25920
ccgcggctcc ggggttgaaa ctcactccgg ggctgtggac gtcggcttac cttcgcaaat   25980
ttgtacctga ggactaccac gcccacgaga ttaggttcta cgaagaccaa tcccgcccgc   26040
caaatgcgga gcttaccgcc tgcgtcatta cccagggcca catccttggc caattgcaag   26100
ccatcaacaa agcccgccaa gagtttctgc tacgaaaggg acggggggtt tacctggacc   26160
cccagtccgg cgaggagctc aacccaatcc ccccgccgcc gcagccctat cagcagccgc   26220
gggcccttgc ttcccaggat ggcacccaaa aagaagctgc agctgccgcc gccgccaccc   26280
acggacgagg aggaatactg ggacagtcag gcagaggagg ttttggacga ggaggaggag   26340
atgatggaag actgggacag cctagacgaa gcttccgagg ccgaagaggt gtcagacgaa   26400
acaccgtcac cctcggtcgc attccccctcg ccggcgcccc agaaattggc aaccgttccc   26460
agcatcgcta caacctccgc tcctcaggcg ccgccggcac tgcctgttcg ccgacccaac   26520
cgtagatggg acaccactgg aaccagggcc ggtaagtcta agcagccgcc gccgttagcc   26580
caagagcaac aacagcgcca aggctaccgc tcgtggcgcg ggcacaagaa cgccatagtt   26640
gcttgcttgc aagactgtgg gggcaacatc tccttcgccc gccgctttct tctctaccat   26700
cacggcgtgg ccttcccccg taacatcctg cattactacc gtcatctcta cagcccctac   26760
tgcaccggcg gcagcggcag cggcagcaac agcagcggtc acacagaagc aaaggcgacc   26820
```

-continued

```
ggatagcaag actctgacaa agcccaagaa atccacagcg gcggcagcag caggaggagg   26880
agcgctgcgt ctggcgccca acgaacccgt atcgacccgc gagcttagaa ataggatttt   26940
tcccactctg tatgctatat ttcaacaaag caggggccaa gaacaagagc tgaaaataaa   27000
aaacaggtct ctgcgctccc tcacccgcag ctgcctgtat cacaaaagcg aagatcagct   27060
tcggcgcacg ctggaagacg cggaggctct cttcagcaaa tactgcgcgc tgactcttaa   27120
ggactagttt cgcgcccttt ctcaaattta agcgcgaaaa ctacgtcatc tccagcggcc   27180
acacccggcg ccagcacctg tcgtcagcgc cattatgagc aaggaaattc ccacgcccta   27240
catgtggagt taccagccac aaatgggact tgcggctgga gctgcccaag actactcaac   27300
ccgaataaac tacatgagcg cgggacccca catgatatcc cgggtcaacg gaatccgcgc   27360
ccaccgaaac cgaattctcc tcgaacaggc ggctattacc accacacctc gtaataacct   27420
taatccccgt agttggcccg ctgccctggt gtaccaggaa agtcccgctc ccaccactgt   27480
ggtacttccc agagacgccc aggccgaagt tcagatgact aactcagggg cgcagcttgc   27540
gggcggcttt cgtcacaggg tgcggtcgcc cgggcagggt ataactcacc tgaaaatcag   27600
agggcgaggt attcagctca acgacgagtc ggtgagctcc tctcttggtc tccgtccgga   27660
cgggacattt cagatcggcg gcgctggccg ctcttcattt acgccccgtc aggcgatcct   27720
aactctgcag acctcgtcct cggagccgcg ctccggaggc attggaactc tacaatttat   27780
tgaggagttc gtgccttcgg tttacttcaa cccctttcct ggacctcccg gccactaccc   27840
ggaccagttt attcccaact ttgacgcggt gaaagactcg gcggacggct acgactgaat   27900
gaccagtgga gaggcagagc gactgcgcct gacacacctc gaccactgcc gccgccacaa   27960
gtgctttgcc cgcggctccg gtgagttttg ttactttgaa ttgcccgaag agcatatcga   28020
gggcccggcg cacggcgtcc ggctcaccac ccaggtagag cttacacgta gcctgattcg   28080
ggagtttacc aagcgccccc tgctagtgga gcgggagcgg ggtccctgtg ttctgaccgt   28140
ggtttgcaac tgtcctaacc ctggattaca tcaagatctt tgttgtcatc tctgtgctga   28200
gtataataaa tacagaaatt agaatctact ggggctcctg tcgccatcct gtgaacgcca   28260 ccgttttttac ccacccaaag cagaccaaag caaacctcac ctccggtttg cacaagcggg   28320
ccaataagta ccttacctgg tactttaacg gctcttcatt tgtaatttac aacagtttcc   28380
agcgagacga agtaagtttg ccacacaacc ttctcggctt caactacacc gtcaagaaaa   28440
acaccaccac caccaccctc ctcacctgcc gggaacgtac gagtgcgtca ccggttgctg   28500
cgcccacacc tacagcctga gcgtaaccag acattactcc catttttcca aaacaggagg   28560
tgagctcaac tcccggaact caggtcaaaa aagcattttg cggggtgctg ggattttta    28620 attaagtata tgagcaattc aagtaactct acaagcttgt ctaatttttc tggaattggg   28680
gtcggggtta tccttactct tgtaattctg tttattctta tactagcact tctgtgcctt   28740
agggttgccg cctgctgcac gcacgtttgt acctattgtc agcttttaa acgctggggg    28800 caacatccaa gatgaggtac atgattttag gcttgctcgc ccttgcggca gtctgcagcg   28860
ctgccaaaaa ggttgagttt aaggaaccag cttgcaatgt tacatttaaa tcagaagcta   28920
atgaatgcac tactcttata aaatgcacca cagaacatga aaagcttatt attcgccaca   28980
aagacaaaat tggcaagtat gctgtatatg ctatttggca gccaggtgac actaacgact   29040
ataatgtcac agtcttccaa ggtgaaaatc gtaaaacttt tatgtataaa tttccatttt   29100
atgaaatgtg cgatattacc atgtacatga gcaaacagta caagtgtggg cccccacaaa   29160
agtgtttaga gaacactggc acctttttgtt ccaccgctct gcttattaca gcgcttgctt   29220
```

-continued

```
tggtatgtac cttactttat ctcaaataca aaagcagacg cagttttatt gatgaaaaga   29280
aaatgccttg attttccgct tgcttgtatt cccctggaca atttactcta tgtgggatat   29340
gctccaggcg ggcaagatta tacccacaac cttcaaatca aactttcctg gacgttagcg   29400
cctgatttct gccagcgcct gcactgcaaa tttgatcaaa cccagcttca gcttgcctgc   29460
tccagagatg accggctcaa ccatcgcgcc cacaacggac tatcgcaaca ccactgctac   29520
cggactaaca tctgccctaa atttacccca agttcatgcc tttgtcaatg actgggcgag   29580
cttggacatg tggtggtttt ccatagcgct tatgtttgtt tgccttatta ttatgtggct   29640
tatttgttgc ctaaagcgca gacgcgccag accccccatc tataggccta tcattgtgct   29700
caacccacac aatgaaaaaa ttcatagatt ggacggtctg aaaccatgtt ctcttctttt   29760
acagtatgat taaatgagac atgattcctc gagttcttat attattgacc cttgttgcgc   29820
ttttctgtgc gtgctctaca ttggccgcgg tcgctcacat cgaagtagat tgcatcccac   29880 cttttcacagt ttacctgctt tacggatttg tcacccttat cctcatctgc agcctcgtca   29940
ctgtagtcat cgccttcatt cagttcattg actgggtttg tgtgcgcatt gcgtacctca   30000
ggcaccatcc gcaatacaga gacaggacta tagctgatct tctcagaatt ctttaattat   30060
gaaacggagt gtcatttttg ttttgctgat tttttgcgcc ctacctgtgc tttgctccca   30120
aacctcagcg cctcccaaaa gacatatttc ctgcagattc actcaaatat ggaacattcc   30180
cagctgctac aacaaacaga gcgatttgtc agaagcctgg ttatacgcca tcatctctgt   30240
catggttttt tgcagtacca tttttgccct agccatatat ccataccttg acattggctg   30300
gaatgccata gatgccatga accaccctac tttcccagtg cccgctgtca taccactgca   30360
acaggttatt gccccaatca atcagcctcg cccccccttct cccaccccca ctgagattag   30420
ctactttaat ttgacaggtg gagatgactg aatctctaga tctagaattg gatggaatta   30480
acaccgaaca gcgcctacta gaaaggcgca aggcggcgtc cgagcgagaa cgcctaaaac   30540
aagaagttga agacatggtt aacctacacc agtgtaaaag aggtatcttt tgtgtggtca   30600
agcaggccaa acttacctac gaaaaaacca ctaccggcaa ccgcctcagc tacaagctac   30660
ccacccagcg ccaaaaactg gtgcttatgg tgggagaaaa acctatcacc gtcacccagc   30720
actcggcaga aacagagggc tgcctgcact tcccctatca gggtccagag gacctctgca   30780
ctcttattaa aaccatgtgt ggtattagag atcttattcc attcaactaa cataaacaca   30840
caataaatta cttacttaaa atcagtcagc aaatctttgt ccagcttatt cagcatcacc   30900
tcctttcctt cctcccaact ctggtatctc agccgccttt tagctgcaaa ctttctccaa   30960
agtttaaatg ggatgtcaaa ttcctcatgt tcttgtccct ccgcaccac tatcttcata   31020 ttgttgcaga tgaaacgcgc cagaccgtct gaagacacct tcaaccccgt gtatccatat   31080
gacacagaaa ccgggcctcc aactgtgccc tttcttaccc ctccatttgt ttcacccaat   31140
ggtttccaag aaagtccccc tggagttctc tctctacgcg tctccgaacc tttgacacc   31200 tcccacggca tgcttgcgct taaaatgggc agcggtctta ccctagacaa ggccggaaac   31260
ctcacctccc aaaatgtaac cactgttact cagccactta aaaaacaaa gtcaaacata   31320 agtttggaca cctccgcacc acttacaatt acctcaggcg ccctaacagt ggcaaccacc   31380
gctcctctga tagttactag cggcgctctt agcgtacagt cacaagcccc actgaccgtg   31440
caagactcca aactaagcat tgctactaaa gggcccatta cagtgtcaga tggaaagcta   31500
gccctgcaaa catcagcccc cctctctggc agtgacagcg acacccttac tgtaactgca   31560
```

```
tcaccccgc  taactactgc  cacgggtagc  ttgggcatta  acatggaaga  tcctatttat  31620
gtaaataatg  gaaaaatagg  aattaaaata  agcggtcctt  tgcaagtagc  acaaaactcc  31680
gatacactaa  cagtagttac  tggaccaggt  gtcaccgttg  aacaaaactc  ccttagaacc  31740
aaagttgcag  gagctattgg  ttatgattca  tcaaacaaca  tggaaattaa  aacgggcggt  31800
ggcatgcgta  taaataacaa  cttgttaatt  ctagatgtgg  attacccatt  tgatgctcaa  31860
acaaaactac  gtcttaaact  ggggcaggga  cccctgtata  ttaatgcatc  tcataacttg  31920
gacataaact  ataacagagg  cctatacctt  tttaatgcat  caaacaatac  taaaaaactg  31980
gaagttagca  taaaaaaatc  cagtggacta  aactttgata  atactgccat  agctataaat  32040
gcaggaaagg  gtctggagtt  tgatacaaac  acatctgagt  ctccagatat  caacccaata  32100
aaaactaaaa  ttggctctgg  cattgattac  aatgaaaacg  gtgccatgat  tactaaactt  32160
ggagcgggtt  taagctttga  caactcaggg  gccattacaa  taggaaacaa  aaatgatgac  32220
aaacttaccc  tgtggacaac  cccagaccca  tctcctaact  gcagaattca  ttcagataat  32280
gactgcaaat  ttactttggt  tcttacaaaa  tgtgggagtc  aagtactagc  tactgtagct  32340
gctttggctg  tatctggaga  tctttcatcc  atgacaggca  ccgttgcaag  tgttagtata  32400
ttccttagat  ttgaccaaaa  cggtgttcta  atggagaact  cctcacttaa  aaaacattac  32460
tggaacttta  gaaatgggaa  ctcaactaat  gcaaatccat  acacaaatgc  agttggattt  32520
atgcctaacc  ttctagccta  tccaaaaacc  caaagtcaaa  ctgctaaaaa  taacattgtc  32580
agtcaagttt  acttgcatgg  tgataaaact  aaacctatga  tacttaccat  tacacttaat  32640
ggcactagtg  aatccacaga  aactagcgag  gtaagcactt  actctatgtc  ttttacatgg  32700
tcctgggaaa  gtggaaaata  caccactgaa  acttttgcta  ccaactctta  caccttctcc  32760
tacattgccc  aggaataaag  aatcgtgaac  ctgttgcatg  ttatgtttca  acgtgtttat  32820
ttttcaattg  cagaaaattt  caagtcattt  ttcattcagt  agtatagccc  caccaccaca  32880
tagcttatat  tgatcaccgt  accttaatca  aactcacaga  accctagtat  tcaacctgcc  32940
acctccctcc  caacacacag  agtacacagt  cctttctccc  cggctggcct  taaaaagcat  33000
catatcatgg  gtaacagaca  tattcttagg  tgttatattc  cacacggttt  cctgtcgagc  33060
caaacgctca  tcagtgatat  taataaactc  cccgggcagc  tcgcttaagt  tcatgtcgct  33120
gtccagctgc  tgagccacag  gctgctgtcc  aacttgcggt  tgctcaacgg  gcggcgaagg  33180
ggaagtccac  gcctacatgg  gggtagagtc  ataatcgtgc  atcaggatag  ggcggtggtg  33240
ctgcagcagc  gcgcgaataa  actgctgccg  ccgccgctcc  gtcctgcagg  aatacaacat  33300
ggcagtggtc  tcctcagcga  tgattcgcac  cgcccgcagc  atgagacgcc  ttgtcctccg  33360
ggcacagcag  cgcaccctga  tctcacttaa  atcagcacag  taactgcagc  acagcaccac  33420
aatattgttc  aaaatcccac  agtgcaaggc  gctgtatcca  aagctcatgg  cggggaccac  33480
agaacccacg  tggccatcat  accacaagcg  caggtagatt  aagtggcgac  ccctcataaa  33540
cacgctggac  ataaacatta  cctcttttgg  catgttgtaa  ttcaccacct  cccggtacca  33600
tataaacctc  tgattaaaca  tggcgccatc  caccaccatc  ctaaaccagc  tggccaaaac  33660
ctgcccgccg  gctatgcact  gcagggaacc  gggactggaa  caatgacagt  ggagagccca  33720
ggactcgtaa  ccatggatca  tcatgctcgt  catgatatca  atgttggcac  aacacaggca  33780
cacgtgcata  cacttcctca  ggattacaag  ctcctcccgc  gtcagaacca  tatcccaggg  33840
aacaacccat  tcctgaatca  gcgtaaatcc  cacactgcag  ggaagacctc  gcacgtaact  33900
cacgttgtgc  attgtcaaag  tgttacattc  gggcagcagc  ggatgatcct  ccagtatggt  33960
```

-continued

```
agcgcgggtc tctgtctcaa aaggaggtag gcgatcccta ctgtacggag tgcgccgaga    34020
caaccgagat cgtgttggtc gtagtgtcat gccaaatgga acgccggacg tagtcatatt    34080
tcctgaagca aaaccaggtg cgggcgtgac aaacagatct gcgtctccgg tctcgtcgct    34140
tagctcgctc tgtgtagtag ttgtagtata tccactctct caaagcatcc aggcgccccc    34200
tggcttcggg ttctatgtaa actccttcat gcgccgctgc cctgataaca tccaccaccg    34260
cagaataagc cacacccagc caacctacac attcgttctg cgagtcacac acgggaggag    34320
cgggaagagc tggaagaacc atgttttttt tttttttatt ccaaaagatt atccaaaacc    34380
tcaaaatgaa gatctattaa gtgaacgcgc tcccctccgg tggcgtggtc aaactctaca    34440
gccaaagaac agataatggc atttgtaaga tgttgcacaa tggcttccaa aaggcaaact    34500
gccctcacgt ccaagtggac gtaaaggcta aacccttcag ggtgaatctc ctctataaac    34560
attccagcac cttcaaccat gcccaaataa ttttcatctc gccaccttat caatatgtct    34620
ctaagcaaat cccgaatatt aagtccggcc attgtaaaaa tctgctccag agcgccctcc    34680
accttcagcc tcaagcagcg aatcatgatt gcaaaaattc aggttcctca cagacctgta    34740
taagattcaa aagcggaaca ttaacaaaaa taccgcgatc ccgtaggtcc cttcgcaggg    34800
ccagctgaac ataatcgtgc aggtctgcac ggaccagcgc ggccacttcc ccgccaggaa    34860
ccatgacaaa agaacccaca ctgattatga cacgcatact cggagctatg ctaaccagcg    34920
tagcccctat gtaagcttgt tgcatgggcg gcgatataaa atgcaaggtg ctgctcaaaa    34980
aatcaggcaa agcctcgcgc aaaaaagcaa gcacatcgta gtcatgctca tgcagataaa    35040
ggcaggtaag ttccggaacc accacagaaa aagacaccat ttttctctca aacatgtctg    35100
cgggttcctg cattaaacac aaaataaaat aacaaaaaaa aacatttaaa cattagaagc    35160
ctgtcttaca acaggaaaaa caacccttat aagcataaga cggactacgg ccatgccggc    35220
gtgaccgtaa aaaactggt caccgtgatt aaaaagcacc accgacagtt cctcggtcat    35280
gtccggagtc ataatgtaag actcggtaaa cacatcaggt tggttaacat cggtcagtgc    35340
taaaaagcga ccgaaatagc ccggggggaat acatacccgc aggcgtagag acaacattac    35400
agcccccata ggaggtataa caaaattaat aggagagaaa aacacataaa cacctgaaaa    35460
accctcctgc ctaggcaaaa tagcaccctc ccgctccaga acaacataca gcgcttccac    35520
agcggcagcc ataacagtca gccttaccag taaaaaaacc tattaaaaaa caccactcga    35580
cacggcacca gctcaatcag tcacagtgta aaaagggcca agtacagagc gagtatatat    35640
aggactaaaa aatgacgtaa cggttaaagt ccacaaaaaa cacccagaaa accgcacgcg    35700
aacctacgcc cagaaacgaa agccaaaaaa cccacaactt cctcaaatct tcacttccgt    35760
tttcccacga tacgtcactt cccattttaa aaaaactaca attcccaata catgcaagtt    35820
actccgccct aaaacctacg tcacccgccc cgttcccacg ccccgcgcca cgtcacaaac    35880 tccacccccct cattatcata ttggcttcaa tccaaaataa ggtatattat gatgatg    35937
```